United States Patent
Pegurier et al.

(10) Patent No.: US 11,976,056 B2
(45) Date of Patent: May 7, 2024

(54) SUBSTITUTED ALKOXYPYRIDINYL INDOLSULFONAMIDES

(71) Applicant: UCB Pharma GmbH, Monheim (DE)

(72) Inventors: Cecile Pegurier, Uccle (BE); Laurent Provins, Soignies (BE); Emre M. Isin, Brussels (BE); Marie Ledecq, Eghezee (BE)

(73) Assignee: UCB PHARMA GMBH, Monheim (DE)

( * ) Notice: Subject to any disclaimer, the term of this patent is extended or adjusted under 35 U.S.C. 154(b) by 667 days.

(21) Appl. No.: 17/058,567

(22) PCT Filed: Jun. 19, 2019

(86) PCT No.: PCT/EP2019/066148
§ 371 (c)(1),
(2) Date: Nov. 24, 2020

(87) PCT Pub. No.: WO2019/243398
PCT Pub. Date: Dec. 26, 2019

(65) Prior Publication Data
US 2021/0214337 A1   Jul. 15, 2021

(30) Foreign Application Priority Data
Jun. 20, 2018   (EP) .................................... 18178773

(51) Int. Cl.
*C07D 401/12*   (2006.01)

(52) U.S. Cl.
CPC .................................. *C07D 401/12* (2013.01)

(58) Field of Classification Search
CPC ..................................................... C07D 401/12
USPC ........................................................... 514/339
See application file for complete search history.

(56) References Cited

U.S. PATENT DOCUMENTS

2013/0338374 A1   12/2013   Kostenis et al.

FOREIGN PATENT DOCUMENTS

WO   WO 2010/054307   5/2010

OTHER PUBLICATIONS

International Search Report dated Aug. 8, 2019 for International Application No. PCT/EP2019/066148, 2 pages.

*Primary Examiner* — Kahsay Habte
(74) *Attorney, Agent, or Firm* — McDonnell Boehnen Hulbert & Berghoff LLP

(57) ABSTRACT

The present application relates to alkoxy-substituted pyridinyl indolsulfonamides. The compounds are negative GPR17 modulators and have utility in the treatment of various GPR17 associated disorders.

20 Claims, No Drawings

SUBSTITUTED ALKOXYPYRIDINYL INDOLSULFONAMIDES

CROSS-REFERENCE TO RELATED APPLICATIONS

This application is a U.S. national phase of International Application No. PCT/EP2019/066148, filed Jun. 19, 2019, which claims priority from European Patent Application no. 18178773.0, filed Jun. 20, 2018, the disclosure of each of which is hereby incorporated by reference in its entirety.

BACKGROUND

G-protein coupled receptors (GPCRs) constitute the largest family of membrane receptors in the cell. They transduce extracellular signals to intracellular effector systems and are involved in a large variety of physiological phenomena, therefore representing the most common targets of pharmaceutical drugs although only a small percentage of GPCRs are targeted by current therapies.

GPCRs respond to a wide range of ligands. Due to the progress in human genome sequencing, for about 25% out of the more than 400 GPCRs (not including the olfactory GPCRs) that have been identified, a defined physiologically relevant ligand is still lacking. These receptors are known as "orphan GPCRs". "Deorphanization" and identification of their in vivo roles is expected to clarify novel regulatory mechanisms and, therefore, to disclose novel drug targets. Whether GPR17 is such an orphan receptor is still a matter of debate. Phylogenetically, GPR17 is closely related to the nucleotide P2Y receptors and the cysteinylleukotriene (CysLT1, CysLT2) receptors, with an amino acid sequence identity of between about 30 and about 35%, respectively.

Multiple-tissue Northern blot and RT-PCR analyses indicate a predominant expression of GPR17 in the central nervous system (CNS) (Ciana et al., 2006, EMBO J 25(19): 4615; Blasius et al., 1998, J Neurochem 70(4): 1357) and additionally in heart and kidney, i.e. organs typically undergoing ischemic damage. Two human GPR17 isoforms have been identified differing only by the length of their N-terminus. The short GPR17 isoform encodes a 339 amino acid-residue protein with typical rhodopsin type-seven transmembrane motifs. The long isoform encodes a receptor with a 28 amino acid longer N-terminus (Blasius et al., 1998). GPR17 is highly conserved among vertebrate species (~90% identity of amino acid sequence to both mouse and rat orthologs), which may constitute an advantageous feature for development of small molecule ligands and animal models in a drug discovery context.

In the original deorphaning report, GPR17 was identified as a dual receptor for uracil nucleotides and cysteinyl-leukotrienes (cysLTs) LTC4 and LTD4, respectively based on $^{35}$SGTPγS binding and cAMP inhibition assays as well as single cell calcium imaging (Ciana et al., 2006, ibid). Evidence for GPR17 functionality was provided in different cellular backgrounds such as 1321N1, COS 7, CHO, and HEK293 cells (Ciana et al., 2006, ibid). Subsequently, an independent study confirmed activation of GPR17 by uracil nucleotides but failed to recapitulate activation by CysLTs (Benned-Jensen and Rosenkilde, 2010, Br J Pharmacol, 159(5): 1092). Yet recent independent reports (Maekawa et al., 2009, PNAS 106(28), 11685; Qi et al., 2013, J Pharmacol Ther 347, 1, 38; Hennen et al., 2013, Sci Signal 6, 298) suggested lack of GPR17 responsiveness to both uracil nucleotides and CysLTs across different cellular backgrounds stably expressing GPR17 (1321N1, CHO, HEK293 cells). A novel regulatory role for GPR17 has also been proposed: GPR17— upon coexpression with the CysLT1 receptor—rendered the CysLT1 receptor unresponsive to its endogenous lipid mediators LTC4 and LTD4. Additional investigations are required to probe GPR17 pharmacology and function in more depth.

Drugs modulating the GPR17 activity may have neuroprotective, anti-inflammatory and anti-ischemic effects and may thus be useful for the treatment of cerebral, cardiac and renal ischemia, and stroke (WO 2006/045476), and/or for improving the recovery from these events (Bonfanti et al, Cell Death and Disease, 2017, 8, e2871).

GPR17 modulators are also thought to be involved in food uptake, insulin and leptin responses and are thus claimed to have a role in obesity treatment (WO 2011/113032).

Moreover, there is strong evidence that GPR17 is involved in myelination processes and that negative GPR17 modulators (antagonists or inverse agonists) can be valuable drugs for the treatment or alleviation of myelination disorders such as multiple sclerosis or spinal cord injury (Chen et al, Nature neuroscience 2009, 12(11):1398-1406; Ceruti et al; Brain: a journal of neurology 2009 132(Pt 8):2206-18; Hennen et al, Sci Signal, 6, 2013, 298; Simon et al J Biol Chem 291, 2016, 705; Fumagalli et al, Neuropharmacology 104, 2016, 82). More recently, two groups showed that adult GPR17−/− knock-out mice had faster remyelination than littermate wild-type after LPC induced demyelination in the spinal cord (Lu et al., Scientific Reports, 2018, 8:4502) or in the corpus callosum (Ou et al., J. Neurosci., 2016, 36(41): 10560). This again confirmed a potential crucial role in GPR17 in the remyelination process. In contrast, activation of GPR17 has been shown to inhibit oligodendrocyte precursor cells (OPCs) maturation thus preventing effective myelination (Simon et al, supra). The identification of potent and selective GPR17 antagonists or inverse agonists would thus be of significant relevance in the treatment of myelination disorders.

Several serious myelination diseases are known to be caused by disturbances in myelination, either by a loss of myelin (usually called demyelination), and/or by a failure of the body to properly form myelin (sometimes called dysmyelination). The myelination diseases may be idiopathic or secondary to certain trigger events like e.g. traumatic brain injury or viral infection. Myelination diseases may primarily affect the central nervous system (CNS) but may also concern the peripheral nervous system. Myelination diseases include, inter alia, multiple sclerosis, neuromyelitis optica (also known as Devic's disease), leucodystrophies, Guillain-Barré syndrome, and many other diseases as described in more detail further below (see also e.g. Love, J Clin Pathol, 59, 2006, 1151, Fumagalli et al, supra). Neurodegenerative diseases such as Alzheimer's Disease, Huntington's Disease, Parkinson's Disease, amyotropic lateral sclerosis (ALS) and multiple system atrophy (MSA) have been also strongly associated with decreased myelination recently (see e.g. Ettle et al, Mol Neurobiol 53, 2016, 3046; Jellinger and Welling, Movement Disorders, 31, 2016; 1767; Kang et al, Nature Neurosci 6, 2013, 571; Bartzokis, Neurochem Res (2007) 32:1655).

Multiple Sclerosis (MS) is a chronic progressive disorder. It is an inflammatory autoimmune disease causing oligodendrocyte damage, demyelination and ultimately axonal loss, thus leading to a broad spectrum of signs and symptoms of a severe neurological disease, like e.g. fatigue, dizziness, mobility and walking issues, speech and swallowing difficulties, pain and others. MS takes several forms, with new symptoms either occurring in isolated attacks (relapsing forms) or building up over time (progressive forms). While certain symptoms may disappear completely between isolated attacks, severe neurological problems often remain, especially as the disease advances to a more progressive form. According to the Multiple Sclerosis Association of America, approximately 400,000 individuals have been diagnosed with MS in the United States and as many as 2.5 million worldwide, with an estimated 10,000 new cases diagnosed in the United States annually. Multiple sclerosis is two to three times more common in women than in men.

There is no known causal treatment or cure for multiple sclerosis, or many other myelination diseases. Treatments are usually symptomatic and try to improve function after an attack and prevent new attacks, by addressing the inflammatory component of the disease. Such immunomodulatory drugs are usually only modestly effective, in particular if the disease is progressed, but can have side effects and be poorly tolerated. Moreover, most of the available drugs, like β-interferons, glatiramer acetate, or therapeutic antibodies are only available in injectable form and/or only address the inflammatory component of the disease but not demyelination directly Others drugs, like corticosteroids, show rather unspecific anti-inflammatory and immunosupressive effects thus potentially leading to chronic side effects, such as manifested in Cushing's syndrome, for example.

A strong need therefore exists for a safe and effective drug for the treatment of myelination diseases, like MS, preferably for a drug that is suitable for oral administration. Ideally such a drug would reverse the demyelination process by decreasing demyelination and/or by promoting remyelination of the impacted neurons. A chemical compound which effectively decreases the GPR17 receptor activity could fulfil these requirements.

However, only few chemical compounds are known that effectively modulate GPR17 activity.

WO 2005/103291 suggests the endogenous molecules 5 amino levulinic acid (5-ALA) and porphobilinogen (PBG) as activating ligands for GPR17, discloses analgesic effects of a GPR17 agonist and proposes the use of GPR17 agonists for treating neuropathic pain and as tools in GPR17 screening assays. However, the reported affinity of 5-ALA and PBG is quite low and the amounts needed in the assays are significant, namely in the three digit micromolar range for 5-ALA or even in the mM range for PBG, which make both compounds not well suited for use in routine screening assays or even for therapy. Moreover, PBG is a chemically unstable, reactive compound which rapidly decomposes after exposure to air and light, making it impractical to handle on a routine basis. Hence, these compounds do not offer a promising starting point to develop therapeutically effective negative GPR17 modulators.

Montelukast and pranlukast were originally developed as leukotriene receptor antagonists and were recently found to act on the GPR17 receptor as well (Ciana et al, EMBO J. 2006, 4615-4627). However, subsequent results in a functional assay were contradictory for montekulast (Hennen et al, 2013, ibid), while pharmacological inhibition of GPR17 with pranlukast promotes differentiation of primary mouse (Hennen et al., 2013, ibid) and rat (Ou et al., J. Neurosci. 36, 2016, 10560-10573) oligodendrocytes. Pranlukast even phenocopies the effect of GPR17 depression in a lysolecithin model of focal demyelination because both GPR17 knockout and pranlukast-treated wild-type mice show an earlier onset of remyelination (Ou, ibid). These results strongly support the hypothesis that GPR17 inhibitors offer potential for the treatment of animal/human demyelinating diseases.

However, the affinity of montekulast and prankulast to GPR17 is only in the high micromolar range (Kase et al, ACS Med. Chem. Lett. 2014, 5, 326-330). Given the high protein binding of both compounds and their poor brain penetration, it is unlikely that they could reach high enough free concentrations to bind to GPR17 receptors in amounts suitable for human therapy. In addition, results obtained in vivo with these compounds are difficult to interpret due to their confounding high affinity for CYSLT1 receptors. U.S. Pat. No. 8,623,593 discloses certain indole-2-carboxylic acids as GPR17 agonists and their use in screening assays. However, these derivatives are all potent agonists and are not suited to down-regulate GPR17 activity as needed in the treatment of myelination disorders such as MS. Moreover, this class of GPR17 activators does not sufficiently pass the blood-brain barrier due to their easily ionizable carboxyl groups, and were thus no suitable lead compounds to develop negative GPR17 modulators. See also Baqi et al, Med. Chem. Commun., 2014, 5, 86 and Kase et al, 2014, ibid.

WO 2013/167177 suggests certain phenyltriazole and benzodiazepine compounds as GPR17 antagonists. However, the disclosed compounds were selected solely based on in-silico screening results and no biological data at all was provided. The inventors of the present application were unable to confirm the GPR17 antagonist modulating activity of any of purported ligands proposed by the authors of this former patent application so far. A need therefore exists to identify potent modulators, preferably negative modulators, most preferably inverse agonists of GPR17, which are capable of effectively decreasing the GPR17 activity, preferably upon oral administration.

DESCRIPTION OF THE INVENTION

The present invention relates to compounds which act as negative modulators of the GPR17 receptor. In a preferred embodiment, the compounds act as negative agonists of the GPR17 receptor, thus inhibiting a constitutionally active GPR17.

The inventors of the present application have now found that pyridine-2-yl-indolsulfonamides with certain fluoroalkoxy substituents in para position of the pyridyl in combination with specific substituents in the "R7" position and with at least two additional substitutions in two other positions of the indol-pyridylsulfonamide core molecule, as specifically defined herein, provide very good GPR17 inhibitory activity along with improved properties. For example, the addition of specific substituents in "R7" as disclosed herein effectively diminishes a CYP 450-1A2 induction, which is often associated with this specific subclass of compounds, if R7 is hydrogen while the fluoroalkoxy substituent in para position of the pyridyl provides certain pharmacokinetic advantages such as less plasma protein binding compared to other substituents including e.g. halogens.

Accordingly, the present invention relates to compounds having Formula I

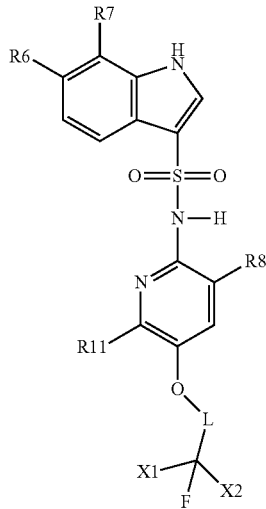

Formula I wherein
R6 is selected from fluoro, chloro, fluoromethyl and fluoromethoxy,
R7 is selected from fluoro, chloro, cyclopropyl, cyclopropyloxy, fluoromethyl, fluoroethyl,
fluoromethoxy and fluoroethoxy,
R8 is fluoro or methoxy,
R11 is hydrogen, fluoro or methoxy,
L is a bond, or a linker selected from —CH2-, and —CH2-CH2-O—,
X1 and X2 are independently selected from hydrogen and fluoro,
and pharmaceutically acceptable salts, solvates, isotopes and cocrystals thereof.

One embodiment relates to compounds of Formula I, wherein
R6 is selected from chloro, fluoromethyl and fluoromethoxy,
R7 is selected from fluoro, chloro, cyclopropyl, cyclopropyloxy, fluoromethyl, and fluoromethoxy,
R8 is fluoro or methoxy,
R11 is hydrogen, fluoro or methoxy,
L is a bond, or a linker selected from —CH2- and —CH2-CH2-O—,
X1 and X2 are independently selected from hydrogen and fluoro,
and pharmaceutically acceptable salts, solvates, isotopes and cocrystals thereof.

One embodiment relates to compounds of Formula I, wherein
R6 is selected from chloro, monofluoromethyl, difluoromethyl and trifluoromethyl, preferably from chloro and difluoromethyl,
R7 is selected from fluoro, chloro, cyclopropyl, cyclopropyloxy, fluoromethyl, and fluoromethoxy,
R8 is fluoro or methoxy,
R11 is hydrogen, fluoro or methoxy,
L is a bond, or a linker selected from —CH2- and —CH2-CH2-O—,
X1 and X2 are independently selected from hydrogen and fluoro,
and pharmaceutically acceptable salts, solvates, isotopes and cocrystals thereof.

One embodiment relates to compounds of Formula I, wherein R6 is chloro.

One embodiment relates to compounds of Formula I, wherein R6 is fluoro.

One embodiment relates to compounds of Formula I, wherein R6 is fluoromethyl, preferably difluoromethyl.

One embodiment relates to compounds of Formula I, wherein R7 is selected from fluoromethyl, cyclopropyloxy, fluoro and chloro.

One embodiment relates to compounds of Formula I, wherein R7 is fluoromethyl, preferably difluoromethyl.

One embodiment relates to compounds of Formula I, wherein R7 is fluoromethoxy, preferably difluoromethoxy or trifluoromethoxy.

One embodiment relates to compounds of Formula I, wherein R7 is chloro.

One embodiment relates to compounds of Formula I, wherein R7 is fluoro.

One embodiment relates to compounds of Formula I, wherein R7 is cyclopropyloxy.

One embodiment relates to compounds of Formula I, wherein R7 is cyclopropyl.

One embodiment relates to compounds of Formula I, wherein R11 is fluoro or hydrogen.

One embodiment relates to compounds of Formula I, wherein R11 is methoxy.

One embodiment relates to compounds of Formula I, wherein X1 is hydrogen.

One embodiment relates to compounds of Formula I, wherein L is selected from (a) a bond (b) —CH2- and (c) —CH2-CH2-O—, such compound thus having a structure according to Formulae Ia, Ib or Ic, wherein any substituent have the meaning as described for Formula I hereinbefore.

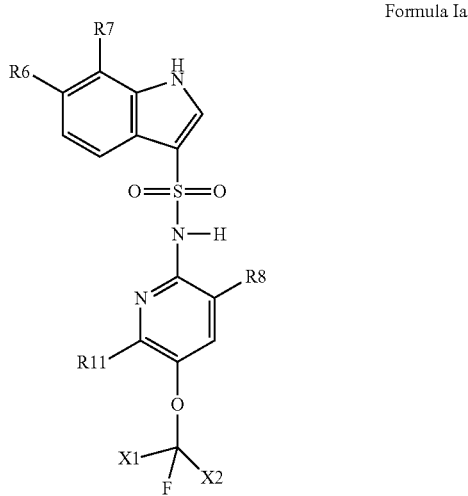

Formula Ia

Formula Ib

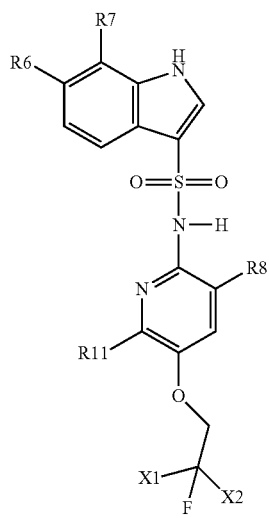

Formula Ic

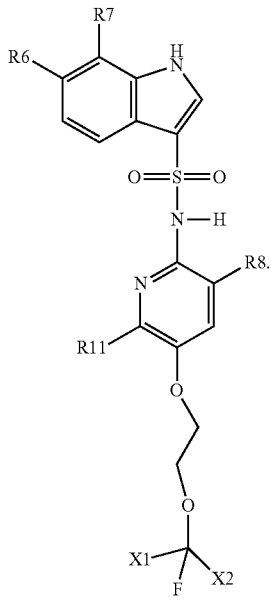

Formula IIa

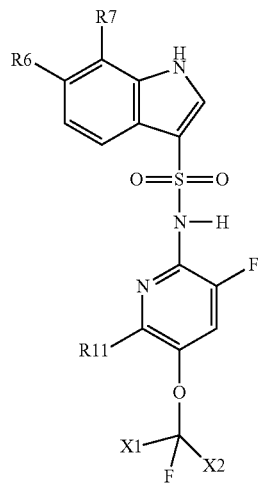

Formula IIb

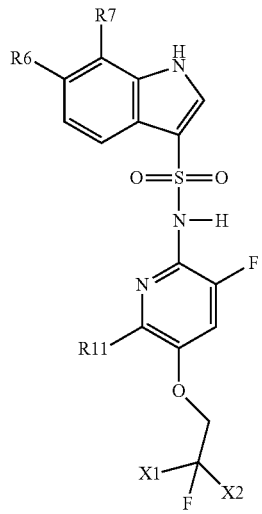

Formula IIc

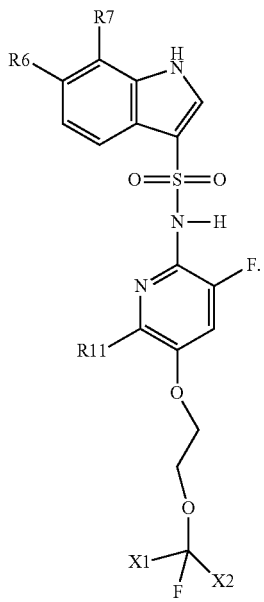

One embodiment relates to a compound having on of Formula Ia, Ib or Ic, wherein R6 is selected from chloro and fluoromethyl, preferably from chloro and difluoromethyl R7 is selected from fluoro, chloro, cyclopropyl, cyclopropyloxy, fluoromethyl and fluoromethoxy R11 is selected from hydrogen, methoxy and fluoro X1 and X2 are independently selected from hydrogen and fluoro.

One embodiment relates to compounds of Formula I as described hereinbefore, wherein R8 is fluoro and wherein L is selected from (a) a bond (b) —CH2- and (c) —CH2-CH2-O—, such compound thus having a structure according to Formulae IIa, IIb or IIc, wherein all other substituents are as described before.

One embodiment relates to compounds of Formula I, having one of formulae IIa, IIb or IIc, wherein R6 is selected from fluoro, chloro and fluoromethyl, preferably from chloro and difluoromethyl, R7 is selected from fluoro, chloro, cyclopropyl, cyclopropyloxy, fluoromethyl and fluoromethoxy, R11 is hydrogen, methoxy or fluoro, preferably methoxy or fluoro, X1 and X2 are independently selected from hydrogen and fluoro, wherein preferably X1 is hydrogen and X2 is fluoro.

One embodiment relates to compounds of Formula I as described hereinbefore, wherein R8 and R11 are both fluoro and wherein L is selected from (a) a bond (b) —CH2- and (c) —CH2-CH2-O—, such compound thus having a structure according to Formula IIIa, IIIb, or IIIc,

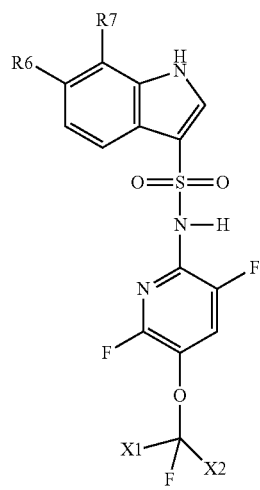

Formula IIIa

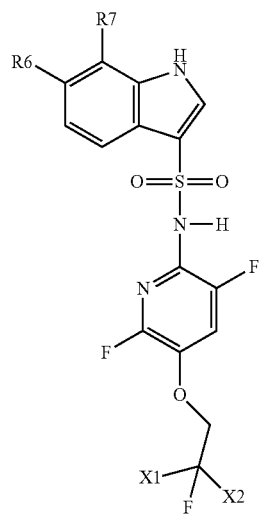

Formula IIIb

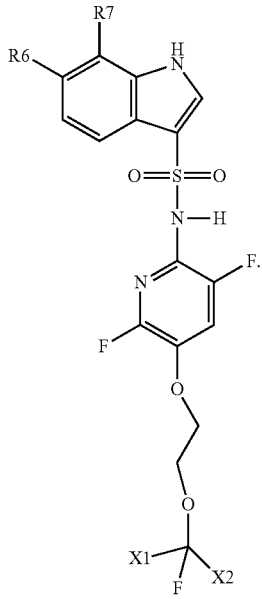

Formula IIIc wherein all other substituents are as described before.

One embodiment relates to compounds of formulae IIIa, IIIb or IIIc, wherein

R6 is selected from fluoro, chloro and fluoromethyl, preferably from chloro and difluoromethyl, R7 is selected from fluoro, chloro, cyclopropyl, cyclopropyloxy, fluoromethyl, and fluoromethoxy, X1 and X2 are independently selected from hydrogen and fluoro, and pharmaceutically acceptable salts, solvates, isotopes and cocrystals thereof.

One embodiment relates to compounds of Formula I, wherein R8 is fluoro, R11 is hydrogen and wherein L is selected from (a) a bond (b) —CH2- and (c) —CH2-CH2-O—, such compound thus having a structure according to Formula IVa, IVb, or IVc,

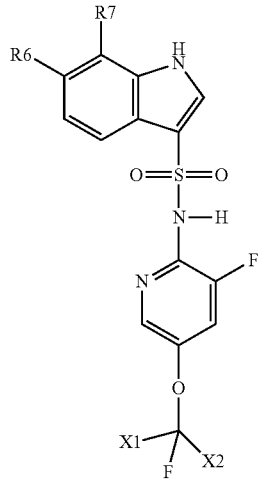

Formula IVa

Formula IVb

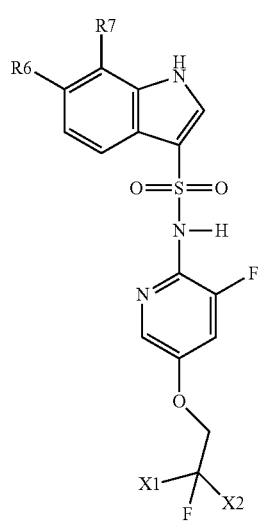

Formula IVc

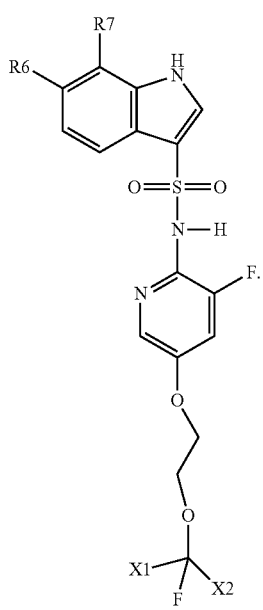

Formula Va

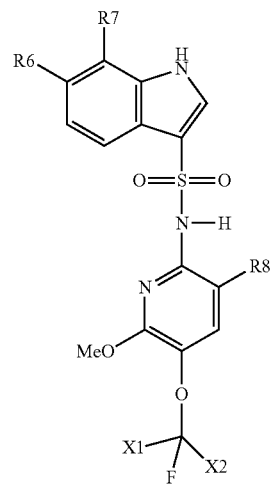

Formula Vb

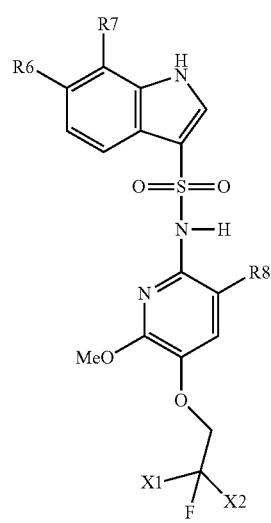

Formula Vc

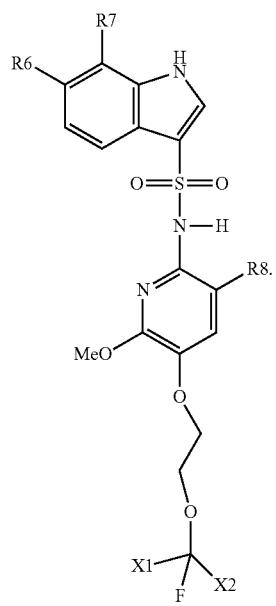

wherein all other substituents are as described hereinbefore.

One embodiment relates to compounds of Formula IVa, IVb, or IVc, wherein

R6 is selected from fluoro, chloro and fluoromethyl, preferably from chloro and difluoromethyl, R7 is selected from fluoro, chloro, cyclopropyl, cyclopropyloxy, fluoromethyl, and fluoromethoxy, X1 and X2 are independently selected from hydrogen and fluoro, and pharmaceutically acceptable salts, solvates, isotopes and cocrystals thereof.

One embodiment relates to compounds of Formula I as described hereinbefore, wherein, R11 is methoxy and wherein L is selected from (a) a bond (b) —CH2- and (c) —CH2-CH2-O—, such compound thus having a structure according to Formula Va, Vb or Vc:

wherein all other substituents are as described before.

In one embodiment, in compounds of Formula Va, Vb and Vc,
R6 is selected from fluoro, chloro, fluoromethyl and fluoromethoxy,
R7 is selected from fluoro, chloro, cyclopropyl, cyclopropyloxy, fluoromethyl, and fluoromethoxy, R8 is fluoro or methoxy, preferably fluoro, and
X1 and X2 are independently selected from hydrogen and fluoro.

In one embodiment, in compounds of Formula Va, Vb and Vc,
R6 is selected from chloro, monofluoromethyl, difluoromethyl and trifluoromethyl, preferably from chloro and difluoromethyl,
R7 is selected from fluoro, chloro, cyclopropyl, cyclopropyloxy, fluoromethyl, and fluoromethoxy,
R8 is fluoro or methoxy, preferably fluoro,
X1 and X2 are independently selected from hydrogen and fluoro, wherein in one embodiment, X2 is preferably hydrogen,
and pharmaceutically acceptable salts, solvates, isotopes and cocrystals thereof.

In one preferred embodiment, in compounds of Formula Va, Vb and Vc,
R6 is selected from chloro, monofluoromethyl, difluoromethyl and trifluoromethyl, preferably from chloro and difluoromethyl,
R7 is selected from fluoro, chloro, cyclopropyl, cyclopropyloxy and fluoromethyl,
R8 is fluoro,
X1 and X2 are independently selected from hydrogen and fluoro, wherein in one embodiment, X2 is preferably hydrogen,
and pharmaceutically acceptable salts, solvates, isotopes and cocrystals thereof.

One preferred embodiment relates to compounds of Formula I, wherein L is —CH2-, such compound thus having a structure according to Formula Ib,

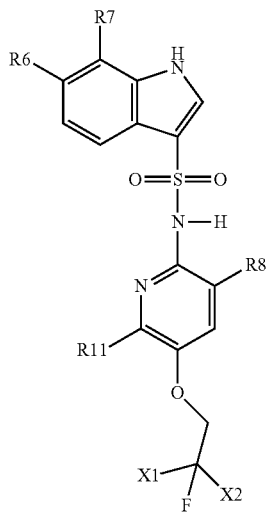

Formula Ib wherein
R6 is selected from fluoro, chloro, fluoromethyl and fluoromethoxy,
R7 is selected from fluoro, chloro, cyclopropyl, cyclopropyloxy, fluoromethyl, and fluoromethoxy,
R8 is fluoro or methoxy,
R11 is hydrogen, fluoro or methoxy,
X1 and X2 are independently selected from hydrogen and fluoro,
and pharmaceutically acceptable salts, solvates, isotopes and cocrystals thereof.

One preferred embodiment relates to compounds of Formula Ib, wherein
R6 is selected from chloro and fluoromethyl, preferably from chloro and difluoromethyl,
R7 is selected from chloro, cyclopropyl, cyclopropyloxy, fluoromethyl and fluoromethoxy
R8 is fluoro or methoxy,
R11 is selected from hydrogen, methoxy and fluoro,
X1 is hydrogen, and X2 is hydrogen or fluoro One preferred embodiment relates to compounds of Formula Ib, wherein
R6 is selected from chloro and fluoromethyl, preferably from chloro and difluoromethyl,
R7 is selected from chloro, cyclopropyl, cyclopropyloxy, fluoromethyl and fluoromethoxy
R8 is fluoro,
R11 is selected from hydrogen and fluoro,
X1 is hydrogen, and X2 is hydrogen or fluoro.

One preferred embodiment relates to compounds of Formula Ib, wherein
R6 is selected from chloro and difluoromethyl,
R7 is selected from chloro, cyclopropyloxy, fluoromethyl and fluoromethoxy
R8 is fluoro,
R11 is selected from hydrogen and fluoro,
X1 is hydrogen, and X2 is hydrogen or fluoro.

One preferred embodiment relates to compounds of Formula Ib, wherein
R6 is selected from fluoro, chloro and difluoromethyl,
R7 is selected from fluoro, chloro, cyclopropyloxy and fluoromethyl,
R8 is fluoro,
R11 is selected from methoxy and fluoro,
X1 is hydrogen, and X2 is hydrogen or fluoro.

One preferred embodiment relates to compounds of Formula Ib, wherein
R6 is selected from chloro and difluoromethyl,
R7 is selected from chloro, cyclopropyloxy, fluoromethyl and fluoromethoxy
R8 is fluoro,
R11 is methoxy,
X1 is hydrogen, and X2 is hydrogen or fluoro.

One preferred embodiment relates to compounds of Formula Ib, wherein
R6 is selected from chloro and difluoromethyl,
R7 is selected from chloro, cyclopropyloxy, and difluoromethyl,
R8 is fluoro,
R11 is selected from hydrogen, methoxy and fluoro, and is preferably methoxy,
X1 is hydrogen, and X2 is hydrogen or fluoro.

One embodiment relates to compounds of Formula Ib, wherein
R6 is selected from chloro and difluoromethyl,
R7 is selected from fluoro, chloro, cyclopropyloxy, difluoromethyl, difluoromethoxy and trifluoromethoxy,
R8 is methoxy,
R11 is selected from hydrogen and fluoro,
X1 is hydrogen, and X2 is hydrogen or fluoro.

One preferred embodiment relates to compounds of Formula Ib as described hereinbefore wherein R6 is difluoromethyl.

One preferred embodiment relates to compounds of Formula Ib as described hereinbefore wherein R7 is chloro.

One preferred embodiment relates to compounds of Formula Ib as described hereinbefore wherein R7 is fluoro.

One preferred embodiment relates to compounds of Formula Ib as described hereinbefore wherein R7 is difluoromethyl.

One preferred embodiment relates to compounds of Formula Ib as described hereinbefore wherein R8 is fluoro.

One preferred embodiment relates to compounds of Formula Ib as described hereinbefore wherein R8 is fluoro and R11 is methoxy.

One preferred embodiment relates to compounds of Formula Ib as described hereinbefore wherein R8 is fluoro and R11 is hydrogen One preferred embodiment relates to compounds of Formula Ib as described hereinbefore wherein R8 and R11 are both fluoro.

One preferred embodiment relates to compounds of Formula Ib as described hereinbefore wherein R8 is methoxy.

One preferred embodiment relates to compounds of Formula Ib as described hereinbefore wherein R8 is methoxy and R11 is fluoro.

One preferred embodiment relates to compounds of Formula Ib as described hereinbefore wherein R8 is methoxy and R11 is hydrogen.

One preferred embodiment relates to compounds of Formula Ib as described hereinbefore wherein R11 is fluoro.

One preferred embodiment relates to compounds of Formula Ib as described hereinbefore wherein R11 is hydrogen.

One preferred embodiment relates to compounds of Formula Ib as described hereinbefore wherein R11 is methoxy.

One preferred embodiment relates to compounds of Formula Ib as described hereinbefore wherein X1 and X2 are both hydrogen.

One preferred embodiment relates to compounds of Formula Ib as described hereinbefore wherein X1 is hydrogen and X2 is fluoro.

One preferred embodiment relates to compounds of Formula I, Ia, Ib, Ic, IIa, IIb, IIc, IIIa, IIIb, IIIc, IVa, IVb, IVc, Va, VB or Vc, wherein
  R6 is chloro,
  R7 is selected from fluoro, chloro, cyclopropyloxy, fluoromethyl and fluoromethoxy, and is preferably selected from chloro, cyclopropyloxy and difluoromethyl,
  and wherein X1 is hydrogen, and X2 is hydrogen or fluoro.

One preferred embodiment relates to compounds of Formula I, Ia, Ib, Ic, IIa, IIb, IIc, IIIa, IIIb, IIIc, IVa, IVb, IVc, Va, VB or Vc, wherein
  R6 is difluoromethyl
  R7 is selected from fluoro, chloro, cyclopropyloxy, fluoromethyl and fluoromethoxy, and is preferably selected from chloro, cyclopropyloxy and difluoromethyl,
  and wherein X1 is hydrogen, and X2 is hydrogen or fluoro.

One embodiment relates to any one of the compounds as described hereinbefore, wherein X1 is hydrogen and X2 is fluoro.

One embodiment relates to any one of the compounds as described hereinbefore, wherein X1 and X2 are both hydrogen.

One preferred embodiment relates to any one of the compounds as described hereinbefore wherein R6 is chloro.

One preferred embodiment relates to any one of the compounds as described hereinbefore wherein R6 is difluoromethyl.

One preferred embodiment relates to any one of the compounds as described hereinbefore wherein R7 is chloro.

One preferred embodiment relates to any one of the compounds as described hereinbefore wherein R7 is fluoro.

One preferred embodiment relates to any one of the compounds as described hereinbefore wherein R7 is difluoromethyl.

One embodiment relates to any one of the compounds as described hereinbefore wherein R7 is monofluoromethyl.

One embodiment relates to any one of the compounds as described hereinbefore wherein R7 is trifluoromethyl.

One embodiment relates to any one of the compounds as described hereinbefore wherein R7 is cyclopropyloxy.

One embodiment relates to any one of the compounds as described hereinbefore wherein R7 is monofluoromethoxy.

One embodiment relates to any one of the compounds as described hereinbefore wherein R7 is difluoromethoxy.

One embodiment relates to any one of the compounds as described hereinbefore wherein R7 is trifluoromethoxy.

A preferred embodiment relates to a compound selected from
6,7-dichloro-N-[5-(2,2-difluoroethoxy)-3-methoxypyridin-2-yl]-1H-indole-3-sulfonamide
7-chloro-N-[5-(2,2-difluoroethoxy)-3-fluoro-6-methoxypyridin-2-yl]-6-(difluoromethyl)-1H-indole-3-sulfonamide
6-chloro-N-[5-[2-(difluoromethoxy)ethoxy]-3-fluoro-6-methoxypyridin-2-yl]-7-fluoro-1H-indole-3-sulfonamide
6-chloro-N-[5-(2,2-difluoroethoxy)-3-fluoro-6-methoxypyridin-2-yl]-7-fluoro-1H-indole-3-sulfonamide
N-[5-(2,2-difluoroethoxy)-3-fluoropyridin-2-yl]-6-(difluoromethyl)-7-fluoro-1H-indole-3-sulfonamide
6-chloro-N-[3,6-difluoro-5-(2-fluoroethoxy)pyridin-2-yl]-7-(trifluoromethoxy)-1H-indole-3-sulfonamide
6-chloro-N-[5-(difluoromethoxy)-3-methoxypyridin-2-yl]-7-(difluoromethyl)-1H-indole-3-sulfonamide
6,7-dichloro-N-[5-(difluoromethoxy)-3-methoxypyridin-2-yl]-1H-indole-3-sulfonamide
6-chloro-N-[5-(2,2-difluoroethoxy)-3-fluoro-6-methoxypyridin-2-yl]-7-(difluoromethyl)-1H-indole-3-sulfonamide
6-chloro-N-[5-(2,2-difluoroethoxy)-3-fluoropyridin-2-yl]-7-(difluoromethyl)-1H-indole-3-sulfonamide
7-chloro-N-[3-fluoro-5-(2-fluoroethoxy)pyridin-2-yl]-6-(difluoromethyl)-1H-indole-3-sulfonamide
6-(difluoromethyl)-7-fluoro-N-[3-fluoro-5-(2-fluoroethoxy)pyridin-2-yl]-1H-indole-3-sulfonamide
6-chloro-7-(difluoromethyl)-N-[3-fluoro-5-(2-fluoroethoxy)pyridin-2-yl]-1H-indole-3-sulfonamide
6,7-dichloro-N-[5-(2,2-difluoroethoxy)-3-fluoropyridin-2-yl]-1H-indole-3-sulfonamide
6,7-dichloro-N-[3-fluoro-5-(2-fluoroethoxy)pyridin-2-yl]-1H-indole-3-sulfonamide
6-chloro-N-[3,6-difluoro-5-(2-fluoroethoxy)pyridin-2-yl]-7-fluoro-1H-indole-3-sulfonamide
6-chloro-N-[5-(2,2-difluoroethoxy)-3,6-difluoropyridin-2-yl]-7-fluoro-1H-indole-3-sulfonamide
6-chloro-7-cyclopropyl-N-[3,6-difluoro-5-(2-fluoroethoxy)pyridin-2-yl]-1H-indole-3-sulfonamide
6-chloro-N-[3,6-difluoro-5-(2-fluoroethoxy)pyridin-2-yl]-7-(difluoromethyl)-1H-indole-3-sulfonamide
6-chloro-7-cyclopropyloxy-N-[3,6-difluoro-5-(2-fluoroethoxy)pyridin-2-yl]-1H-indole-3-sulfonamide, and pharmaceutically acceptable salts, solvates, isotopes and cocrystals thereof.

For clarity, any definition of a compound as described hereinbefore also includes any pharmaceutically acceptable salts, solvates, isotopes and cocrystals thereof.

One embodiment relates to compounds of the present invention for use in therapy.

One embodiment relates to compounds of the present invention for use in treating or alleviating a demyelination disorder.

One embodiment relates to compounds of the present invention for use in treating or alleviating multiple sclerosis.

One embodiment relates to a method of treating a demyelination disorder, including but not limited to multiple sclerosis, comprising administering to a patient in need thereof a therapeutically effective amount of a compound as defined herein.

One embodiment relates to therapeutic compositions comprising at least one compound of the present invention and a pharmaceutically acceptable carrier.

Another preferred embodiment relates to compounds of the present invention comprising at least one 18 F isotope, preferably in the position of a fluorine atom as indicated in one of the compounds disclosed herein. By way of non-limiting example, in the compound 6-chloro-N-[3,6-difluoro-5-(2-fluoroethoxy)pyridin-2-yl]-7-fluoro-1H-indole-3-sulfonamide, disclosed herein, at least one of the four fluorines may be represented by a 18 F isotope. This applies likewise to other fluorine containing compounds described herein. These 18 F containing compounds can preferably be used as PET tracers.

Another preferred embodiment relates to compounds of the present invention comprising at least one $^{11}$C isotope, preferably in the position of a carbon atom as indicated herein. These $^{11}$C containing compounds can preferably be used as PET tracers.

Another preferred embodiment relates to compounds of the present invention comprising at least one $^{123}$I, $^{125}$I or $^{131}$I isotope, preferably in the position of a halogen atom as indicated herein. $^{123}$I, $^{125}$I or $^{131}$I containing compounds can preferably be used as SPECT tracers.

Therapeutic and Diagnostic Application

In one aspect, the invention relates to anyone of the compounds described herein, for use in therapy or diagnosis, particularly in the therapy of animals, in particular humans.

Because of their GPR17 modulating properties, the compounds of the present invention can be used as medicine, and may be used for the treatment and/or prevention of various diseases of the CNS system.

One embodiment of the present disclosure is thus a compound as described herein for use as a medicine, in particular for use as a medicine for the treatment and/or prevention of a GPR17-associated disease.

A GPR17 associated disease or disorder is disease which is associated with a dysfunction of the GPR17 signalling system such as, for example, an overexpression and/or overactivity of GPR17 receptors. Without wished to be bound by any theory, the activity of GPR17 may be increased, extended or otherwise altered in certain tissues, for example in oligodendrocyte progenitor cells (OPCs) or during maturation of oligondendrocytes, potentially due to activating endogeneous stimuli such as, for example, inflammation factors. High activity of GPR17 may prevent the differentiation of oligodendrocytes and an efficient myelination, thus promoting the emergence or further development of a myelination disease (see Chen et al, supra). Negative GPR17 modulators may thus promote myelination by decreasing or turning off GPR17 activity and by supporting OPC maturation into myelin-producing oligondendrocytes (see e.g. Simon et al, supra).

In one preferred aspect, the invention relates to anyone of the compounds described herein, for use in therapy or diagnosis for use in the prevention, or treatment of a disorder or syndrome selected from and/or associated with a myelination disorder, in particular a demyelination disorder, such as of the central nervous system. In one embodiment, the compounds of the present invention are for use in promoting, stimulating and/or accelerating remyelination in an animal in need thereof. In one embodiment, the remyelination associated with the administration of a compound of the present invention will prevent or treat a demyelination disease such as, but not limited to, multiple sclerosis.

Compounds of the present invention can also be useful in the treatment or prevention of a disorder or syndrome associated with brain tissue damage, a cerebrovascular disorder, and certain neurodegenerative diseases.

Neurodegenerative disorders have been recently associated strongly with a loss of myelination. Accordingly, it is believed that preserved oligodendroglial and myelin functionality is a crucial prerequisite for the prevention of axonal and neuronal degeneration (see e.g. Ettle et al, supra). Negative GPR17 modulators may thus represent an excellent treatment option for any neurodegenerative disease associated with demyelination and/or impacted myelination such as e.g. ALS, MSA, Alzheimer's disease, Huntington Disease or Parkinson's Disease.

In a particular preferred aspect, the compounds of the present invention can thus be used in the prevention and/or treatment of a peripheral or central myelination disorder, in particular of a myelination disorder of the central nervous system. In one aspect, the compounds of the present invention are use in the treatment and/or prevention and/or diagnosis of a myelination disorder by oral administration. In a preferred embodiment, the myelination disorder to be treated with the compounds of the present invention is a demyelination disorder.

Examples of such myelination disorders to be treated and/or prevented by the presently disclosed compounds are, in particular, multiple sclerosis (MS) including its various subforms,
neuromyelitis optica (also known as Devic's disease),
chronic relapsing inflammatory optic neuritis, acute disseminated encephalomyelitis,
acute haemorrhagic leucoencephalitis (AHL),
periventricular leukomalacia
demyelination due to viral infections, e.g. by HIV or progressive multifocal leucoencephalopathy,
central pontine and extrapontine myelinolysis,
demyelination due to traumatic brain tissue damage, including compression-induced demyelination, e.g. by tumors
demyelination in response to hypoxia, stroke or ischaemia or other cardiovascular diseases,
demyelination due to exposure to carbon dioxide, cyanide, or other CNS toxins
Schilder's disease,
Balo concentric sclerosis,
Perinatal encephalopathy, and
Neurodegenerative Diseases including, in particular,
Amyotrophic lateral sclerosis (ALS).
Alzheimer's disease (AD).
Multiple system atrophy
Parkinson's Disease Spinocerebellar ataxia (SCA), also known as spinocerebellar atrophy Huntington's Disease psychiatric disorders such as schizophrenia and bipolar disorder (see e.g. Fields, Trends Neurosci 31, 2008, 361; Tkachev et al, Lancet 362, 2003, 798).

peripheral myelination diseases such as leukodystrophies, peripheral demyelinating neuropathies, Dejerine-Sottas syndrome or Charcot-Marie-Tooth disease The treatment or prevention of a CNS disease such as a demyelination disease, also includes the treatment of the signs and symptoms associated with such a disease.

For example, the use of the compounds of the present invention for the treatment and/or prevention of MS also includes the treatment and/or prevention of the signs and symptoms associated with MS such as negative effects on optic nerves (vision loss, double vision), dorsal columns (loss of sensation), corticospinal tract (spastic weakness), cerebellar pathways (incoordination, dysarthria, vertigo, cognitive impairment), medial longitudinal fasciculus (double vision on lateral gaze), spinal trigeminal tract (face numbness or pain), muscle weakness (impaired swallowing, control of the bladder or gut, spasms), or psychological effects associated with the underlying disease such as depression, anxiety or other mood disorders, general weakness or sleeplessness.

Hence, the compounds of the present invention are for use in treating signs and symptoms of a myelination disease, in particular a demyelination disease such as multiple sclerosis; such signs and symptoms of MS include but are not limited to the group of vision loss, vision impairment, double vision, loss or impairment of sensation, weakness such as spastic weakness, motor incoordination, vertigo, cognitive impairment, face numbness, face pain, impaired swallowing, impaired speech, impaired control of bladder and/or gut, spasms, depression, anxiety, mood disorders, sleeplessness, and fatigue.

In one preferred embodiment, the compounds of the present invention are for use in treating multiple sclerosis. MS is a heterogeneous myelination disease and can manifest itself in a variety of different forms and stages, including but not limited to Relapsing-Remitting MS, Secondary-Progressive MS, Primary Progressive MS, Progressive Relapsing MS, each depending on activity and disease progression. Hence, in one embodiment, the compounds of the present invention are for use in treating multiple sclerosis in its various stages and forms, as described herein.

In one aspect, the compounds of the present invention are for use in the treatment/or prevention of Neuromyelitis optica (also known as Devic's disease or Devic's syndrome). Neuromyelitis optica is a complex disorder characterized by inflammation and demyelination of the optic nerve and the spinal cord. Many of the associated symptoms are similar to MS and include muscle weakness, in particular of the limbs, reduced sensation and loss of bladder control.

In one aspect, the compounds of the present invention are for use in prevention and/or treating ALS. ALS has been associated recently with oligodendrocyte degeneration and increased demyelination, suggesting ALS as a target disease for negative GPR17 modulators (Kang et al, supra; Fumagalli et al, Neuropharmacology 104, 2016, 82).

In one aspect, the compounds of the present invention are for use in prevention and/or treating Huntington Disease. Huntington is well described to be associated with impacted myelination, (Bartzokis et al, supra; Huang et al, Neuron 85, 2015, 1212).

In one aspect, the compounds of the present invention are for use in prevention and/or treating multiple system atrophy. MSA was associated strongly with demelination recently (Ettle supra, Jellinger supra) suggesting remyelination strategies to treat or prevent MSA.

In one aspect, the compounds of the present invention are for use in prevention and/or treating Alzheimer's Disease. AD has been recently observed to be associated with increased cell death of oligodendronecytes and focal demyelination and to represent a pathological process in AD (Mitew et al, Acta Neuropathol 119, 2010, 567).

One aspect of the present invention relates to a method of treatment of anyone of the diseases or disorders described herein, in particular of a myelination disease such as MS, Neuromyeltis optica, ALS, Chorea Huntington, Alzheimer's Disease or others, by administering to a subject in need thereof, including a human patient, a therapeutically effective amount of a compound of the present invention.

In another aspect, the compound of the present invention may be used in the prevention and treatment of a spinal cord injury, perinatal encephalopathy, stroke, ischemia, or a cerebrovascular disorder.

In one aspect, the invention relates to a method for the prevention and/or treatment of a syndrome or disorder associated with a myelination disorder, or with a disorder or syndrome associated with a brain tissue damage, which comprises administering to a patient in need thereof a therapeutically effective amount of a compound as described herein. A patient in need of such a treatment can be any patient who suffered brain tissue damage such as by mechanical, chemical, viral, or other trauma.

In one aspect, the invention relates to a method for the prevention and/or treatment of a syndrome or disorder associated with a myelination disorder, or with a disorder or syndrome associated with stroke or other brain ischemia, which comprises administering to a patient in need thereof a therapeutically effective amount of a compound as described herein. A patient in need thereof may be any patient that recently experienced a cerebral ischemia/stroke which may have been caused, for example, by the occlusion of a cerebral artery either by an embolus or by local thrombosis.

GPR17 has been also associated with food uptake, insulin control and obesity recently. According to various reports, negative modulators of GPR17 may be helpful for controlling food uptake and for treating obesity (see e.g. Ren et al, Diabetes 64, 2015; 3670.) Hence, one embodiment of the present invention relates to the use of the compounds herein for the prevention and/or treatment of obesity, and methods of treating obesity.

Moreover, the compounds of the present invention may be used for the treatment of prevention of tissues where GPR17 is expressed, such as e.g. heart, lung or kidney. In one embodiment, the compounds of the present invention can be used to treat or prevent ischaemic disorders of the kidney and/or the heart.

GPR17 has been also associated with pulmonary inflammation and asthma such as, for example, induced by house dust mite (Maekawa, J Immunol 2010, 185(3), 1846-1854).

Hence, the compounds of the present invention may be used for the treatment of asthma or other pulmonary inflammation.

The treatment according to the present invention may comprise the administration of one of the presently disclosed compounds as "stand alone" treatment of a CNS disease, in particular of a myelination disease or disorder such as MS or ALS. Alternatively, a compound disclosed herein may be administered together with other useful drugs in a combination therapy.

In a non-limiting example, a compound according to the present invention is combined with another medicament for treating a myelination disease, such as MS, having a different mode of action, such as e.g. an anti-inflammatory or immunosuppressive drug. Such compounds include but are not limited to: (i) corticosteroids such as prednisone, methylprednison or dexamethasone, (ii) beta interferons such as interferon beta-1a, interferon beta-1b or peginterferon beta-1a, (iii) anti-CD20 antibodies such as ocrelizumab rituximab and ofatumumab, (iv) glatiramer salts such as glatiramer acetate, (v) dimethyl fumarate, (vi) fingolimod and other sphingosine-1-phosphate receptor modulators such as ponesimod, siponimod, ozanimod or laquinimod, (vii) dihydroorotate dehydrogenase inhibitors such as teriflunomide or leflunomide, (viii) anti-integrin alpha4 antibodies such as natalizumab, (ix) anti CD52 antibodies such as alemtuzumab, (x) mitoxantrone, (xi) anti Lingol antibodies such as opicinumab, or (xii) other immunomodulatory therapies such as masitinib.

Likewise, a compound of the present invention can be combined with an analgesic drug if a painful myelination condition is to be treated. Also, a compound of the present disclosure may be used in combination with an antidepressant to co-treat psychological effects associated with the underlying myelination disease to be treated.

In combination therapies the two or more active principles may be provided via the same Formulation or as a "kit of parts", i.e. in separate galenic units. Also, the two or more active principles, including the compounds of the present invention, may be administered to the patient at the same time or subsequently, e.g. in an interval therapy. The additional drug may be administered by the same mode or a different mode of administration. For example, the GPR17 modulator of the present invention may be administered orally, while the second medicament may be administered by subcutaneous injection.

In one aspect, the compounds of the present invention may be used for the diagnosis and/or monitoring of a GPR17-related disease, as further described herein, in particular of a demyelinating disease, as disclosed herein, preferably in the diagnosis and monitoring of multiple sclerosis.

In one aspect, the compounds of the present invention can be used to diagnose and/or monitor the expression, distribution and/or activation of the GPR17 receptor either in-vivo, e.g. directly in a subject, such as using molecular imaging techniques, or in-vitro, such as e.g. by examining any samples such as body fluids or tissues taken from a subject. Any such determination of the GPR17 activity, expression and/or distribution may be used to predict, diagnose and/or monitor (a) the status and progression of a GPR17-associated disease as described herein, in particular a myelination disease including but not limited to, for example, multiple sclerosis, and (b) the efficacy and/or applicability and/or proper dosing of a treatment associated with any such GPR17-associated disease.

In one aspect, the compounds of the present invention may be used as PET or SPECT tracers, as further disclosed herein, in order to perform in-vivo diagnosis and/or disease monitoring. By this, the expression, activation and/or distribution of the GPR17 receptor may be directly measured in a subject, e.g. by imaging of a human patient after the administration of a GPR17 PET or SPECT tracer of the present invention. This may facilitate a proper diagnosis of the disease, can help to determine applicable treatment options and/or may be used to monitor disease progression and/or to monitor or predict the success of a medical intervention, including the selection and proper administration and/or dosing of a therapeutic drug.

In one embodiment, the PET or SPECT tracers of the present invention may be used in conjunction with a therapeutic drug, i.e. as a Companion Diagnostic, in order to monitor and/or predict the efficacy and/or safety of said therapeutic drug in a particular subject, or to estimate a drug's proper dosage.

One embodiment relates to a PET or SPECT tracer of the present invention for use as a Companion Drug in conjunction with a therapeutic drug. The therapeutic drug to be used with the PET or SPECT tracer of the present invention may be selected from the group of (a) an unlabelled compound of the present invention, (b) a GPR17 modulating compound which is different from the compounds of the present invention and (c) a drug for the treatment of a myelination disease, including but not limited to a drug for use in multiple sclerosis treatment which is not a GPR17 modulator, as further described herein.

One embodiment relates to a kit comprising
(a) as a first component, a PET or SPECT tracer of the present invention, in particular a PET or PET tracer based on a compounds of the present invention, but having incorporated at least one radionuclide which is suitable for PET or SPECT imaging, preferably a radionuclide selected from $^{18}$F, $^{11}$C, $^{123}$I, $^{125}$I and $^{131}$I,
(b) as a second component, a therapeutic drug selected from among
  i. a compound of the present invention as further defined herein, and having no radionuclide incorporated,
  ii. a GPR17 modulating compound which is different from the compounds of the present invention, and
  iii. a drug for the treatment of a myelination disease, including but not limited to a drug for use in multiple sclerosis treatment, but having no GPR17 modulating activity; such compounds are known to a person skilled in the art including those examples further described above.

Alternatively, the compounds of the present invention may be used in an in-vitro diagnostic assay, for example for the examination of suitable body fluids of a subject such as e.g. blood, plasma, urine, saliva, or cerebrospinal fluid for any level of GPR17 expression, activity and/or distribution.

One embodiment relates to a method of treating a GPR17 associated disease, in particular a myelination disease including but not limited to multiple sclerosis, wherein said method includes the steps of (a) determining the expression, activity and/or distribution of the GPR17 receptor of a subject, (b) comparing the expression, activity and/or distribution of the GPR17 receptor in said subject with the expression, activity and/or distribution of the GPR17 receptor in one or more healthy subjects or a population, (c) determining the need for medical treatment or prophylaxis of said subject based on a deviation of expression, activity and/or distribution of GPR17 of said subject from healthy subjects or a population and (d) treating the subject with the deviation of expression, activity and/or distribution of the GPR17 receptor by administering a therapeutic drug to said individual, which drug is suitable for the treatment of GPR17 associated diseases or disorders, in particular by administering a GPR17 modulator, preferably by administering one of more of the compounds of the present invention. In one embodiment, the determination (a) of the GPR17 expression, activity and/or distribution will be conducted using one of the compounds of the present invention, in particular with a PET or SPECT tracer, or by an in vitro examination of body fluids or tissue of said subject using a PET or SPECT tracer of the present invention.

In one preferred aspect, the invention relates to a pharmaceutical composition comprising a compound as described herein, and a pharmaceutical acceptable carrier.

For the administration as a medicinal drug, the compounds may be used in pharmaceutical composition comprising a compound of the present disclosure, and a pharmaceutically acceptable carrier, as further defined herein. Such a pharmaceutical composition can be adapted for example for oral, intravenous, intramuscular, subcutaneous, nasal, rectal, transcranial, buccal or transdermal administration and may comprise pharmaceutically acceptable carriers, adjuvants, diluents, stabilizers and the like.

For instance, the compounds of the present invention may be dissolved in oils, propylene glycol or other solvents which are commonly used to produce an injection. Suitable examples of the carriers include, but not limited to, physiological saline, polyethylene glycol, ethanol, vegetable oils, isopropyl myristate, etc. The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

In one embodiment, the compounds of the present invention may be administered orally, e.g. in the form of a tablet, a capsule, a drage', a powder, a granulate, or in form of a liquid or a semi-solid, including e.g. syrups, suspensions, emulsions or solutions, by way of non-limiting example.

Oral formulations may contain, without limitation, sustained release agents, disintegrants, fillers, lubricants, stabilizers, antioxidants, flavours, dispersion agents, electrolytes, buffers, dyes, or conservation agents. Suitable excipients and formulations are known to those skilled in the art and are disclosed in standard monographs, such as Remington ("The science and practice of pharmacy", Lippincott, Williams & Wilkins, 2000) or disclosed in other sources well known to persons skilled in the art.

A tablet can, for example, be prepared by mixing at least one compound of the present invention with at least one non-toxic pharmaceutically acceptable excipient, such as e.g. binder, filler/diluents, disintegrant agents, plastisizer, and the like, and an optional solvent (aqueous or non aqueous), and by subsequent processing the mixture to a tablet by a process including but not limited to dry compression, dry granulation, wet granulation, spray drying, or melt extrusion. A tablet can either be uncoated, or coated by known techniques to either mask the bad taste of an unpleasant tasting drug, or delay disintegration and absorption of the active ingredient in the gastrointestinal tract. A tablet may provide an immediate release or sustained release of the compounds of the present invention.

Typical sustained release agents are for example those that swell upon contact with water such as polyvinylpyrrolidone, hydroxyethylcellulose, hydroxypropylcellulose, other cellulose ethers, starch, pregelatinised starch, polymethacrylate, polyvinylacetate, microcrystalline cellulose, dextrans, and mixtures of these. Non-limiting examples of disintegrants include pregelatinised starch, sodium starch glycolate, microcrystalline cellulose, carboxymethylcellulose sodium (CMC-Na), cross-linked CMC-Na, and low-substituted hydroxypropylcellulose, as well as mixtures thereof. Suitable fillers and binders include without limitation microcrystalline cellulose, powdered cellulose, lactose (anhydrous or monohydrate), compressible sugar, starch (e.g. corn starch or potato starch), pregelatinised starch, fructose, sucrose, dextrose, dextrans, other sugars such as mannitol, maltitol, sorbitol, lactitol and saccharose, siliconised microcrystalline cellulose, calcium hydrogen phosphate, calcium hydrogen phosphate dihydrate, dicalciumphosphate dihydrate, tricalciumphophate, calcium lactate or mixtures thereof. Lubricants, antiadherents and/or glidants include stearic acid, magnesium stearate, calcium stearate, sodium lauryl sulphate, hydrogenated vegetable oil, hydrogenated castor oil, sodium stearyl fumarate, macrogols, glycerol dibehenate, talc, corn starch, silicon dioxide, and the like, including mixtures.

The compound of the present invention may also be formulated for parenteral administration by injection, e.g. by bolus injection or infusion. The compositions for injection may be provided ready to use and may take such forms as suspensions, solutions, or emulsions in oily or aqueous vehicles, and may contain excipients such as suspending, stabilising, preserving and/or dispersing agents. Alternatively, the active ingredient may be in powder form for constitution with a suitable vehicle, e.g. sterile pyrogen-free water or saline, before use.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

In one embodiment, the compounds may be administered transdermally. This mode of administration prevents the so-called $1^{st}$ pass effect of oral administration and moreover allows providing more constant plasma levels which is of particular advantage in some instances. The design of transdermal forms such as ointments or creams or other transdermal systems such as e.g. patches or electrophoretic devices is generally known from the art, see e.g. Venkatraman and Gale, Biomaterials 1998, Vol 19, p1119; Prausnitz and Langer, Nat Biotechnology 2008, Vol 26.11 p1261; WO 2001/47503; WO2009/000262; WO99/49852; WO 07/094876.

The preferable dose level of the compounds according to the present invention depends upon a variety of factors including the condition and body weight of the patient, severity of the particular disease, dosage form, and route and period of administration, but may appropriately be chosen by those skilled in the art. In various embodiments, the compounds are administered in an amount ranging from 0.001 to 10 mg/kg of body weight per day, or from 0.03 to 1 mg/kg of body weight per day. Individual doses may range from about 0.1 to 1000 mg of active ingredient per day, from about 0.2 to 750 mg/day, from about 0.3 to 500 mg/day, from 0.5 to 300 mg/day, or from 1 to 100 mg/day. Doses may be administered once a day, or several times a day with each divided portions.

Another aspect of the present invention is a Kit comprising a medicine or a pharmaceutical composition as described herein, and instructions for its use.

Definitions

The compounds of the present invention include the compounds encompassed by Formulae I, Ia, Ib, Ic, IIa, IIb, IIc, IIIa, IIIb, IIIc, IVa, IVb and IVc as further described herein as well as the final individual compounds disclosed in the description and the experimental section.

Any reference to a compound according to the present invention also includes pharmaceutically acceptable salts, solvates, isotopes and co-crystals of such compounds unless expressly indicated otherwise.

The term "pharmaceutically acceptable salts" relates to any salts that the compounds may form and which are suitable for administration to subjects, in particular human subjects, according to the present invention. Such salts include but are not limited to acid addition salts, formed either with inorganic acids such as hydrochloric acid, hydrobromic acid, sulfuric acid, nitric acid, phosphoric acid, and the like, or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]oct-2-ene-1-6arboxyic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. Other salts include 2,2-dichloroacetate, adipate, alginate, ascorbate, aspartate, 2-acetamidobenzoate, caproate, caprate, camphorate, cyclamate, laurylsulfate, edisilate, esylate, isethionate, formate, galactarate, gentisate, gluceptate, glucuronate, oxoglutarate, hippurate, lactobionate, napadisilate, xinafoate, nicotinate, oleate, orotate, oxalate, palmitate, embonate, pidolate, p-aminosalicylate, sebacate, tannate, rhodanide, undecylenate, and the like; or salts formed when an acidic proton present in the parent compound is replaced, such as with ammonia, arginine, benethamine, benzathine, calcium, choline, deanol, diethanolamine, diethylamine, ethanolamine, ethylendiamine, meglumine, glycine, hydrabamine, imidazole, lysine, magnesium, hydroxyethylmorpholine, piperazine, potassium, epolamine, sodium, trolamine, tromethamine or zinc.

The present invention includes within its scope solvates of the compounds as defined herein. "Solvates" are crystals formed by an active compound and a second component (solvent) which, in isolated form, is liquid at room temperature. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds herein may be formed with water, in which case they will be hydrates.

The present invention also includes co-crystals within its scope. The term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity. Examples of co-crystal formers, which may be present in the co-crystal alongside the active pharmaceutical ingredient, include L-ascorbic acid, citric acid, glutaric acid, cinnamic acid, mandelic acid, urea and nicotinamide.

The invention also includes all suitable isotopic variations of a compound of the invention. An "isotopic variation", or shortly "isotope" of a compound of the invention is defined as one in which at least one atom is replaced by an atom having the same atomic number but an atomic mass different from the atomic mass usually found in nature with the most abundant isotope(s) being preferred. Examples of isotopes that can be incorporated into compounds of the invention include isotopes of hydrogen, carbon, nitrogen, oxygen, sulphur, fluorine and chlorine such as $^2$H, $^3$H, $^{11}$C, $^{13}$C, $^{14}$C, $^{15}$N, $^{17}$O, $^{18}$O, $^{35}$S, $^{18}$F, and $^{36}$Cl, respectively. Certain isotopic variations of the invention, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life, reduced dosage requirements and hence may be preferred in some circumstances. Isotopic variations of the compounds of the invention can generally be prepared by conventional procedures using appropriate isotopic variations of suitable reagents.

Also part of the invention are those compounds wherein at least one atom has been replaced by a radioactive isotope (radioisotope) of the same or a different atom that can be used in vivo imaging techniques such as single-photon emission computed tomography (SPECT) or positron emission tomography (PET).

Examples for such isotopic variations of GPR17 modulators usable in SPECT studies (such compounds herein "SPECT tracers") are compounds wherein a $^{99m}$Tc, $^{111}$In, $^{82}$Rb, $^{137}$Cs, $^{123}$I, $^{125}$I, $^{131}$I, $^{67}$Ga, $^{192}$Ir or $^{201}$Tl, and preferably $^{123}$I has been introduced. For example, in order for the compounds of the present invention to be used as SPECT tracers, an $^{123}$I isotope may be introduced into a GPR17 modulator as disclosed herein. By way of a non-limiting example, in order for a compound to be used as SPECT tracer, a radionuclide selected from $^{123}$I, $^{125}$I and $^{131}$I may be introduced into a compound of the present invention. In one embodiment, a SPECT tracer of the present invention may be based on the structure of a halogen-containing GPR17 modulator disclosed herein, wherein one of the radionuclides $^{123}$I, $^{125}$I and $^{131}$I has been introduced into the position of a halogen, preferably, a iodine atom.

Accordingly, the term "SPECT tracer of the present invention", relates to compounds as described in the present patent application and having a structure according to anyone of compounds of the present invention as further defined herein, wherein at least one radioisotope has been introduced which is suitable for SPECT imaging. This includes but is not limited to $^{99m}$Tc, $^{111}$In, $^{82}$Rb, $^{137}$Cs, $^{123}$I, $^{125}$I, $^{131}$I, $^{67}$Ga, $^{192}$IR or $^{201}$Tl.

Examples for GPR17 modulator derivatives usable in PET applications (herein "PET tracers") are compounds wherein $^{11}$C, $^{13}$N, $^{15}$O, $^{18}$F, $^{76}$Br or $^{124}$I have been introduced. For example, in order for a compound to be used as a PET tracer, an $^{18}$F isotope may be introduced into a compound of the present invention. In one embodiment, a PET tracer may be based on the structure of a fluorine-containing GPR17 modulator disclosed herein, wherein the respective radionuclide $^{18}$F has been introduced into the position of the fluorine atom. This likewise applies to the introduction of at least one $^{11}$C, $^{13}$N, $^{15}$O, $^{76}$Br or $^{124}$I, instead of an "unlabelled" carbon, nitrogen, oxygen, bromine, or iodine atom, respectively. (see e.g. Pimlott and Sutherland, Chem Soc Rev 2011, 40, 149; van der Born et al, Chem Soc Rev 2017, 46, 4709).

Accordingly, the term "PET tracer of the present invention", relates to compounds of the present invention as further defined herein, wherein at least one radioisotope has been introduced which is suitable for PET imaging. This includes but is not limited to $^{11}$C, $^{13}$N, $^{15}$O, $^{18}$F, $^{76}$Br or $^{124}$I.

The present invention includes within its scope prodrugs of the compounds of the present invention. In general, such prodrugs will be functional derivatives of the compounds described herein which are readily convertible in vivo, e.g. by endogenous enzymes in the gut or the blood, into the required GPR17 modulating compounds described herein. Conventional procedures for the selection and preparation of suitable prodrug derivatives are described, for example, in Design of Prodrugs, ed. H. Bundgaard, Elsevier, 1985.

Depending on its substitution pattern, the compounds of the present invention may or may not have one or more optical stereocenters, and may or may not exist as different enantiomers or diastereomers. Any such enantiomers, diastereomers or other optical isomers are encompassed by the scope of the invention.

The compound of the present invention may also exist in different crystal forms, i.e. as polymorphs, all of which are encompassed by the present invention.

The compounds of the present invention may be included in a pharmaceutical composition which may also include a pharmaceutically acceptable carrier. "Pharmaceutically acceptable carrier" refers to a diluent, adjuvant, excipient, or carrier, or other ingredient with which a compound of the invention is administered and which a person of skilled in the art would understand to be pharmaceutically acceptable.

The compounds of the present invention are useful in the prevention and/or treatment of certain diseases or disorders in animals, in particular in humans, as described herein.

"Preventing" or "prevention" refers to a reduction in risk of acquiring a disease or disorder (i. e., causing at least one of the clinical symptoms of the disease not to develop in a subject, in particular a human subject, that may be exposed to or predisposed to the disease but does not yet experience or display symptoms of the disease).

"Treating" or "treatment" of any disease or disorder includes, in one embodiment, to improve the disease or disorder (i. e., arresting or reducing the development of the disease or at least reducing one of the clinical symptoms of the disease). In another embodiment "treating" or "treatment" refers to improve at least one physical parameter, which may or may not be discernible by the subject, in particular a human subject, but which is based on or associated with the disease or disorder to be treated. In yet another embodiment, "treating" or "treatment" refers to modulating or alleviating the disease or disorder, either physically (e. g. stabilization of a discernible on non-discernible symptom), physiologically (e. g. stabilization of a physiological parameter), or both. In yet another embodiment, "treating" or "treatment" refers to delaying the onset or progression of the disease or disorder. Accordingly, "treating" or "treatment" includes any causal treatment of the underlying disease or disorder (i.e. disease modification), as well as any treatment of signs and symptoms of the disease or disorder (whether with or without disease modification), as well as any alleviation or amelioration of the disease or disorder, or its signs and symptoms.

"Diagnosis", "diagnoses" or "diagnosing" of a disease or disorder include, in one embodiment, the identification and measurement of signs and symptoms which are associated with said disease. "Diagnosis", "diagnoses" or "diagnosing" include but are not limited to the detection and/or measurement of decreased, increased, or otherwise incorrectly (e.g. as to time or place) expressed, activated, or distributed GPR17 receptors as indicator of a GPR17-related disease or disorder, as compared to healthy subjects. In one example, GPR17 ligands may be used in the form of PET or SPECT tracers for such a diagnosis, including a diagnosis for a myelination disease.

The terms "disease(s)" and "disorder(s)" are used largely interchangeably herein.

"Monitoring" refers to the observation of a disease, condition or at least one medical parameter over a certain period of time. "Monitoring" also includes the observations of the effects of a therapeutic drug with the assistance of a "Companion Drug".

"Companion Diagnostic" as used herein refers to a compound that can be used in conjunction to a therapeutic drug with the aim to determine the applicability (e.g. in terms of safety and efficacy) of said therapeutic drug to a specific patient. The use of a "Companion Diagnostic" may include diagnostic and monitoring steps.

The term "animal(s)" and "subject(s)" includes humans. The terms "human," "patient" and "human subject" are typically used interchangeably herein, unless clearly indicated. The invention also relates to methods of treating an animal disease or disorder, as described in more detail herein, in particular a human disease or disorder, which includes the administration of the compounds of the present invention in therapeutically effective amounts.

"Therapeutically effective amount" means the amount of a compound that, when administered to a subject, in particular a human subject, for treating a disease, is sufficient to effect such treatment for the disease. The "therapeutically effective amount" can vary depending on the compound, the disease and its severity, and the condition, age, weight, gender etc. of the subject, in particular a human subject, to be treated.

The term "multiple sclerosis" as used herein refers to the disease as classified in Section G35 of the ICD-10-CM diagnosis code of the 2018 American edition.

The term "GPR17 modulators" as used herein are meant to describe compounds that are capable of modulating the activity of the GPR17 receptor, in particular compounds that are capable of decreasing the GPR17 activity. Such "negative GPR17 modulators" include GPR17 antagonists which are capable of blocking the effects of GPR17 agonists, as well as GPR17 inverse agonists which are also capable of inhibiting constitutional active GPR17 receptors or receptor variants. Preferred GPR17 modulators of the present invention are inverse GPR17 agonists.

The term "fluoromethyl" as used refers to a methyl group, which is substituted with one ("monotluoromethy"), two (difluoromethyl) or three ("trifluoromethyl") fluorine atoms. A particularly preferred fluoroalkyl group is difluoromethyl: —$CHF_2$.

The term "fluoromethoxy" as used refers to a methoxy group, which is substituted with one ("monofluoromethoxy"), two ("difluoromethoxy") or three ("trifluoromethoxy") fluorine atoms. An example of a fluoroalkoxy group is trifluoromethoxy —$OCHF_3$.

The term "cyclopropyt" as used herein refers to a monovalent group derived from a cyclic saturated hydrocarbon with three ringforming carbon atoms, which may be unsubstituted or substituted with one or more substituents as further indicated herein.

EXPERIMENTAL PART

A. Chemistry

The compounds of the present invention and their synthetic routes are described in more details below.

A-I General Methods of Making the Compounds

The compounds of Formula I according to the invention can be prepared analogously to conventional methods as understood by the person skilled in the art of synthetic organic chemistry.

A-I General Methods of Making the Compounds

The compounds of Formula I according to the invention can be prepared analogously to conventional methods as understood by the person skilled in the art of synthetic organic chemistry.

Any reference to the synthesis of compounds of general Formula I herein likewise apply to the applicable compounds of the subgeneric Formula Ia, Ib, Ic, IIa, IIb, IIc, IIIa, IIIb, IIIc, IVa, IVb and IVc, and the specific Example compounds disclosed herein.

According to one embodiment, some compounds of general Formula I may be prepared by reaction of a sulfonyl chloride of Formula XII with an aniline of Formula X according to the equation:

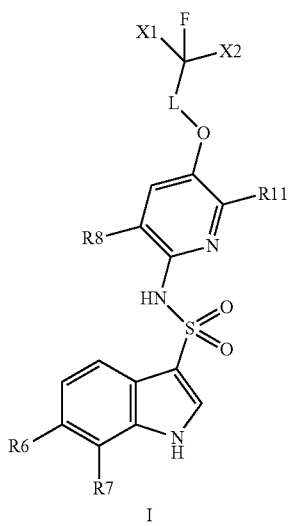

I

This reaction may be performed in the presence of a base such as pyridine used as solvent at room temperature or by heating at a temperature ranging from 60 to 100° C., possibly in the presence of a catalytic amount of dimethylaminopyridine.

Alternatively, some compounds of general Formula I may be prepared by in situ deprotection of a compound of Formula I-P wherein P is a protecting group such as phenylsulfonyl ($PhSO_2$) according to the equation:

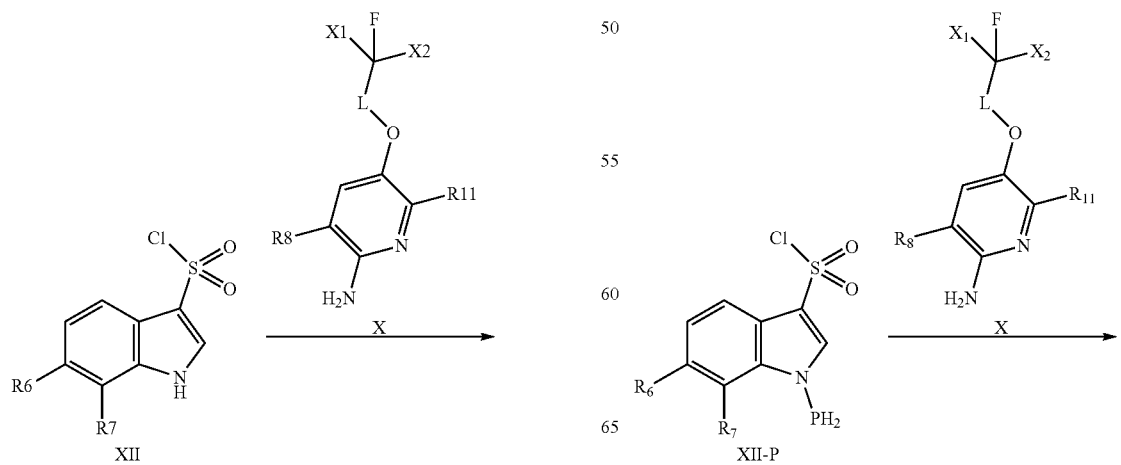

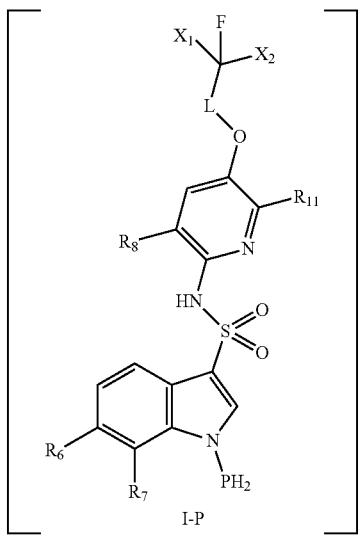

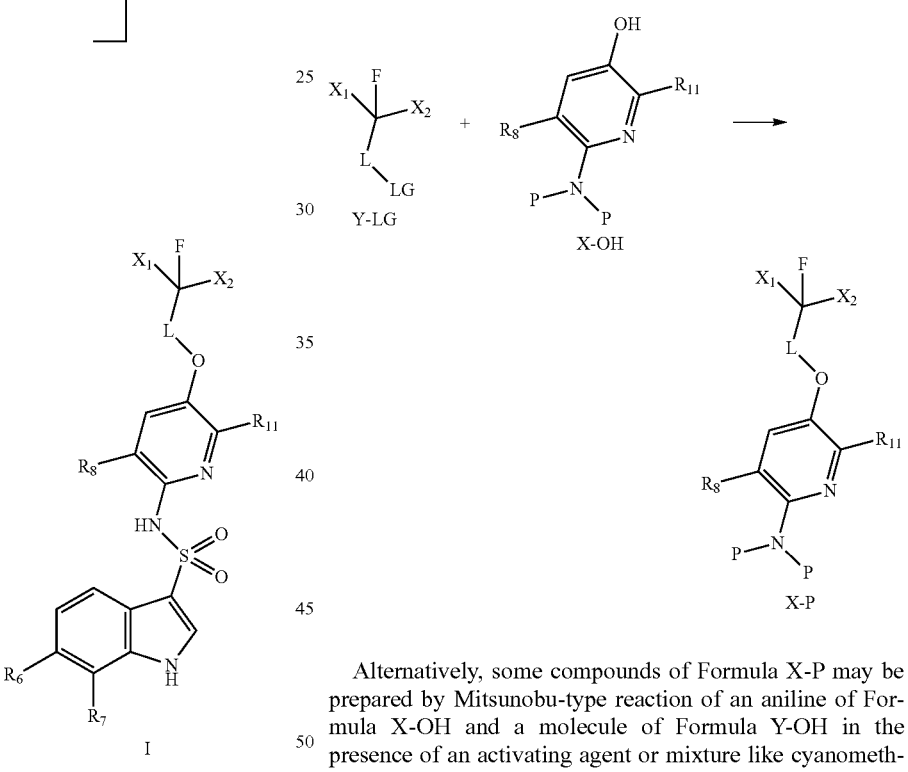

Some compounds of Formula X-P may be prepared by reaction of an aniline of Formula X-OH and a molecule of Formula Y-LG where LG is a leaving group such as bromine, in the presence of a base like $K_2CO_3$ or KOH in a polar solvent such as DMF or ACN.

Compounds of Formula I-P may be prepared by reaction of a sulfonyl chloride of Formula XII-P with an aniline of Formula X. This reaction may be performed in the presence of a base such as pyridine used as solvent at room temperature or by heating at a temperature ranging from 60 to 100° C.

Some compounds of Formula X may be prepared by deprotection of a compound of Formula X-P wherein P is a protecting group such as p-methoxybenzyl (PMB) using acidic conditions like pure trifluoroacetic acid or with a solvent like dichloromethane. Other deprotection conditions may as well be using a reducing agent like hydrogen in the presence of a catalyst like palladium or palladium hydroxide possibly activated on carbon in a solvent like methanol.

Alternatively, some compounds of Formula X-P may be prepared by Mitsunobu-type reaction of an aniline of Formula X-OH and a molecule of Formula Y-OH in the presence of an activating agent or mixture like cyanomethylenetributylphosphorane (CMBP) or triphenylphosphine and diisopropyl azodicarboxylate (DIAD) in a solvent such as Toluene or THF under heating at temperature ranging from 60° C. to 120° C.

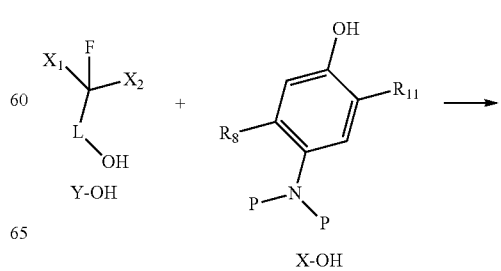

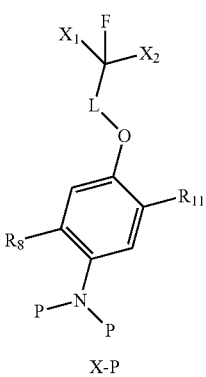

Anilines of Formula X-OH may be prepared according to any method known to the person skilled in the art or using procedures described in literature.

Compounds of Formula XII may be prepared by chlorosulfonylation of a compound of Formula XI according to the equation:

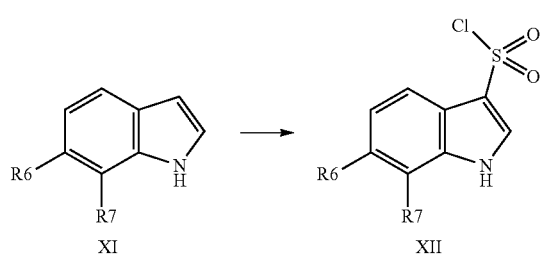

This reaction may be performed in the presence of a sulfonylating agent such as chlorosulfonic acid in a polar solvent such as acetonitrile at room temperature.

Similarly, compounds of Formula XII-P wherein P is a protecting group such as phenylsulfonyl may be prepared by chlorosulfonylation of a compound of Formula XI-P according to the equation:

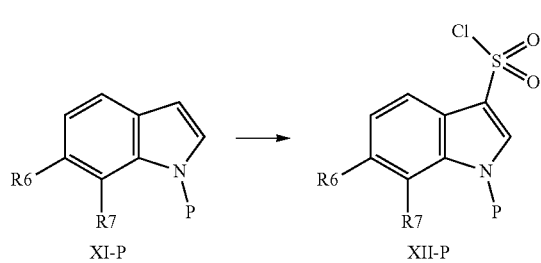

This reaction may be performed in the presence of chlorosulfonic acid in a polar solvent such as acetonitrile at room temperature.

Compounds of Formula XI-P wherein P is a protecting group such as phenylsulfonyl may be prepared by protection of a compound of Formula XI according to the equation:

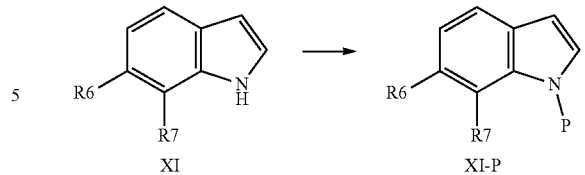

This reaction may be performed according to any method known to the person skilled in the art.

Compounds of Formula XI may be prepared by suitable methods well known by the person skilled in the art.

Alternatively, some compounds of Formula XI may be prepared by reaction of a ortho-substituted nitroarene XII with a vinyl Grignard reagent XIII (Bartoli indole synthesis) according to the equation:

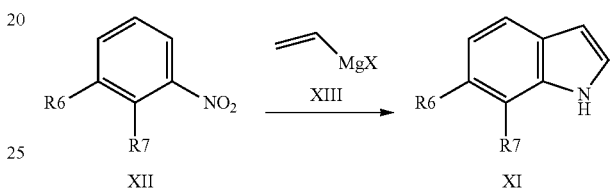

This reaction may be performed using a vinyl Grignard reagent such as vinyl magnesium bromide in a polar solvent such as tetrahydrofuran at low temperature ranging from −20° C. to −78° C.

Alternatively, some compounds having the general Formula I may be prepared by functional group conversion on already assembled analogs of compounds having the general Formula I using procedures described in the literature or known to the person skilled in the art.

In particular, some compounds of Formula I wherein R7 is a cyclopropyl group may be prepared by Suzuki-type coupling starting from a compound of Formula I wherein R7 is a halogen atom, preferentially bromine, in the presence of the corresponding boronic acid, a palladium salt such as palladium acetate, a phosphine such as tricyclohexylphosphine and a base such as tripotassium phosphate in a solvent such as toluene according to methods known to the person skilled in the art.

A-II. Abbreviations/Recurrent Reacients
Ac: acetyl
ACN: Acetonitrile
Brine: Saturated aqueous sodium chloride solution
nBu: n-butyl
tBu: tert-butyl
CMBP: Cyanomethylenetributylphosphorane
Cy: Cyclohexyl
DAST: Diethylaminosulfur fluoride
DCM: Dichloromethane
DIAD: Diisopropylazodicarboxylate
DMAC: N,N-dimethylacetamide
DMAP: 4-dimethylaminopyridine
DMF: N,N-Dimethylformamide
DMSO: Dimethylsulfoxide
dppf: 1,1'-bis(diphenylphosphino)ferrocene
ES+: Electrospray Positive Ionization
ES−: Electrospray Negative Ionization
ESI: Electrospray Ionization
EtOAc: Ethyl acetate
h: Hour LC: Liquid Chromatography
LCMS: Liquid Chromatography Mass Spectrometry
Me: Methyl
MeOH: Methanol
min.: minutes
mw: microwave oven
NBS: N-Bromosuccinimide
NMR: Nuclear magnetic resonance
Pin: pinacolato
PMB: para-methoxybenzyl
rt: room temperature
TBAHSA: Tetrabutylammonium hydrogen sulfate
TFA: Trifluoroacetic acid
THF: Tetrahydrofuran
TLC: Thin Layer Chromatography A-III. Analytical Methods Commercial solvents and reagents were generally used without further purification, including anhydrous solvents when appropriate (generally Sure-Seal™ products from Aldrich Chemical Company or AcroSeal™ from ACROS Organics). In general reactions were followed by thin layer chromatography or Liquid Chromatography Mass Spectrometry analyses.

Mass spectrometric measurements in LCMS mode are performed using different methods and instruments as follows:

Basic LCMS Method 1:

A QDA Waters simple quadrupole mass spectrometer is used for LCMS analysis. This spectrometer is equipped with an ESI source and an UPLC Acquity Hclass with diode array detector (200 to 400 nm). Data are acquired in a full MS scan from m/z 70 to 800 in positive/negative mode with a basic elution. The reverse phase separation is carried out at on a Waters Acquity UPLC BEH C18 1.7 μm (2.1×50 mm) column for basic elution. Gradient elution is done with water/ACN/ammonium formate (95/5/63 mg/L) (solvent A) and ACN/water/ammonium formate (95/5/63 mg/L) (solvent B) according to table 1. Injection volume: 1 μL. Full flow in MS.

TABLE 1

| Time (min) | A (%) | B (%) | Flow (mL/min) |
|---|---|---|---|
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |
| 4.1 | 99 | 1 | 0.4 |
| 4.8 | 99 | 1 | 0.4 |

Basic LCMS Method 2:

Mass spectrometry (MS) spectra were recorded on an LCMS-2010EV mass spectrometer (Shimadzu) with electrospray ionization (ESI) coupled to an HPLC modular Prominence (Shimadzu) using Xbridge C18-2.1×30 mm, 2.5 μm (Waters) column. A volume of 3 μL of sample solution with a concentration of approx. 1 mg/mL was injected. The mobile phase for basic conditions was a mixture of A) 5 mM ammonium formate+0.1% ammonia in water B) 5% mobile phase A+0.1% ammonia in acetonitrile. The gradient used was as follows-5:95 (B/A) to 95:5 (B/A) in 4 min and hold 95:5 (B/A) for next 1 min.

Neutral LCMS Method 3:

Mass spectrometry (MS) spectra were recorded on an LCMS instrument (Applied Biosystems API 2000 LC/MS/MS, HPLC Agilent 1100) using the following procedure: dissolving of the compounds at a concentration of 1.0 mg mL-1 in ACN (Solvent A) or water (containing 2 mM ammonium acetate): MeOH 90:10 (Solvent B), and if necessary sonicated until completely dissolved. Then, 10 μL of the solution was injected into a Phenomenex Luna C18 HPLC column (50×2.00 mm, particle size 3 μm) and elution was performed with a gradient of water:ACN (Gradient A) or water:MeOH (Gradient B) from 90:10 to 0:100 within 10 min, starting the gradient after 1 min, followed by elution in pure organic solvent for 10 min at a flow rate of 300 μL min-1. UV absorption was detected from 220 to 400 nm using a diode array detector (DAD).

Acidic LCMS Method 4:

HPLC-MS was performed on an Agilent 1200-6120 LC-MS system coupled to UV Detection (230 to 400 nm and 215 nm) and Mass Spec Detection Agilent 6120 Mass Spectrometer (ES) m/z 120 to 800 using an X-Bridge C18 Waters 2.1×20 mm, 2.5 μM column. Elution was performed with a gradient depicted in Table 2 of Mobile Phase A (10 mM Ammonium formate in water+0.1% Formic acid) and Mobile Phase B (Acetonitrile+5% water+0.1% Formic acid) with a flow rate of 1 mL/min

TABLE 2

| Time (min) | A (%) | B (%) |
|---|---|---|
| 0 | 94 | 6 |
| 1.5 | 5 | 95 |
| 2.25 | 5 | 95 |
| 2.50 | 94 | 6 |

Crude materials could be purified by normal phase chromatography, (acidic or basic) reverse phase chromatography or recrystallization.

Normal phase chromatography was performed using silica gel columns (100:200 mesh silica gel or cartridges for flash chromatography systems such as Isolera™ Four from Biotage® or Teledyne Isco CombiFlash®).

Preparative reverse phase chromatography was performed with two different instruments and according to the methods as follows:

Basic prep LCMS Method 1:

LCMS purification is using an SQD or QM Waters single quadrupole mass spectrometer for MS detection. This spectrometer is equipped with an ESI source, Waters 2525 binary pump coupled with 2767 sample Manager and with a diode array detector (210 to 400 nm).

MS parameters: ESI capillary voltage 3 kV. Cone and Extractor voltage 10. Source block temperature 120° C. Desolvation temperature 300° C. Cone gaz flow 30 L/h (Nitrogen), Desolvation Gas flow 650 L/h. Data are acquired in a full MS scan from m/z 100 to 850 in positive/negative mode.

LC parameters: The reverse phase separation is carried out at rt on an XBridge prep OBD C18 column (5 μm, 30×50 mm). Gradient elution is done with solvent A1 ($H_2O$+ $NH_4HCO_3$ 10 mM+50 μl/L $NH_4OH$) and solvent B1 (100% ACN) (pH ~8.5). HPLC flow rate: 35 ml/min to 45 ml/min, injection volume: 990 μl. The splitting ratio is set at +/−1/6000 to MS (table 3).

TABLE 3

| Time (min) | A1 (%) | B1 (%) | Flow (mL/min) |
|---|---|---|---|
| 0 | 95 | 5 | 35 |
| 1 | 95 | 5 | 35 |
| 7 | 10 | 90 | 35 |
| 7.5 | 5 | 95 | 35 |
| 9 | 5 | 95 | 35 |
| 9.1 | 5 | 95 | 45 |
| 12 | 5 | 95 | 45 |

Neutral RP—HPLC Method 2:

HPLC purification of final products was performed on a Knauer Smartline 1050 HPLC system using a RP-HPLC column (Knauer 20 mm i.d., Eurospher-100 C18). The product was dissolved in methanol (20 mg per 8 mL) and subjected to reversed-phase HPLC applying a gradient of methanol/water (70:30 to 100:0 over 24 min).

NMR spectra were recorded on different instruments:
- a BRUKER AVANCEIII 400 MHz-Ultrashield NMR Spectrometer fitted with a Windows 7 Professional workstation running Topspin 3.2 software and a 5 mm Double Resonance Broadband Probe (PABBI 1H/19F-BB Z-GRD Z82021/0075) or a 1 mm Triple Resonance Probe (PATXI 1H/D-13C/15N Z-GRD Z868301/004).
- a Varian 400 MHz NMR spectrometer with acquisition time (at)=2.0 sec, relaxation delay (d1)=2.0 sec and line broadening (1b)=0.5 Hz.
- a Bruker Avance DRX 500 MHz NMR spectrometer
- a Bruker Avance III 600 MHz NMR spectrometer Chemical shifts are referenced to signals deriving from residual protons of the deuterated solvents (DMSO-$d_6$, Benzene-ds or $CDCl_3$). Chemical shifts are given in parts per million (ppm) and coupling constants (J) in Hertz (Hz). Spin multiplicities are given as broad (br), singlet (s), doublet (d), triplet (t), quartet (q) and multiplet (m).

Products were generally dried under vacuum before final analyses and submission to biological testing.

A-IV: Example Compounds and Synthesis

The names of the following compounds are IUPAC names generated by Biovia Draw Version 16.1 for Intermediates of Formula X, XI, XII and by Pipeline Pilot 2018 using OpenEye oemetachem version 1.4.5 for Example compounds of Formula I.

Intermediates

When commercially available, starting materials are identified by their CAS Register Numbers.

A. Synthesis of Intermediates of Formula X

A.1. Synthesis of 3,6-difluoro-5-(2-fluoroethoxy)pyridin-2-amine X-1

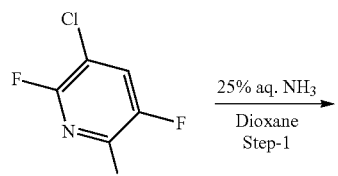

CAS: 2879-42-7

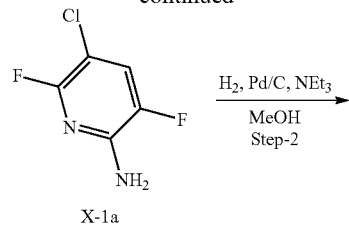

X-1a

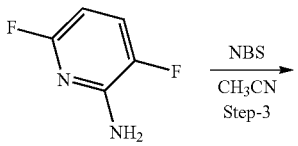

X-1b

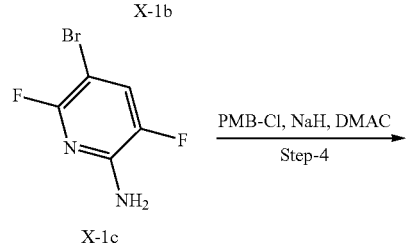

X-1c

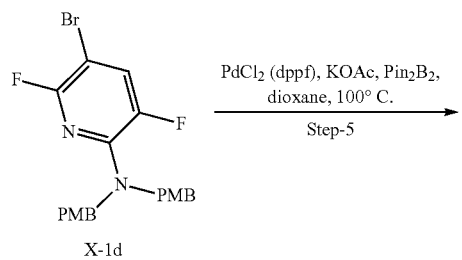

X-1d

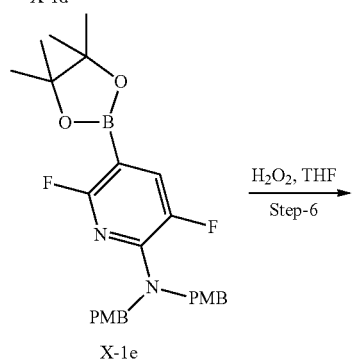

X-1e

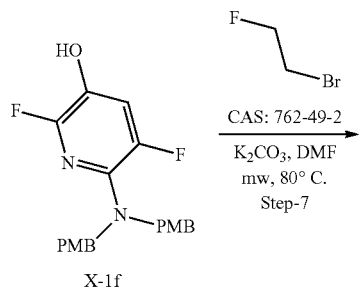

X-1f

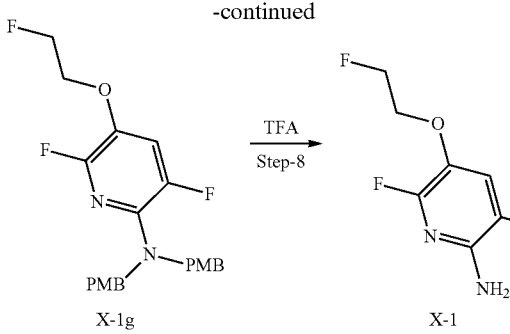

Step-1: Synthesis of 5-chloro-3,6-difluoro-pyridin-2-amine X-1a

To a solution of 3-chloro-2,5,6-trifluoro-pyridine (0.50 g, 2.98 mmol) in DMSO (10 mL) was added 25% aqueous NH3 (4 mL) and the reaction mixture was heated in steel bumb at 100° C. for 12 h. Progress of the reaction was monitored by TLC and LCMS. After completion, the reaction mixture was diluted with $H_2O$ (200 mL) and extracted with EtOAc (400 mL). The organic layer was separated, dried over anhydrous $Na_2SO_4$ and concentrated under vacuum to afford 5-chloro-3,6-difluoro-pyridin-2-amine X-1a (0.41 g crude) as a yellow solid.

This compound was used as such for the next reaction without further purification.

$^1$H NMR (400 MHz, DMSO-$d_6$) δ 6.85 (s, 2H), 7.80-7.85 (m, 1H).

Step-2: Synthesis of 3,6-difluoropyridin-2-amine X-1 b

To a solution of 5-chloro-3,6-difluoro-pyridin-2-amine X-1a (0.50 g, 3.03 mmol) in MeOH (100 mL) was added triethylamine (5 mL) and Pd/C (0.40 g) and the reaction mixture was stirred at room temperature under hydrogen pressure in parr shaker for 10 h. Progress of the reaction was monitored by TLC and LCMS. After completion, the reaction mixture was filtered through celite, and filtrate was concentrated under vacuum. The residue was diluted with $H_2O$ (200 mL) and extracted with 10% MeOH in DCM (200 mL). The organic layer was separated, dried over anhydrous $Na_2SO_4$ and concentrated under vacuum to afford 3,6-difluoropyridin-2-amine X-1b (0.21 g crude) as an off-white solid.

This compound was used as such for the next reaction without further purification.

Basic LC-MS Method 2 (ES$^+$): 130 (M)+, 91% purity.
$^1$H NMR (400 MHz, DMSO-$d_6$) δ 6.09-6.11 (m, 1H) 6.57 (brs, 2H) 7.44-7.50 (m, 1H).

Step-3: Synthesis of 5-bromo-3,6-difluoro-pyridin-2-amine X-1c

To a solution of 3,6-difluoropyridin-2-amine X-1b (0.60 g, 4.19 mmol) in $CH_3CN$ (40 mL) was added NBS (0.52 g, 2.93 mmol) and the reaction mixture was stirred in absence of light at room temperature for 30 min. NBS (0.52 g, 2.93 mmol) solution in $CH_3CN$ (10 mL) was added and the reaction mixture was stirred at room temperature for 30 min. Progress of the reaction was monitored by TLC and LCMS. After completion, the reaction mixture was diluted with $H_2O$ (100 mL) and extracted with EtOAc (160 mL). The organic layer was separated, dried over anhydrous $Na_2SO_4$ and concentrated under vacuum. The crude obtained was purified by column chromatography (silica, 100-200 mesh, 5 to 10% EtOAc in hexanes) to afford 5-bromo-3,6-difluoropyridin-2-amine X-1c (0.70 g) as an off-white solid.

Yield: 79%
Basic LC-MS Method 2 (ES$^-$): 207 (M–H)$^-$, 98% purity.
$^1$H NMR (400 MHz, DMSO-$d_6$) δ 6.86 (brs, 2H) 7.82-7.91 (m, 1H).

Step-4: Synthesis of 5-bromo-3,6-difluoro-N,N-bis[(4-methoxyphenyl)methyl]pyridin-2-amine X-1d To a solution of 5-bromo-3,6-difluoropyridin-2-amine X-1c (4.00 g, 19.0 mmol) in DMAC (40 mL) was added NaH (2.29 g, 57.1 mmol) portion wise at 0° C. and the reaction was stirred at the same temperature for 30 min. Para-methoxybenzyl chloride (5.19 mL, 38.1 mmol) was added dropwise at 0° C. and the reaction mixture was stirred at room temperature for 2 h. Progress of the reaction was monitored by TLC. After completion, the reaction mixture was cooled to 0° C., quenched with saturated $NH_4Cl$ (20 mL), poured into $H_2O$ (60 mL) and extracted with EtOAc (3×60 mL). The organic layer was separated, washed with brine (2×80 mL), dried over anhydrous $Na_2SO_4$ and concentrated under vacuum. The crude obtained was purified by column chromatography (silica, 100-200 mesh, 4% EtOAc in hexanes) to afford 5-bromo-3,6-difluoro-N,N-bis[(4-methoxyphenyl)methyl]pyridin-2-amine X-1d (8.2 g, 96%) as an off-white solid.

Yield: 96%.
$^1$H NMR (400 MHz, DMSO-$d_6$) δ 3.72 (s, 6H) 4.57 (s, 4H) 6.87-6.89 (m, 4H) 7.16-7.18 (m, 4H) 7.99-8.07 (m, 1H).

Step-5: Synthesis of 3,6-difluoro-N,N-bis[(4-methoxyphenyl)methyl]-5-(4,4,5,5-tetramethyl-1,3,2-dioxaborolan-2-yl)pyridin-2-amine X-1e To a solution of 5-bromo-3,6-difluoro-N,N-bis[(4-methoxyphenyl)methyl]pyridin-2-amine X-1d (4.00 g, 8.90 mmol) in dioxane (160 mL) was added Bis(pinacolato) diboron (4.52 g, 17.8 mmol) and KOAc (3.06 g, 31.2 mmol) at room temperature and the reaction mixture was purged with argon for 20 min followed by addition of PdCl$_2$ (dppf) (0.65 g, 0.89 mmol). The reaction mixture was purged with argon for 10 min and heated at 100° C. for 16 h. Progress of the reaction was monitored by TLC. After completion, the reaction mixture was cooled, filtered through a pad of celite and washed with EtOAc (2×80 mL). The filtrate was concentrated under vacuum, the residue was diluted with $H_2O$ (100 mL) and extracted with EtOAc (2×80 mL). The organic layer was separated, washed with brine (2×100 mL), dried over anhydrous $Na_2SO_4$ and concentrated under vacuum. The crude obtained was purified by column chromatography (silica, 100-200 mesh, 8% EtOAc in hexanes) to afford 3,6-difluoro-N,N-bis[(4-methoxyphenyl)methyl]-5-(4,4,5,5-tetramethyl-1,3,2-dioxaborolan-2-yl)pyridin-2-amine X-1e (2.60 g) as an off-white solid.

Yield: 59%.
$^1$H NMR (400 MHz, DMSO-$d_6$) δ 1.26 (s, 12H) 3.73 (s, 6H) 4.64 (s, 4H) 6.89 (d, J=8.31 Hz, 4H) 7.17 (d, J=8.80 Hz, 4H) 7.51-7.56 (m, 1H).

Step-6: Synthesis of 6-[bis[(4-methoxyphenyl)methyl]amino]-2,5-difluoro-pyridin-3-ol X-1f To a solution of 3,6-difluoro-N,N-bis[(4-methoxyphenyl)methyl]-5-(4,4,5,5-tetramethyl-1,3,2-dioxaborolan-2-yl)

pyridin-2-amine X-1e (2.50 g, 5.04 mmol) in THF (30 mL) was added 30% H$_2$O$_2$ solution in H$_2$O (10 mL) at 0° C. and the reaction mixture was stirred at same temperature for 15 min. The reaction mixture was stirred at room temperature for 1.5 h. Progress of the reaction was monitored by TLC and LCMS. The reaction mixture was poured into 5% Na$_2$S$_2$O$_3$ solution in cold H$_2$O (250 mL) at 0° C., diluted with H$_2$O (100 mL) and extracted with EtOAc (2×100 mL). The organic layer was separated, dried over anhydrous Na$_2$SO$_4$ and concentrated under vacuum to afford 6-[bis[(4-methoxyphenyl)methyl]amino]-2,5-difluoro-pyridin-3-ol X-1f (1.74 g crude) as a yellow semi solid.

This compound was used as such for the next reaction without further purification.

Basic LC-MS Method 2 (ES$^+$): 387 (M+H)$^+$, 93% purity.
$^1$H NMR (400 MHz, DMSO-d$_6$) δ 3.71 (s, 6H) 4.32 (s, 4H) 6.86 (d, J=8.80 Hz, 4H) 7.14 (d, J=8.31 Hz, 4H) 7.22-7.27 (m, 1H) 9.84 (s, 1H).

Step-7: Synthesis of 3,6-difluoro-5-(2-fluoroethoxy)-N,N-bis[(4-methoxyphenyl)methyl]pyridin-2-amine X-1g To a solution of 6-[bis[(4-methoxyphenyl)methyl]amino]-2,5-difluoro-pyridin-3-ol X-1f (0.70 g, 1.68 mmol) in DMF (13 mL) was added K$_2$CO$_3$ (0.70 g, 5.04 mmol) and 1-bromo-2-fluoroethane (0.43 g, 3.36 mmol) at room temperature. The reaction mixture was heated in microwave at 80° C. for 15 min. Progress of the reaction was monitored by TLC and LCMS. After completion, the reaction mixture was cooled to room temperature, poured into H$_2$O (30 mL) and extracted with EtOAc (3×25 mL). The organic layer was separated, washed with brine (2×30 mL), dried over anhydrous Na$_2$SO$_4$ and concentrated under vacuum. The crude obtained was purified by column chromatography (silica, 100-200 mesh, 25% EtOAc in hexanes) to afford 3,6-difluoro-5-(2-fluoroethoxy)-N,N-bis[(4-methoxyphenyl)methyl]pyridin-2-amine X-1g (0.52 g) as a brown liquid.
Yield: 71%.
Basic LC-MS Method 2 (ES$^+$): 433 (M+H)$^+$, 99% purity.
$^1$H NMR (400 MHz, DMSO-d$_6$) δ 3.72 (s, 6H) 4.21-4.25 (m, 1H) 4.29-4.32 (m, 1H) 4.42 (s, 4H) 4.63-4.66 (m, 1H) 4.75-4.78 (m, 1H) 6.87 (d, J=8.86 Hz, 4H) 7.15 (d, J=8.37 Hz, 4H) 7.69-7.76 (m, 1H).

Step-5: Synthesis of 3,6-difluoro-5-(2-fluoroethoxy)pyridin-2-amine X-1

To 3,6-difluoro-5-(2-fluoroethoxy)-N,N-bis[(4-methoxyphenyl)methyl]pyridin-2-amine X-1g (0.50 g, 1.15 mmol) was added TFA (5 mL) at 0° C. and the reaction mixture was stirred at same temperature for 30 min. The reaction mixture was stirred at room temperature for 2 h. Progress of the reaction was monitored by TLC and LCMS. After completion, the reaction mixture was concentrated under vacuum. The residue was diluted with H$_2$O (25 mL), basified with aqueous NaHCO$_3$ solution (10 mL) and extracted with EtOAc (2×25 mL). The organic layer was separated, washed with brine (2×40 mL), dried over anhydrous Na$_2$SO$_4$ and concentrated under vacuum. The crude obtained was purified by triturating with Et$_2$O (10 mL) and dried under vacuum to afford 3,6-difluoro-5-(2-fluoroethoxy)pyridin-2-amine X-1 (0.258 g) as an off-white solid.
Yield: 80%.
Basic LC-MS Method 2 (ES$^+$): 193 (M+H)$^+$, 69% purity.
$^1$H NMR (400 MHz, DMSO-d$_6$) δ 4.13-4.17 (m, 1H) 4.20-4.25 (m, 1H) 4.59-4.64 (m, 1H) 4.71-4.76 (m, 1H) 6.10 (s, 2H) 7.57-7.62 (m, 1H).

A.2. Synthesis of 3-fluoro-5-(2-fluoroethoxy)pyridin-2-amine X-2

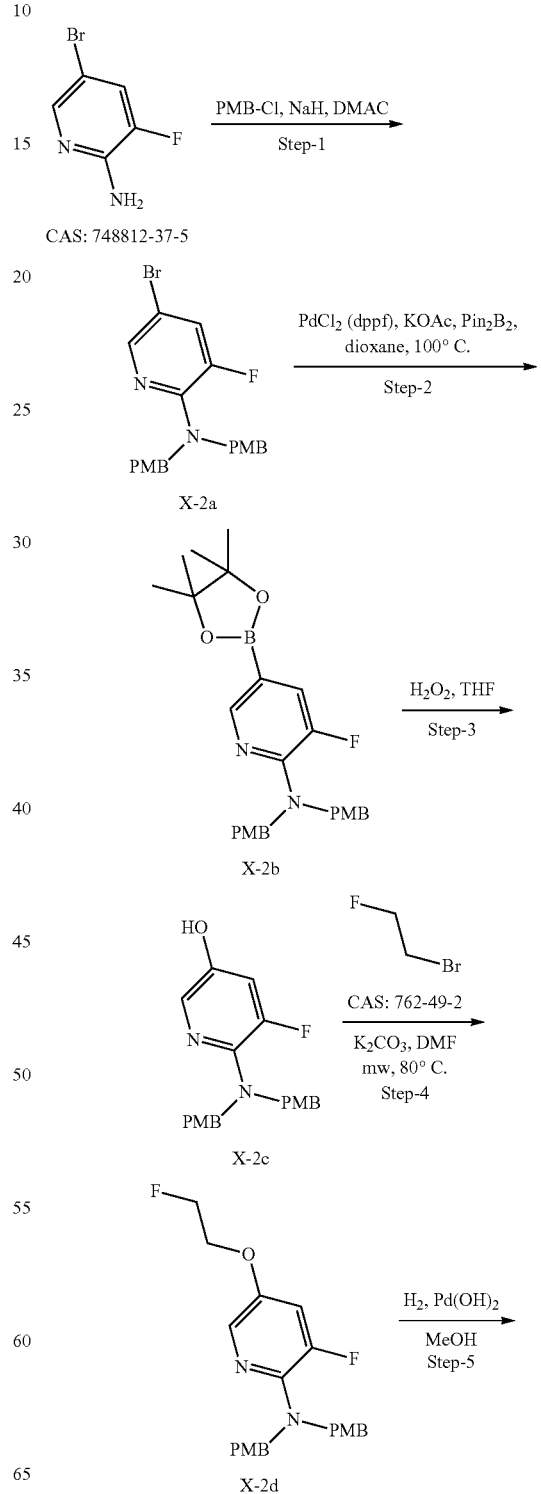

-continued

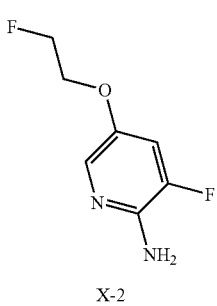

X-2

Step-1: Synthesis of 5-bromo-3-fluoro-N,N-bis(4-methoxybenzyl)pyridin-2-amine X-2a To a solution of 5-bromo-3-fluoro-pyridin-2-amine (2.00 g, 10.5 mmol) in DMAC (30 mL) was added NaH (1.26 g, 31.4 mmol) lot wise at 0° C. and the reaction mixture was stirred at same temperature for 30 min. p-Methoxybenzyl chloride (2.85 mL, 20.9 mmol) was added at 0° C. and the reaction mixture was stirred at room temperature for 2 h. Progress of the reaction was monitored by TLC and LCMS. After completion, the reaction mixture was cooled at 0° C., quenched with saturated NH 4 Cl solution (200 mL), poured in to ice $H_2O$ (400 mL) and extracted with EtOAc (2×300 mL). The organic layer was separated, washed with brine (2×100 mL), dried over anhydrous $Na_2SO_4$ and concentrated under vacuum. The crude obtained was purified by column chromatography (silica, 100-200 mesh, 3% EtOAc in hexanes) to afford 5-bromo-3-fluoro-N,N-bis(4-methoxybenzyl)pyridin-2-amine X-2a (4.10 g) as a pale yellow semi solid.

Yield: 87%

Basic LC-MS Method 2 (ES+): 431 (M+H)+, 95% purity.

$^1$H NMR (400 MHz, DMSO-$d_6$) δ 3.72 (s, 6H), 4.57 (s, 4H), 6.87 (d, J=8.31 Hz, 4H), 7.15 (d, J=8.80 Hz, 4H), 7.81 (dd, J=12.96, 1.71 Hz, 1H), 8.06 (s, 1H).

Step-2: Synthesis of 3-fluoro-N,N-bis(4-methoxybenzyl)-5-(4,4,5,5-tetramethyl-1,3,2-dioxaborolan-2-yl)pyridin-2-amine X-2b To a solution of 5-bromo-3-fluoro-N,N-bis(4-methoxybenzyl)pyridin-2-amine X-2a (2.00 g, 4.43 mmol) in dioxane (60 mL) was added bis(pinacolato)diboron (2.25 g, 8.86 mmol) and KOAc (1.52 g, 15.5 mmol) at room temperature and the reaction mixture was purged with argon for 20 min followed by addition of $PdCl_2$ (dppf) (0.32 g, 0.44 mmol). The reaction mixture was purged with argon for 10 min and heated at 100° C. for 16 h. Progress of the reaction was monitored by TLC. After completion, the reaction mixture was cooled to room temperature, filtered through a pad of celite, washed with EtOAc (2×300 mL) and the filtrate was concentrated under vacuum. The crude obtained was purified by column chromatography (silica, 100-200 mesh, 5 to 10% EtOAc in hexanes). The product obtained was stirred in pentane (10 mL), decanted and dried under vacuum to afford 3-fluoro-N,N-bis(4-methoxybenzyl)-5-(4,4,5,5-tetramethyl-1,3,2-dioxaborolan-2-yl)pyridin-2-amine X-2b (1.31 g) as an off-white solid.

Yield: 56%

Basic LC-MS Method 2 (ES+): 479 (M+H)+, 90% purity.

$^1$H NMR (400 MHz, DMSO-$d_6$) δ 1.27 (s, 12H), 3.72 (s, 6H), 4.65 (s, 4H), 6.87 (d, J=8.80 Hz, 4H), 7.15 (d, J=8.31 Hz, 4H), 7.44 (d, J=15.16 Hz, 1H), 8.15 (s, 1H).

Step-3: Synthesis of 6-(bis(4-methoxybenzyl)amino)-5-fluoropyridin-3-ol X-2c To a solution of X-2b (1.31 g, 2.46 mmol) in THF (20 mL) was added 30% $H_2O_2$ solution in $H_2O$ (7 mL) at 0° C. and the reaction mixture was stirred at same temperature for 15 min. The reaction mixture was stirred at room temperature for 2 h. Progress of the reaction was monitored by TLC and LCMS. The reaction mixture was poured in to cold 5% $Na_2S_2O_3$ solution in $H_2O$ (350 mL) at 0° C., diluted with $H_2O$ (100 mL) and extracted with $Et_2O$ (2×200 mL). The organic layer was separated, dried over anhydrous $Na_2SO_4$ and concentrated under vacuum (low temperature) to afford 6-(bis(4-methoxybenzyl)amino)-5-fluoropyridin-3-ol X-2c (0.90 g crude) as a pale yellow semi solid.

This compound was used as such for the next reaction without further purification.

Basic LC-MS Method 2 (ES+): 369 (M+H)+, 94% purity.

Step-4: Synthesis of 3-fluoro-5-(2-fluoroethoxy)-N,N-bis[(4-methoxyphenyl)methyl]pyridin-2-amine X-2d To a solution of 6-(bis(4-methoxybenzyl)amino)-5-fluoropyridin-3-ol X-2c (1.70 g, 4.43 mmol) in DMF (10 mL) was added $K_2CO_3$ (0.77 g, 5.56 mmol) and 1-bromo-2-fluoroethane (0.67 g, 5.31 mmol) at room temperature. The reaction mixture was heated in microwave at 70° C. overnight. Progress of the reaction was monitored by TLC and LCMS. After completion, the reaction mixture was cooled to room temperature, poured into $H_2O$ (100 mL) and extracted with EtOAc (2×50 mL). The organic layer was separated, washed with ice cold water (2×25 mL), dried over anhydrous $Na_2SO_4$ and concentrated under vacuum. The crude obtained was purified by column chromatography (silica, 100-200 mesh, 5 to 8% EtOAc in hexanes) to afford 3-fluoro-5-(2-fluoroethoxy)-N,N-bis[(4-methoxyphenyl)methyl]pyridin-2-amine X-2d (0.80 g) as a brown liquid.

Yield: 43%

Basic LC-MS Method 2 (ES+): 415 (M+H)+, 99% purity.

$^1$H NMR (400 MHz, DMSO-$d_6$) δ 3.71 (s, 6H), 4.14-4.22 (m, 1H), 4.25-4.29 (m, 1H), 4.40 (s, 4H), 4.63-4.68 (m, 1H), 4.74-4.80 (m, 1H), 6.85 (d, J=8.80 Hz, 4H), 7.14 (d, J=8.31 Hz, 4H), 7.39 (dd, J=14.18, 2.45 Hz, 1H), 7.78 (d, J=1.96 Hz, 1H).

Step-5: Synthesis of 3-fluoro-5-(2-fluoroethoxy)pyridin-2-amine X-2

To a solution of X-2d (800 mg, 1.92 mmol) in MeOH (3 mL) was added palladium hydroxide (160 mg) and the reaction mixture was stirred at room temperature for 6 h under hydrogen pressure. Progress of the reaction was monitored by TLC and LCMS. After completion, the reaction mixture was filtered through celite, washed with MeOH (2×25 mL) and the filtrate was concentrated under vacuum. The residue was purified by column chromatography (silica, 100-200 mesh, 10 to 15% EtOAc in hexanes) to afford 3-fluoro-5-(2-fluoroethoxy)pyridin-2-amine X-2 (100 mg) as a brown solid.

Yield: 29%

Basic LC-MS Method 2 (ES+): 175 (M+H)+, 97% purity.

¹H NMR (400 MHz, DMSO-d₆) δ 4.11-4.16 (m, 1H), 4.19-4.23 (m, 1H), 4.60-4.64 (m, 1H), 4.72-4.77 (m, 1H), 5.72 (s, 2H), 7.27 (dd, J=12.23, 2.45 Hz, 1H), 7.59 (d, J=2.45 Hz, 1H).

A.3. Synthesis of 3-fluoro-5-(2,2-difluoroethoxy)pyridin-2-amine X-3

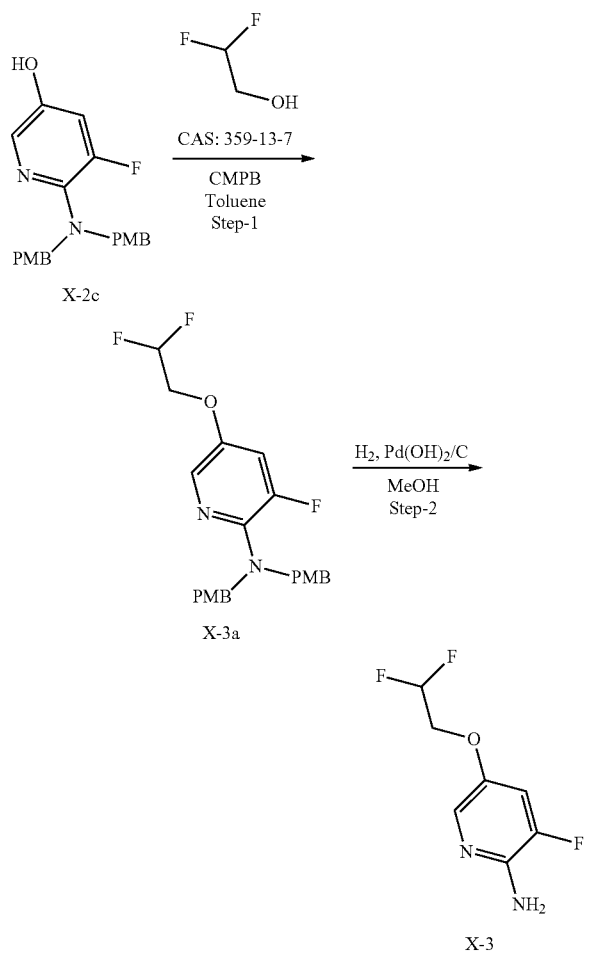

Step-1: Synthesis of 5-(2,2-difluoroethoxy)-3-fluoro-N,N-bis[(4-methoxyphenyl)methyl]pyridin-2-amine X-3a To a solution of 6-(bis(4-methoxybenzyl)amino)-5-fluoropyridin-3-ol X-2c (1.40 g, 3.69 mmol) and 2,2-difluoroethanol (0.66 g, 8.11 mmol) in toluene (25 mL). (Cyanomethylene)tributylphosphorane (1.96 g, 8.11 mmol) was slowly added at room temperature. The reaction mixture was heated at 100° C. for 4 h. Progress of the reaction was monitored by TLC. After completion, the reaction mixture was cooled to room temperature, poured into H₂O (80 mL) and extracted with EtOAc (3×100 mL). The organic layer was separated, dried over anhydrous Na₂SO₄ and concentrated under vacuum. The crude obtained was purified by column chromatography (silica, 100-200 mesh, 10% EtOAc in hexanes) to afford 5-(2,2-difluoroethoxy)-3-fluoro-N,N-bis[(4-methoxyphenyl)methyl]pyridin-2-amine X-3a (1.22 g) as a pale yellow liquid.

Yield: 59%
Basic LC-MS Method 2 (ES⁺): 433 (M+H)⁺, 77% purity.

Step-2: Synthesis of 3-fluoro-5-(2,2-difluoroethoxy)pyridin-2-amine X-3

To a solution of X-3a (1.20 g, 2.19 mmol) in MeOH (30 mL) was added palladium hydroxide on carbon (500 mg) and the reaction mixture was stirred at room temperature for 6 h under hydrogen pressure. Progress of the reaction was monitored by TLC and LCMS. After completion, the reaction mixture was filtered through celite, washed with MeOH (2×50 mL) and the filtrate was concentrated under vacuum to afford 3-fluoro-5-(2,2-difluoroethoxy)pyridin-2-amine X-3 (590 mg) as a pale yellow semi solid.

This compound was used as such for the next reaction without further purification.
Yield: 77%
Basic LC-MS Method 2 (ES⁺): 193 (M+H)⁺, 55% purity.

A.4. Synthesis of 5-(2,2-difluoroethoxy)-3,6-difluoropyridin-2-amine X-4

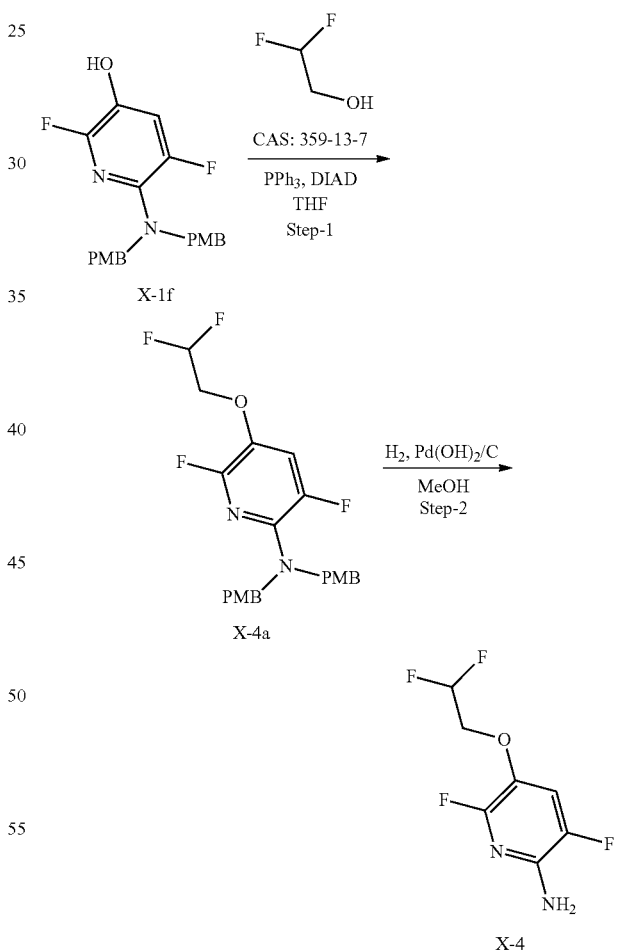

Step-1: Synthesis of 5-(2,2-difluoroethoxy)-3,6-difluoro-N,N-bis[(4-methoxyphenyl)methyl]pyridin-2-amine X-4a To a solution of 6-[bis[(4-methoxyphenyl)methyl]amino]-2,5-difluoro-pyridin-3-ol X-1f (100 mg, 0.16 mmol), 2,2- difluoroethanol (27 mg, 0.33 mmol) and triphenylphosphine (218 mg, 0.83 mmol) in THF (5 ml). Diisopropyl azodicarboxylate (168 mg, 0.829 mmol) was slowly added at room temperature. The reaction mixture was stirred at room temperature for 1 h. Progress of the reaction was monitored by TLC. After completion, the reaction mixture was diluted with H$_2$O (20 mL) and extracted with EtOAc (20 mL). The organic layer was separated, dried over anhydrous Na$_2$SO$_4$ and concentrated under vacuum to afford 5-(2,2-difluoroethoxy)-3,6-difluoro-N,N-bis[(4-methoxyphenyl)methyl] pyridin-2-amine X-4a (20 mg) as a semi solid.

This compound was used as such for the next reaction without further purification.

Yield: 27%

$^1$H NMR (400 MHz, DMSO-d$_6$) δ 3.72 (s, 6H), 4.44 (s, 4H), 4.79-4.85 (m, 2H), 6.01-6.31 (m, 1H), 6.87 (d, J=8.31 Hz, 4H), 7.15 (d, J=8.31 Hz, 4H), 7.76-7.81 (m, 1H).

Step-2: Synthesis of 5-(2,2-difluoroethoxy)-3,6-difluoro pyridin-2-amine X-4

To a solution of X-4a (540 mg, 1.20 mmol) in MeOH (10 mL) was added palladium hydroxide on carbon (54 mg) and the reaction mixture was stirred at room temperature for 1 h under hydrogen pressure. Progress of the reaction was monitored by TLC and LCMS. After completion, the reaction mixture was filtered through celite, washed with MeOH (2×50 mL) and the filtrate was concentrated under vacuum to afford 5-(2,2-difluoroethoxy)-3,6-difluoropyridin-2-amine X-4 (300 mg) as a brown solid.

This compound was used as such for the next reaction without further purification.

Yield: 71%

Basic LC-MS Method 2 (ES$^+$): 211 (M+H)$^+$, 60% purity.

A.5. Synthesis of 5-(2,2-difluoroethoxy)-3-fluoro-6-methoxypyridin-2-amine X-5

To a solution of 5-(2,2-difluoroethoxy)-3,6-difluoropyridin-2-amine X-4 (0.39 g, 1.74 mmol) in MeOH (14 mL) was added NaOMe (0.48 g, 8.79 mmol) and the reaction mixture was heated at 100° C. for 30 h. Progress of the reaction was monitored by TLC and LCMS. After completion, the reaction mixture was concentrated under vacuum. The residue was diluted with H$_2$O (500 mL) and extracted with EtOAc (600 mL). The organic layer was separated, dried over anhydrous Na$_2$SO$_4$ and concentrated under vacuum to afford 5-(2,2-difluoroethoxy)-3-fluoro-6-methoxypyridin-2-amine X-5 (0.37 g) as a brown solid.

This compound was used as such for the next reaction without further purification.

Yield: 67%

Basic LC-MS Method 2 (ES$^-$): 221 (M−H)$^-$, 70% purity.

1H NMR (400 MHz, DMSO-d6) δ 3.78 (s, 3H) 4.13 (td, J=14.67, 3.42 Hz, 2H) 5.72 (brs, 2H) 6.13-6.45 (m, 1H) 7.34 (d, J=10.76 Hz, 1H).

A.6. Synthesis of 5-(difluoromethoxy)-3-methoxypyridin-2-amine X-6

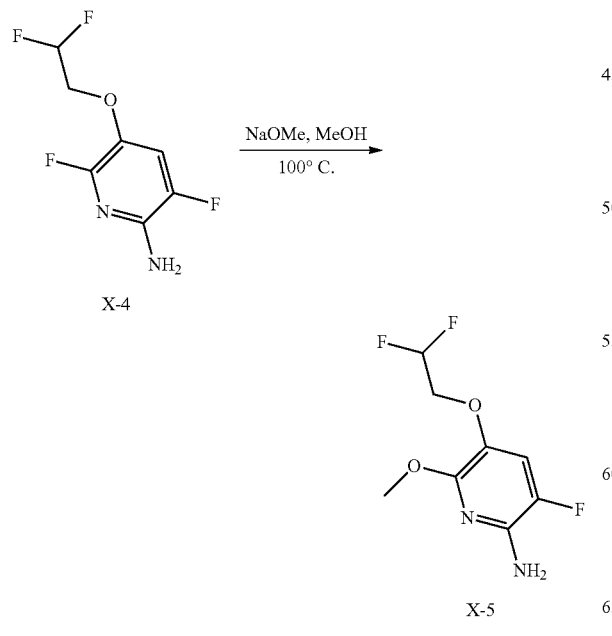

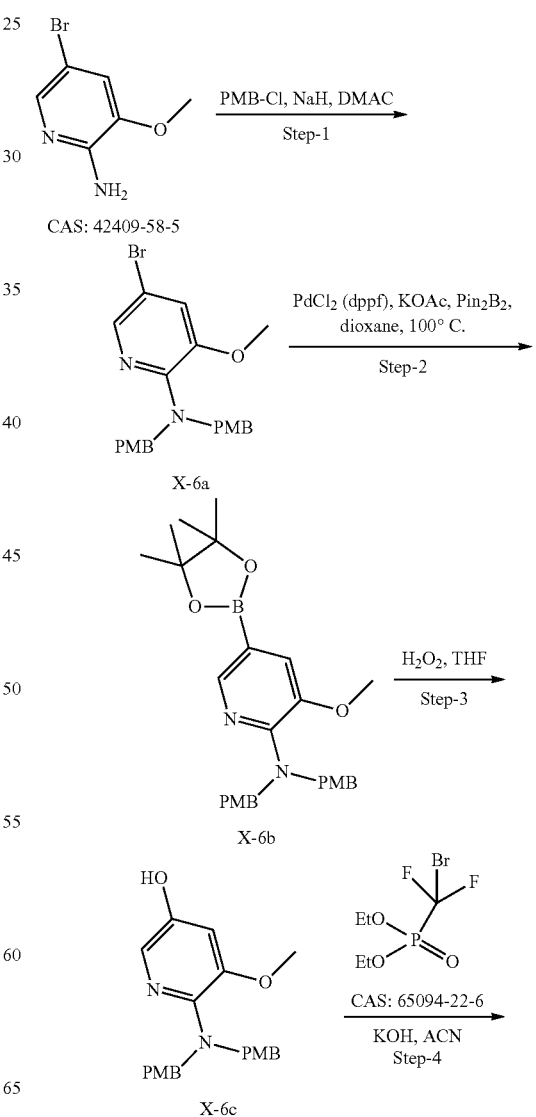

-continued

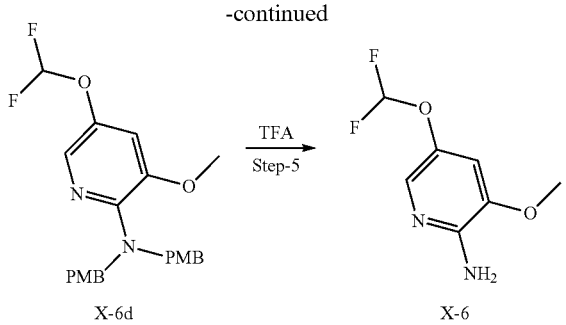

Step-1: Synthesis of 5-bromo-3-methoxy-N,N-bis (4-methoxybenzyl)pyridin-2-amine X-6a To a solution of 5-bromo-3-methoxy-pyridin-2-amine (5.00 g, 24.6 mmol) in DMF (75 mL) was added NaH (2.95 g, 73.9 mmol) lot wise at 0° C. and the reaction mixture was stirred at same temperature for 30 min. p-Methoxybenzyl chloride (6.71 mL, 49.3 mmol) was added drop wise at 0° C. and the reaction mixture was stirred at room temperature for 2 h. Progress of the reaction was monitored by TLC and LCMS. After completion, the reaction mixture was cooled at 0° C., quenched with cold H$_2$O (250 mL) and a saturated NH$_4$Cl solution (250 mL) and extracted with EtOAc (2×500 mL). The organic layer was separated, washed with brine (2×100 mL), dried over anhydrous Na$_2$SO$_4$ and concentrated under vacuum. The crude obtained was purified by column chromatography (silica, 100-200 mesh, 25% EtOAc in hexanes) to afford 5-bromo-3-methoxy-N,N-bis(4-methoxybenzyl)pyridin-2-amine X-6a (9.65 g) as an off-white solid.

Yield: 75%

Basic LC-MS Method 2 (ES$^+$): 443 (M+H)$^+$, 85% purity.
$^1$H NMR (400 MHz, DMSO-d$_6$) δ 3.69 (s, 6H) 3.82 (s, 3H) 4.42 (s, 4H) 6.79-6.85 (m, 4H) 7.11 (d, J=8.31 Hz, 4H) 7.39 (d, J=1.96 Hz, 1H) 7.76 (d, J=1.96 Hz, 1H).

Step-2: Synthesis of 3-methoxy-N,N-bis(4-methoxybenzyl)-5-(4,4,5,5-tetramethyl-1,3,2-dioxaborolan-2-yl)pyridin-2-amine X-6b To a solution of 5-bromo-3-methoxy-N,N-bis(4-methoxybenzyl)pyridin-2-amine X-6a (9.60 g, 18.3 mmol) in dioxane (300 mL) was added bis(pinacolato)diboron (9.31 g, 36.7 mmol) and KOAc (6.30 g, 64.1 mmol) at room temperature and the reaction mixture was purged with argon for 20 min followed by addition of PdCl$_2$ (dppf) (1.34 g, 1.83 mmol). The reaction mixture was purged with argon for 10 min and heated at 100° C. for 16 h. Progress of the reaction was monitored by TLC and LCMS. After completion, the reaction mixture was cooled to room temperature, filtered through a pad of celite, washed with EtOAc (2×300 mL) and the filtrate was concentrated under vacuum. The crude obtained was purified by column chromatography (silica, 100-200 mesh, 5 to 10% EtOAc in hexanes). The product obtained was stirred with pentane (50 mL), decanted and dried under vacuum to afford 3-methoxy-N,N-bis(4-methoxybenzyl)-5-(4,4,5,5-tetramethyl-1,3,2-dioxaborolan-2-yl)pyridin-2-amine X-6b (5.10 g) as an off-white solid.

Yield: 47%

Basic LC-MS Method 2 (ES$^+$): 491 (M+H)$^+$, 83% purity.
$^1$H NMR (400 MHz, DMSO-d$_6$) δ 1.26 (s, 12H) 3.69 (s, 6H) 3.77 (s, 3H) 4.55 (s, 4H) 6.82 (d, J=8.80 Hz, 4H) 7.11 (d, J=8.31 Hz, 4H) 7.21 (s, 1H) 7.94 (s, 1H).

Step-3: Synthesis of 6-(bis(4-methoxybenzyl) amino)-5-methoxypyridin-3-ol X-6c To a solution of 3-methoxy-N,N-bis(4-methoxybenzyl)-5-(4,4,5,5-tetramethyl-1,3,2-dioxaborolan-2-yl)pyridin-2-amine X-6b (5.00 g, 8.49 mmol) in THF (100 mL) was added 30% H$_2$O$_2$ solution in H$_2$O (40 mL) slowly at 0° C. After 15 min, the reaction mixture was stirred at room temperature for 2 h. Progress of the reaction was monitored by TLC and LCMS. After completion, the reaction mixture was poured into a cold 6% Na$_2$S$_2$O$_3$ solution in H$_2$O (600 mL) at 0° C., diluted with H$_2$O (500 mL) and extracted with Et$_2$O (2×400 mL). The organic layer was separated, dried over anhydrous Na$_2$SO$_4$ and concentrated under vacuum (at low temperature, 20 to 25° C.). The residue was washed with pentane (15 mL) to afford 6-(bis(4-methoxybenzyl)amino)-5-methoxypyridin-3-ol X-6c (3.50 g crude) as a pale yellow solid.

This compound was used as such for the next reaction without further purification.

Basic LC-MS Method 2 (ES$^+$): 381 (M+H)$^+$, 84% purity.
$^1$H NMR (400 MHz, DMSO-d$_6$) δ 3.69 (s, 6H) 3.81 (s, 3H) 4.18 (s, 4H) 6.77 (d, J=2.45 Hz, 1H) 6.80 (d, J=8.31 Hz, 4H) 7.12 (d, J=8.80 Hz, 4H) 7.28 (d, J=2.45 Hz, 1H) 9.21 (s, 1H).

Step-4: Synthesis of 5-(difluoromethoxy)-3-methoxy-N,N-bis(4-methoxybenzyl)pyridin-2-amine X-6d To a solution of 6-(bis(4-methoxybenzyl)amino)-5-methoxypyridin-3-ol X-6c (3.30 g, 7.31 mmol) in CH$_3$CN (60 mL) was added KOH (2.26 g, 40.2 mmol) solution in H$_2$O (20 mL) drop wise at 0° C. followed by addition of bromodifluoromethyl diethylphosphonate (10.7 g, mmol) at 0° C. After 15 min, the reaction mixture was stirred at room temperature for 2 h. Progress of the reaction was monitored by TLC and LCMS. After completion, the reaction mixture was quenched with H$_2$O (200 mL) and extracted with EtOAc (2×250 mL). The organic layer was separated, dried over anhydrous Na$_2$SO$_4$ and concentrated under vacuum. The crude obtained was purified by column chromatography (silica, 100-200 mesh, 5% EtOAc in hexanes) to afford 5-(difluoromethoxy)-3-methoxy-N,N-bis(4-methoxybenzyl)pyridin-2-amine X-6d (3.21 g) as a pale yellow semi solid.

Yield: 92%

Basic LC-MS Method 2 (ES$^+$): 431 (M+H)$^+$, 90% purity.
$^1$H NMR (400 MHz, DMSO-d$_6$) δ 3.70 (s, 6H) 3.85 (s, 3H) 4.39 (s, 4H) 6.83 (d, J=8.80 Hz, 4H) 7.11-7.16 (m, 4H) 7.14 (t, J=74 Hz, 1H) 7.19 (d, J=2.45 Hz, 1H) 7.62 (d, J=1.96 Hz, 1H).

Step-5: Synthesis of 5-(difluoromethoxy)-3-methoxypyridin-2-amine X-6

To 5-(difluoromethoxy)-3-methoxy-N,N-bis(4-methoxybenzyl)pyridin-2-amine X-6d (2.50 g, 5.26 mmol) was added TFA (15 mL) at 0° C. and the reaction mixture was stirred at room temperature for 4 h. Progress of the reaction was monitored by TLC and LCMS. After completion, the reaction mixture was concentrated under vacuum. The residue was diluted with H$_2$O (400 mL) and a saturated solution of NaHCO$_3$ (250 mL) and extracted with EtOAc (2×300 mL). The organic layer was separated, dried over anhydrous Na$_2$SO$_4$ and concentrated under vacuum. The crude obtained was purified by flash chromatography (40% EtOAc in hexanes) to afford 5-(difluoromethoxy)-3-methoxypyridin-2-amine X-6 (0.52 g) as an off-white solid.

Yield: 52%

Basic LC-MS Method 2 (ES$^+$): 191 (M+H)$^+$, 99% purity.

$^1$H NMR (400 MHz, DMSO-d$_6$) δ 3.79 (s, 3H) 5.77 (s, 2H) 6.98 (d, J=1.96 Hz, 1H) 7.01 (t, J=74 Hz, 1H) 7.42 (d, J=1.96 Hz, 1H).

A.7. Synthesis of 5-(2,2-difluoroethoxy)-3-methoxypyridin-2-amine X-7

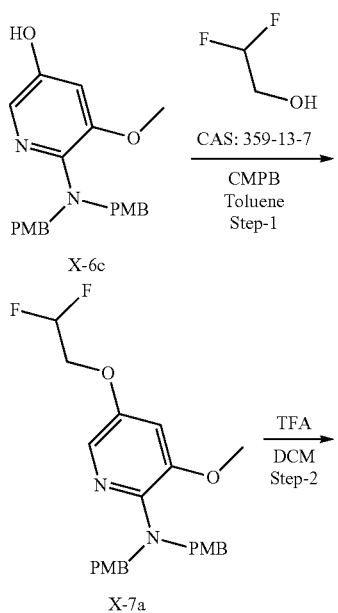

Step-1: Synthesis of 5-(2,2-difluoroethoxy)-3-methoxy-N,N-bis(4-methoxybenzyl)pyridin-2-amine X-7a To a solution of 6-(bis(4-methoxybenzyl)amino)-5-methoxypyridin-3-ol X-6c (2.80 g, 7.01 mmol) and 2,2-difluoroethanol (0.89 mL, 14.0 mmol) in toluene (30 mL) was added Cyanomethylenetributylphosphorane (3.67 mL, 14.0 mmol) slowly at room temperature and the reaction mixture was heated at 100° C. for 2 h. Progress of the reaction was monitored by TLC and LCMS. After completion, the reaction mixture was diluted with H$_2$O (30 mL) and extracted with EtOAc (3×40 mL). The organic layer was separated, dried over anhydrous Na$_2$SO$_4$ and concentrated under vacuum. The crude obtained was purified by column chromatography (silica, 100-200 mesh, 30% EtOAc in hexanes) to afford 5-(2,2-difluoroethoxy)-3-methoxy-N,N-bis(4-methoxybenzyl)pyridin-2-amine X-7a (2.10 g) as a pale yellow oil.

Yield: 67%

Basic LC-MS Method 2 (ES$^+$): 445 (M+H)$^+$, 99% purity.

$^1$H NMR (400 MHz, DMSO-d$_6$) δ 3.68 (s, 6H) 3.85 (s, 3H) 4.24-4.34 (m, 6H) 6.19-6.49 (m, 1H) 6.80 (d, J=8.80 Hz, 4H) 7.03 (d, J=1.96 Hz, 1H) 7.11 (d, J=8.31 Hz, 4H) 7.48 (d, J=2.45 Hz, 1H).

Step-2: Synthesis of 5-(2,2-difluoroethoxy)-3-methoxypyridin-2-amine X-7

To a 5-(2,2-difluoroethoxy)-3-methoxy-N,N-bis(4-methoxybenzyl)pyridin-2-amine X-7a (1.70 g, 3.82 mmol) in DCM (15 ml) was added TFA (10 mL) drop wise at 0° C. and the reaction mixture was stirred at room temperature for 4 h. Progress of the reaction was monitored by TLC and LCMS. After completion, the reaction mixture was concentrated under vacuum. The residue was diluted with H$_2$O (20 mL), saturated NaHCO$_3$ (20 mL) and extracted with EtOAc (2×30 mL). The organic layer was separated, dried over anhydrous Na$_2$SO$_4$ and concentrated under vacuum. The crude obtained was purified by flash chromatography (30% EtOAc in hexanes) to afford 5-(2,2-difluoroethoxy)-3-methoxypyridin-2-amine X-7 (0.605 g) as pale yellow solid.

Yield: 74%

Basic LC-MS Method 2 (ES$^+$): 205 (M+H)$^+$, 99% purity.

$^1$H NMR (400 MHz, DMSO-d$_6$) δ 3.77 (s, 3H) 4.23 (td, J=14.80, 3.67 Hz, 2H) 5.33 (s, 2H) 6.18-6.50 (m, 1H) 6.88 (d, J=2.45 Hz, 1H) 7.31 (d, J=2.45 Hz, 1H).

A.8. Synthesis of 5-(2-(difluoromethoxy)ethoxy)-3-fluoro-6-methoxypyridin-2-amine X-8

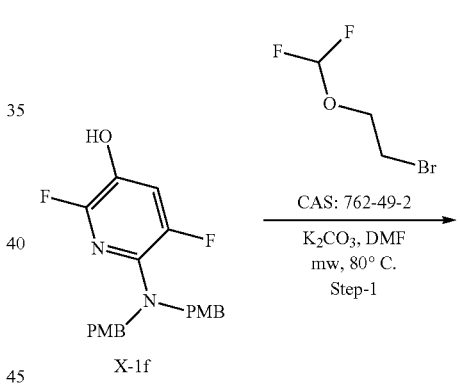

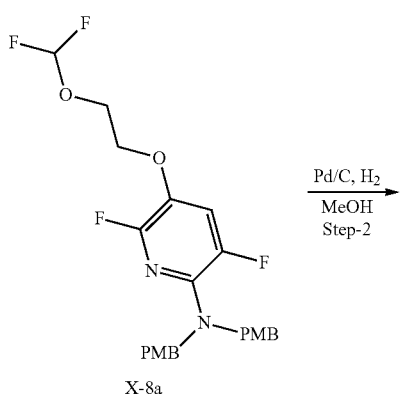

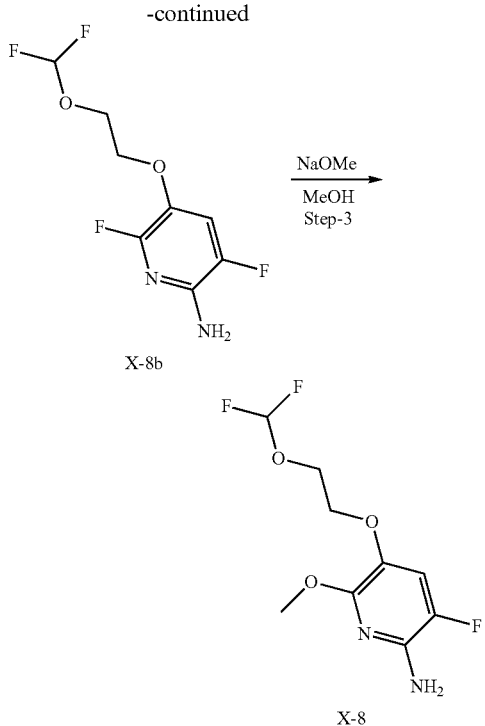

Step-1: Synthesis of 5-(2-(difluoromethoxy)ethoxy)-3,6-difluoro-N,N-bis(4-methoxybenzyl)pyridin-2-amine X-8a To a solution of 6-[bis[(4-methoxyphenyl)methyl]amino]-2,5-difluoro-pyridin-3-ol X-1f (0.80 g, 1.52 mmol) in DMF (10 mL) was added K$_2$CO$_3$ (0.63 g, 4.56 mmol) and 1-bromo-2-(difluoromethoxy)ethane (0.29 g, 1.67 mmol) at room temperature. The reaction mixture was heated in microwave at 85° C. for 1.2 h. Progress of the reaction was monitored by TLC and LCMS. After completion, the reaction mixture was cooled to room temperature, poured in to H$_2$O (60 mL) and extracted with EtOAc (3×40 mL). The organic layer was separated, washed with brine (2×50 mL), dried over anhydrous Na$_2$SO$_4$ and concentrated under vacuum. The reaction was repeated on 0.70 g and 2×0.80 g and the crude obtained from 4 reactions was clubbed in DCM (200 mL) and purified by column chromatography (silica, 100-200 mesh, 8% EtOAc in hexanes) to afford 5-(2-(difluoromethoxy)ethoxy)-3,6-difluoro-N,N-bis(4-methoxybenzyl)pyridin-2-amine X-8a (1.31 g) as a brown liquid.

Yield: 34%

Basic LC-MS Method 2 (ES$^+$): 481 (M+H)$^+$, 99% purity.

Step-2: Synthesis of 5-(2-(difluoromethoxy)ethoxy)-3,6-difluoropyridin-2-amine X-8b To a solution of 5-(2-(difluoromethoxy)ethoxy)-3,6-difluoro-N,N-bis(4-methoxybenzyl)pyridin-2-amine X-8a (1.30 g, 2.36 mmol) in MeOH (25 mL) was added 20% Pd/C (0.13 g) at room temperature and the reaction mixture was stirred at room temperature for 2 h under hydrogen pressure. Progress of the reaction was monitored by TLC and LCMS. After completion, the reaction mixture was filtered through a pad of celite and washed with MeOH (2×30 mL). The filtrate was concentrated under vacuum. The crude obtained was purified by washing with pentane (2×20 mL) to afford 5-(2-(difluoromethoxy)ethoxy)-3,6-difluoropyridin-2-amine X-8b (0.525 g) as a pale brown solid.

Yield: 92%

Basic LC-MS Method 2 (ES$^+$): 241 (M+H)$^+$, 99% purity.

$^1$H NMR (400 MHz, DMSO-d$_6$) δ 4.03-4.07 (m, 2H) 4.08-4.10 (m, 2H) 6.07 (s, 2H) 6.68 (t, J=76 Hz 1H) 7.53-7.57 (m, 1H).

Step-3: Synthesis of 5-(2-(difluoromethoxy)ethoxy)-3-fluoro-6-methoxypyridin-2-amine X-8

To a solution of 5-(2-(difluoromethoxy)ethoxy)-3,6-difluoropyridin-2-amine X-8b (0.70 g, 2.91 mmol) in MeOH (15 mL) was added NaOMe (25% in MeOH, 1.57 mL, 7.29 mmol) at and the reaction mixture was heated at 70° C. for 24 h. Progress of the reaction was monitored by TLC and LCMS. After completion, the reaction mixture was concentrated under vacuum. The residue was diluted with H$_2$O (20 mL) and extracted with EtOAc (3×25 mL). The organic layer was separated, dried over anhydrous Na$_2$SO$_4$ and concentrated under vacuum. The crude obtained was purified by combi-flash chromatography (10% EtOAc in hexanes) to afford 5-(2-(difluoromethoxy)ethoxy)-3-fluoro-6-methoxypyridin-2-amine X-8 (0.45 g) as a pale yellow solid.

Yield: 59%

Basic LC-MS Method 2 (ES$^+$): 253 (M+H)$^+$, 94% purity.

$^1$H NMR (400 MHz, DMSO-d$_6$) δ 3.77 (s, 3H) 4.03-4.06 (m, 4H) 5.61 (s, 2H) 6.72 (t, J=76 Hz, 1H) 7.26 (d, J=11.25 Hz, 1H).

B. Synthesis of Intermediates of Formula XI

B.1. Synthesis of 6,7-dichloro-1H-indole XI-1

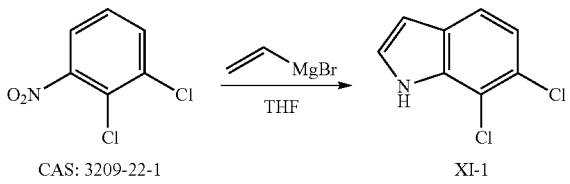

To a solution of 1,2-dichloro-3-nitro-benzene (4.00 g, 20.8 mmol) in THF (60 mL) was added vinyl magnesium bromide (1 M, 83.3 mL, 83.3 mmol) at −78° C. and the reaction mixture was stirred at same temperature for 3 h. Progress of the reaction was monitored by TLC and LCMS. After completion, the reaction mixture was quenched with saturated NH$_4$Cl (80 mL) and extracted with EtOAc (3×100 mL). The organic layer was separated, washed with brine (100 mL), dried over anhydrous Na$_2$SO$_4$ and concentrated under vacuum. The crude obtained was purified by column chromatography (silica, 100-200 mesh, 2% EtOAc in hexanes) to afford 6,7-dichloro-1H-indole XI-1 (1.50 g) as an off-white solid.

Yield: 37%.

Basic LCMS Method 2 (ES$^+$): 186 (M+H)$^+$, 95% purity.

$^1$H NMR (400 MHz, DMSO-d$_6$) δ 6.56-6.57 (m, 1H), 7.30 (d, J=8.4 Hz, 1H), 7.43 (t, J=2.4 Hz, 1H), 7.48 (d, J=8.4 Hz, 1H), 11.62 (brs, 1H).

B.2. Synthesis of 6-chloro-7-cyclopropoxy-1H-indole XI-2

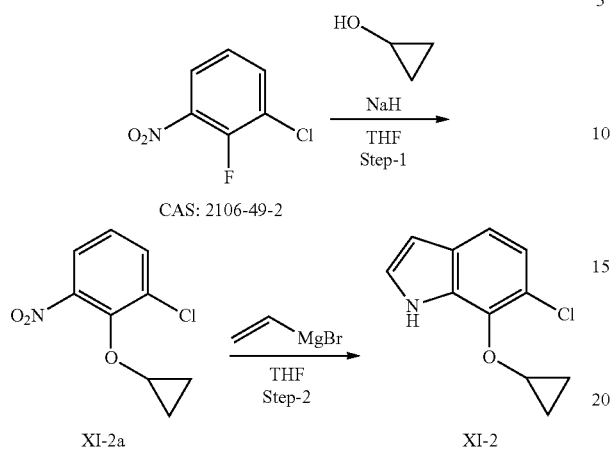

Step-1: Synthesis of 1-chloro-2-cyclopropoxy-3-nitrobenzene XI-2a

To a stirred suspension of NaH (0.91 g, 22.8 mmol) in THF (30 mL) was added cyclopropanol (1.08 mL, 17.1 mmol) in an inert atmosphere at 0° C. and the reaction mixture was stirred at same temperature for 30 min. A solution of 1-chloro-2-fluoro-3-nitro-benzene (2.00 g, 11.4 mmol) in THF (10 mL) was added drop wise at 0° C. and the reaction mixture was heated at 75° C. for 3 h. Progress of the reaction was monitored by TLC. After completion, the reaction mixture was cooled at room temperature, poured in to crushed ice and extracted with EtOAc (2×80 mL). The organic layer was separated, washed with H$_2$O (60 mL), dried over anhydrous Na$_2$SO$_4$ and concentrated under vacuum. The crude obtained was purified by column chromatography (silica, 100-200 mesh, 10% EtOAc in hexanes) to afford 1-chloro-2-cyclopropoxy-3-nitrobenzene XI-2a (1.20 g) as a pale yellow oil.

Yield: 49%.

$^1$H NMR (400 MHz, DMSO-d$_6$) δ 0.60-0.66 (m, 2H), 0.72-0.77 (m, 2H), 4.28-4.33 (m, 1H), 7.35-7.39 (m, 1H), 7.85-7.92 (m, 2H).

Step-2: Synthesis of 6-chloro-7-cyclopropoxy-1H-indole XI-2

To a solution of 1-chloro-2-cyclopropoxy-3-nitrobenzene XI-2a (1.15 g, 5.38 mmol) in THF (22 mL) was added vinyl magnesium bromide (1 M, 21.5 mL, 21.5 mmol) drop wise at −78° C. and the reaction mixture was stirred at same temperature for 2 h. Progress of the reaction was monitored by TLC. After completion, the reaction mixture was quenched with saturated NH$_4$Cl (70 mL) and extracted with EtOAc (3×40 mL). The organic layer was separated, dried over anhydrous Na$_2$SO$_4$ and concentrated under vacuum. The reaction was repeated on 0.92 g and the crude obtained from 2 reactions was clubbed and purified by column chromatography (silica, 100-200 mesh, 10% EtOAc in hexanes) to afford 6-chloro-7-cyclopropoxy-1H-indole XI-2 (0.69 g) as a pale yellow liquid.

Yield: 41%.

Basic LCMS Method 2 (ES$^+$): 208 (M+H)$^+$, 91% purity.

$^1$H NMR (400 MHz, DMSO-d$_6$) δ 0.52-0.61 (m, 2H), 0.87-0.95 (m, 2H), 4.39-4.43 (m, 1H), 6.46-6.49 (m, 1H), 6.99 (d, J=8.31 Hz, 1H), 7.30 (d, J=8.31 Hz, 1H), 7.34-7.37 (m, 1H), 11.35 (brs, 1H).

B.3. Synthesis of 6-chloro-7-(difluoromethyl)-1-(phenylsulfonyl)-1H-indole XI-3

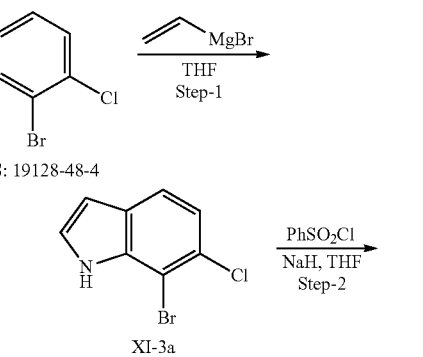

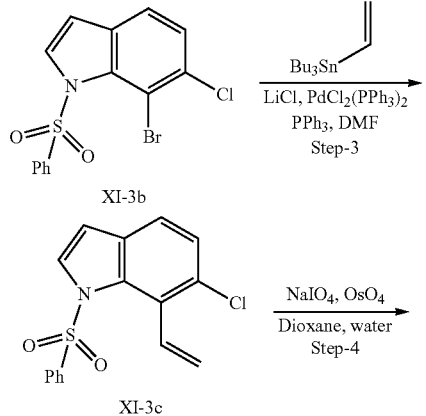

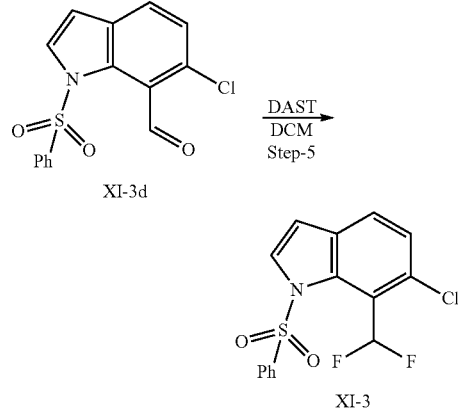

Step-1: Synthesis of 7-bromo-6-chloro-1H-indole XI-3a

To a solution of 2-bromo-1-chloro-3-nitro-benzene (4.50 g, 19.0 mmol) in THF (90 mL) was added vinyl magnesium bromide (9.99 g, 76.1 mmol) dropwise at −78° C. and the reaction mixture was stirred at the same temperature for 2 h. Progress of the reaction was monitored by TLC and LCMS. The reaction was repeated at 4.5 g scale and the crude mixture of 2 reactions was clubbed. After completion, the reaction mixture was quenched with saturated NH$_4$Cl (500 mL), diluted with H$_2$O (500 mL) and extracted with EtOAc (1000 mL). The organic layer was separated, dried over anhydrous Na$_2$SO$_4$ and concentrated under vacuum. The crude obtained was purified by column chromatography (silica, 100-200 mesh, 2% EtOAc in hexanes) to afford 7-bromo-6-chloro-1H-indole XI-3a (3.05 g) as a yellow solid.

Yield: 33%

Basic LCMS Method 2 (ES$^-$): 228 (M–H)$^-$, 96% purity.
$^1$H NMR (400 MHz, DMSO-d$_6$) δ 6.59 (d, J=1.96 Hz, 1H) 7.18 (d, J=8.31 Hz, 1H) 7.41-7.45 (m, 1H) 7.57 (d, J=8.31 Hz, 1H) 11.48 (brs, 1H)

Step-2: Synthesis of 7-bromo-6-chloro-1-(phenylsulfonyl)-1H-indole XI-3b

To a stirred suspension of NaH (2.42 g, 60.5 mmol) in dry THF (30 mL) was added 7-bromo-6-chloro-1H-indole XI-3a (7.00 g, 30.2 mmol) portion wise at 0° C. and the reaction mixture was stirred for 20 min. A solution of phenylsulfonyle chloride (5.79 mL, 45.4 mmol) in THF (10 mL) was added drop wise and the reaction mixture was stirred at room temperature for 16 h. Progress of reaction was monitored by TLC and LCMS. After completion, the reaction mixture was diluted with EtOAc (30 mL) and washed with saturated NaHCO$_3$ solution (25 mL). The organic layer was separated, dried over anhydrous Na$_2$SO$_4$ and concentrated under vacuum. The organic crude obtained was purified by column chromatography (silica, 100-200 mesh, 20% EtOAc in hexanes) to afford 7-bromo-6-chloro-1-(phenylsulfonyl)-1H-indole XI-3b (7.50 g) as an off-white solid.

Yield: 54%

Basic LCMS Method 2 (ES$^+$): 370 (M+H)$^+$, 81% purity.
$^1$H NMR (400 MHz, DMSO-d$_6$) δ 6.88 (d, J=3.42 Hz, 1H), 7.44 (d, J=8.80 Hz, 1H), 7.58-7.64 (m, 3H), 7.70-7.75 (m, 1H), 7.87 (d, J=3.42 Hz, 1H), 8.01 (d, J=7.82 Hz, 2H).

Step-3: Synthesis of 6-chloro-1-(phenylsulfonyl)-7-vinyl-1H-indole XI-3c

To a solution of 7-bromo-6-chloro-1-(phenylsulfonyl)-1H-indole XI-3b (4.00 g, 8.72 mmol) in DMF (15 mL) was added tributyl(vinyl)stannane (3.07 mL, 10.5 mmol), triphenylphosphine (0.11 g, 0.44 mmol) and LiCl (1.11 g, 26.2 mmol) and the reaction mixture was purged with argon for 10 min. PdCl$_2$(PPh$_3$)$_2$ (0.31 g, 0.44 mmol) was added and the reaction mixture was heated in sealed tube at 100° C. for 16 h. Progress of the reaction was monitored by TLC. After completion, the reaction mixture was filtered through a pad of celite and washed with EtOAc (2×40 mL). The filtrate was washed with brine (20 mL), dried over anhydrous Na$_2$SO$_4$ and concentrated under vacuum. The crude obtained was purified by column chromatography (silica, 100-200 mesh, 20% EtOAc in hexanes) to afford 6-chloro-1-(phenylsulfonyl)-7-vinyl-1H-indole XI-3c (2.80 g) as a pale yellow solid.

Yield: 98%

$^1$H NMR (400 MHz, DMSO-d$_6$) δ 4.88 (d, J=18.10 Hz, 1H), 5.29 (d, J=12.23 Hz, 1H), 6.81-6.89 (m, 1H), 6.93 (d, J=3.91 Hz, 1H), 7.39 (d, J=8.31 Hz, 1H), 7.54-7.63 (m, 3H), 7.70 (d, J=7.34 Hz, 1H), 7.74 (d, J=7.83 Hz, 2H), 7.93 (d, J=3.42 Hz, 1H).

Step-4: Synthesis of 6-chloro-1-(phenylsulfonyl)-1H-indole-7-carbaldehyde XI-3d To a solution of 6-chloro-1-(phenylsulfonyl)-7-vinyl-1H-indole XI-3c (2.50 g, 7.63 mmol) in THF (20 mL) and H$_2$O (5 mL) was added OsO$_4$ (0.04 M in water, 3.77 mL, 0.15 mmol) at and the reaction mixture was stirred for 30 min. NaIO$_4$ (4.08 g, 19.1 mmol) was added at 0° C. and the reaction mixture was stirred at room temperature for 4 h. Progress of the reaction was monitored by TLC. After completion, the reaction mixture was filtered through a pad of celite, washed with EtOAc (2×20 mL). The filtrate was washed with brine (20 mL), dried over anhydrous Na$_2$SO$_4$ and concentrated under vacuum. The crude obtained was purified by column chromatography (silica, 100-200 mesh, 20% EtOAc in hexanes) to afford 6-chloro-1-(phenylsulfonyl)-1H-indole-7-carbaldehyde XI-3d (0.60 g) as a pale yellow solid.

Yield: 24%

$^1$H NMR (400 MHz, DMSO-d$_6$) δ 7.01 (d, J=3.91 Hz, 1H), 7.48 (d, J=8.31 Hz, 1H), 7.56-7.62 (m, 2H), 7.68-7.75 (m, 3H), 7.78 (d, J=8.80 Hz, 1H), 7.93 (d, J=3.91 Hz, 1H), 10.43 (s, 1H).

Step-5: Synthesis of 6-chloro-7-(difluoromethyl)-1-(phenylsulfonyl)-1H-indole XI-3

To a solution of 6-chloro-1-(phenylsulfonyl)-1H-indole-7-carbaldehyde XI-3d (0.60 g, 1.84 mmol) in DCM (15 mL) was added diethylaminosulfur fluoride (1.06 mL, 7.36 mmol) at and the reaction mixture was stirred at room temperature for 16 h. Progress of the reaction was monitored by TLC. After completion, the reaction mixture was poured into ice H$_2$O (15 mL), basified with saturated NaHCO$_3$ solution (15 mL) and extracted with EtOAc (2×20 mL). The organic layer was separated, washed with brine (15 mL), dried over anhydrous Na$_2$SO$_4$ and concentrated under vacuum. The crude obtained was purified by column chromatography (silica, 100-200 mesh, 20% EtOAc in hexanes) to afford 6-chloro-7-(difluoromethyl)-1-(phenylsulfonyl)-1H-indole XI-3 (0.55 g) as an off-white solid.

Yield: 81%

$^1$H NMR (400 MHz, CDCl$_3$) δ 6.67 (d, J=3.91 Hz, 1H), 7.35-7.44 (m, 4H), 7.50-7.55 (m, 1H), 7.58 (d, J=8.31 Hz, 2H), 7.62 (d, J=3.42 Hz, 1H), 7.86 (t, J=52 Hz, 1H).

B.4. Synthesis of 6-chloro-7-fluoro-1H-indole XI-4

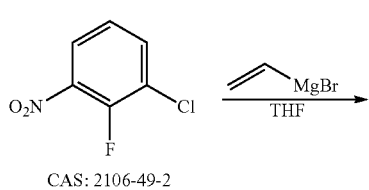

CAS: 2106-49-2

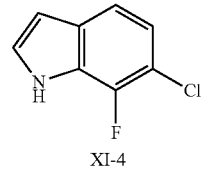

XI-4

To a solution of 1-chloro-2-fluoro-3-nitro-benzene (2.50 g, 14.2 mmol) in THF (50 mL) was added vinyl magnesium bromide (5.61 g, 42.7 mmol) at −78° C. and the reaction mixture was stirred at same temperature for 1 h. Progress of the reaction was monitored by TLC and LCMS. After completion, the reaction mixture was quenched with saturated NH$_4$Cl (100 mL), diluted with H$_2$O (400 mL) and extracted with EtOAc (500 mL). The organic layer was separated, dried over anhydrous Na₂SO₄ and concentrated under vacuum. The crude obtained was purified by column chromatography (silica, 100-200 mesh, 5% EtOAc in hexanes) to afford afford 6-chloro-7-fluoro-1H-indole XI-4 (0.60 g) as a red liquid.

Yield: 17%

Basic LCMS Method 2 (ES⁻): 168 (M−H)⁻, 66% purity.

B.5. Synthesis of 6-(difluoromethyl)-7-fluoro-1H-indole XI-5

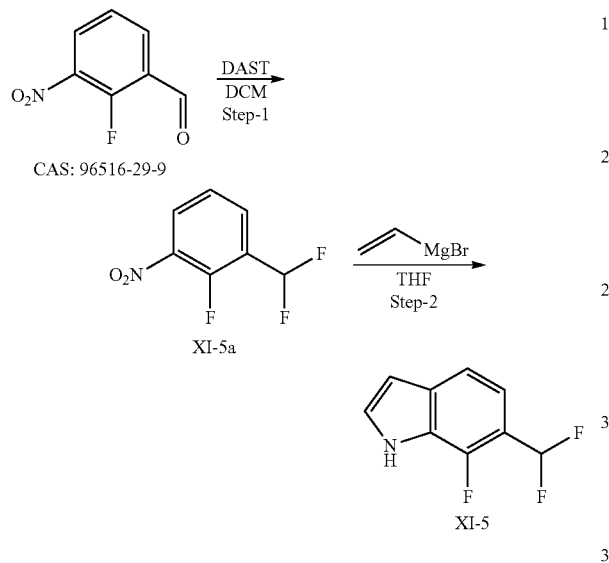

Step-1: Synthesis of 1-(difluoromethyl)-2-fluoro-3-nitro-benzene XI-5a

To a solution of 2-fluoro-3-nitro-benzaldehyde (2.0 g, 11.8 mmol) in DCM (20 mL) was added diethylaminosulfur fluoride (7.63 g, 47.3 mmol) at 0° C. and the reaction mixture was stirred at room temperature for 4 h. Progress of the reaction was monitored by TLC. After completion, the reaction mixture was poured into ice cold saturated NaHCO₃ solution (50 mL) and extracted with DCM (2×200 mL). The organic layer was separated, washed with brine (15 mL), dried over anhydrous Na₂SO₄ and concentrated under vacuum to afford 1-(difluoromethyl)-2-fluoro-3-nitro-benzene XI-5a (2.23 g) as a pale brown liquid.

This compound was used as such for the next reaction without further purification.

Yield: 96%

¹H NMR (400 MHz, DMSO-d₆) δ 7.35 (t, J=52 Hz, 1H), 7.60 (t, J=8.07 Hz, 1H), 8.05 (t, J=6.85 Hz, 1H), 8.35 (t, J=7.82 Hz, 1H).

Step-2: Synthesis of 6-(difluoromethyl)-7-fluoro-1H-indole XI-5

To a solution of 1-(difluoromethyl)-2-fluoro-3-nitro-benzene XI-5a (2.21 g, 11.2 mmol) in THF (20 mL) was added vinyl magnesium bromide (1M solution in THF, 45 mL, 45 mmol) at 0° C. and the reaction mixture was stirred at same temperature for 3 h. Progress of the reaction was monitored by TLC and LCMS. After completion, the reaction mixture was quenched with saturated NH₄Cl (40 mL) at 0° C. and extracted with EtOAc (2×200 mL). The organic layer was washed with brine (30 mL), dried over anhydrous Na₂SO₄ and concentrated under vacuum. The crude obtained was purified by column chromatography (silica, 100-200 mesh, 10% EtOAc in hexanes) to afford afford 6-(difluoromethyl)-7-fluoro-1H-indole XI-5 (0.54 g) as a brown oil.

Yield: 25%

Basic LCMS Method 2 (ES⁻): 184 (M−H)⁻, 95% purity.
¹H NMR (400 MHz, DMSO-d₆) δ 6.57-6.62 (m, 1H), 7.14-7.17 (m, 1H), 7.29 (t, J=56 Hz 1H), 7.48 (d, J=8.19 Hz, 1H), 7.56 (t, J=2.69 Hz, 1H), 11.94 (br s, 1H).

B.6. Synthesis of 1-(benzenesulfonyl)-7-chloro-6-(difluoromethyl)indole XI-6

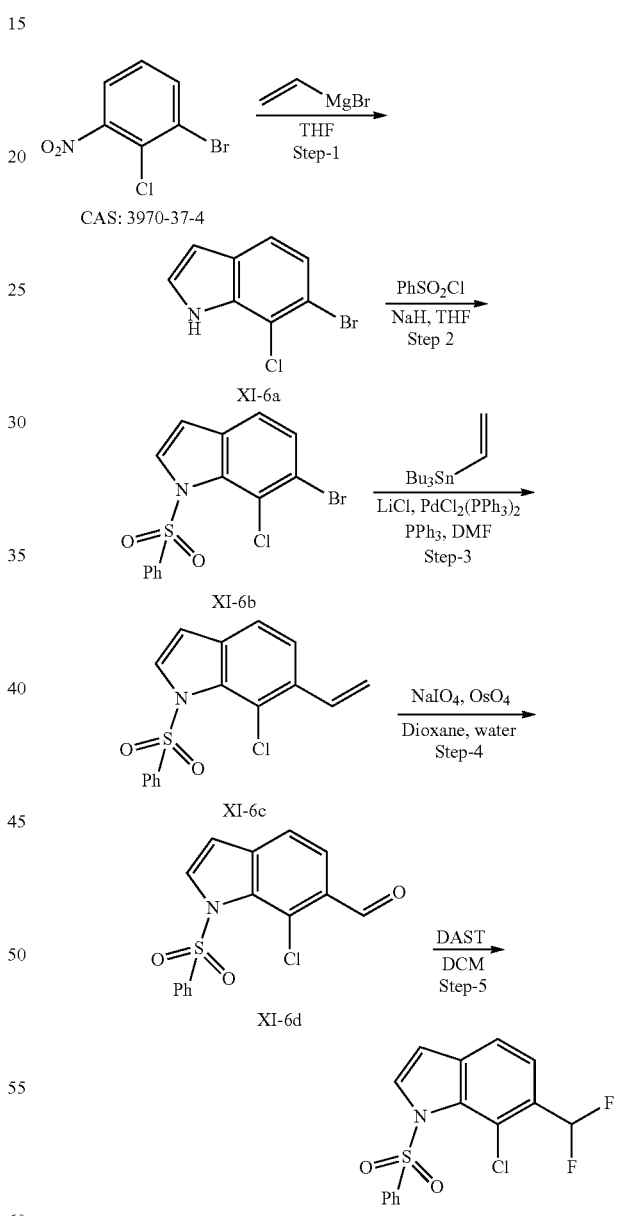

Step-1: Synthesis of 6-bromo-7-chloro-1H-indole XI-6a

To a solution of 1-bromo-2-chloro-3-nitro-benzene (5.0 g, 21.1 mmol) in THF (80 mL) was added vinyl magnesium bromide (1M solution in THF, 84.6 mL, 84.6 mmol) dropwise at −78° C. and the reaction mixture was stirred at the same temperature for 3 h. Progress of the reaction was monitored by TLC and LCMS. After completion, the reaction mixture was quenched with saturated NH₄Cl (30 mL) and extracted with EtOAc (3×100 mL). The organic layer was separated, washed with brine (70 mL), dried over anhydrous Na₂SO₄ and concentrated under vacuum. The crude obtained was purified by column chromatography (silica, 100-200 mesh, 3 to 5% EtOAc in hexanes) to afford 6-bromo-7-chloro-1H-indole XI-6a (2.5 g) as a yellow solid.

Yield: 49%

Basic LCMS Method 2 (ES⁻): 228 (M−H)⁻, 96% purity.

Step-2: Synthesis of 6-bromo-7-chloro-1-(phenylsulfonyl)-1H-indole XI-6b

To a stirred suspension of NaH (0.87 g, 21.7 mmol) in dry THF (30 mL) was added 6-bromo-7-chloro-1H-indole XI-6a (2.5 g, 10.8 mmol) portion wise at 0° C. and the reaction mixture was stirred for 10 min. Phenylsulfonyle chloride (2.3 g, 13 mmol) was added drop wise at 0° C. and the reaction mixture was stirred at room temperature for 2 h. Progress of reaction was monitored by TLC and LCMS. After completion, the reaction mixture was poured in ice cold water (100 mL) and extracted with EtOAc (3×50 mL). The organic layer was separated, dried over anhydrous Na₂SO₄ and concentrated under vacuum to afford 6-bromo-7-chloro-1-(phenylsulfonyl)-1H-indole XI-6b (3.0 g) as a pale brown solid.

This compound was used as such for the next reaction without further purification.

Yield: 71%

Basic LCMS Method 2 (ES⁻): 368 (M−H)⁻, 95% purity.

Step-3: Synthesis of 7-chloro-1-(phenylsulfonyl)-6-vinyl-1H-indole XI-6c

To a solution of 6-bromo-7-chloro-1-(phenylsulfonyl)-1H-indole XI-6b (1.5 g, 3.86 mmol) in DMF (10 mL) was added tributyl(vinyl)stannane (1.47 g, 4.63 mmol), triphenylphosphine (50 mg, 0.19 mmol) and LiCl (0.49 g, 11.6 mmol) and the reaction mixture was purged with argon for 10 min. PdCl₂(PPh₃)₂ (0.13 g, 0.19 mmol) was added and the reaction mixture was heated in sealed tube at 100° C. for 16 h. Progress of the reaction was monitored by TLC. After completion, the reaction mixture was filtered through a pad of celite and washed with EtOAc (2×100 mL). The filtrate was washed with brine (100 mL), dried over anhydrous Na₂SO₄ and concentrated under vacuum. The crude obtained was purified by column chromatography (silica, 100-200 mesh, 20% EtOAc in hexanes) to afford 7-chloro-1-(phenylsulfonyl)-6-vinyl-1H-indole XI-6c (0.80 g) as an off-white solid.

Yield: 64%

Basic LCMS Method 2 (ES⁺): 318 (M+H)⁺, 98% purity.

Step-4: Synthesis of 1-(benzenesulfonyl)-7-chloro-indole-6-carbaldehyde XI-6d

To a solution of 7-chloro-1-(phenylsulfonyl)-6-vinyl-1H-indole XI-6c (1.40 g, 4.19 mmol) in THF (70 mL) and H₂O (15 mL) was added OsO₄ (0.04 M in water, 2.07 mL, 0.08 mmol) at 0° C. and the reaction mixture was stirred for 3 hours. NaIO₄ (2.69 g, 12.6 mmol) was added at 0° C. and the reaction mixture was stirred at room temperature for 8 h. Progress of the reaction was monitored by TLC. After completion, the reaction mixture was diluted with water (100 mL). The precipitated was filtered and dried under vacuum to afford 1-(benzenesulfonyl)-7-chloro-indole-6-carbaldehyde XI-6d (1.30 g) as a brown solid.

This compound was used as such for the next reaction without further purification.

Yield: 82%

Basic LCMS Method 2 (ES⁺): 320 (M+H)⁺, 82% purity.

Step-5: Synthesis of 1-(benzenesulfonyl)-7-chloro-6-(difluoromethyl)indole XI-6

To a solution of 1-(benzenesulfonyl)-7-chloro-indole-6-carbaldehyde XI-6d (1.20 g, 3.1 mmol) in DCM (30 mL) was added diethylaminosulfur fluoride (1.78 mL, 12.4 mmol) at and the reaction mixture was stirred at room temperature for 4 h. Progress of the reaction was monitored by TLC. After completion, the reaction mixture was poured into ice H₂O (50 mL), basified with a saturated NaHCO₃ solution (40 mL) and extracted with EtOAc (2×50 mL). The organic layer was separated, washed with brine (50 mL), dried over anhydrous Na₂SO₄ and concentrated under vacuum. The crude obtained was purified by column chromatography (silica, 100-200 mesh, 20% EtOAc in hexanes) to afford 1-(benzenesulfonyl)-7-chloro-6-(difluoromethyl) indole XI-6 (0.65 g) as an off-white solid.

Yield: 60%

Basic LCMS Method 2 (ES⁻): 340 (M−H)⁻, 97% purity.

B.7. Synthesis of 6-chloro-7-(trifluoromethoxy)-1H-indole XI-7:

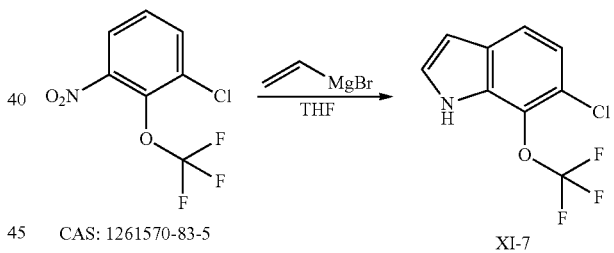

To a solution of 1-chloro-3-nitro-2-(trifluoromethoxy) benzene (2.10 g, 8.69 mmol) in THF (30 mL) was added vinyl magnesium bromide (1 M in THF, 34.8 mL, 34.8 mmol) drop wise at −78° C. and the reaction mixture was stirred at same temperature for 3 h. The reaction mixture was further stirred at room temperature for 16 h. Progress of the reaction was monitored by TLC and LCMS. After completion, the reaction mixture was quenched with saturated NH₄Cl (100 mL) and extracted with EtOAc (3×80 mL). The organic layer was separated, dried over anhydrous Na₂SO₄ and concentrated under vacuum. The crude obtained was purified by column chromatography (silica, 100-200 mesh, 2 to 4% EtOAc in hexanes) to afford 6-chloro-7-(trifluoromethoxy)-1H-indole XI-7 (1.10 g) as a pale yellow liquid.

Yield: 49%.

Basic LCMS Method 2 (ES⁻): 234 (M−H)⁻, 92% purity.

¹H NMR (400 MHz, DMSO-d₆) δ 6.61 (t, J=2.4 Hz, 1H) 7.15 (d, J=8.0 Hz, 1H) 7.54 (t, J=2.4 Hz, 1H) 7.62 (d, J=8.8 Hz, 1H) 11.8 (brs, 1H).

C. Synthesis of Intermediates of Formula XII

C.1. Method A. Synthesis of 6,7-dichloro-1H-indole-3-sulfonyl Chloride XII-1

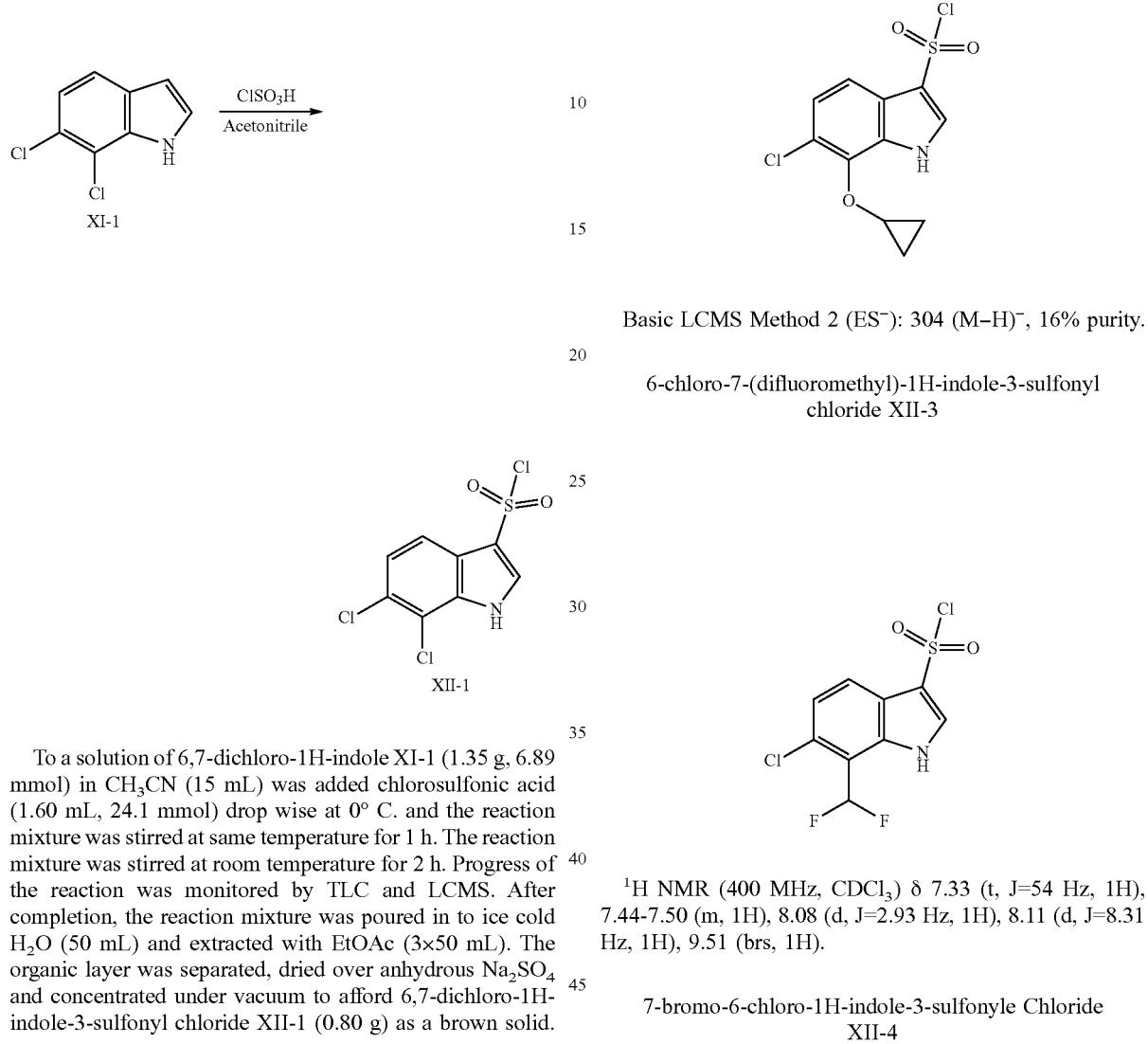

To a solution of 6,7-dichloro-1H-indole XI-1 (1.35 g, 6.89 mmol) in CH$_3$CN (15 mL) was added chlorosulfonic acid (1.60 mL, 24.1 mmol) drop wise at 0° C. and the reaction mixture was stirred at same temperature for 1 h. The reaction mixture was stirred at room temperature for 2 h. Progress of the reaction was monitored by TLC and LCMS. After completion, the reaction mixture was poured in to ice cold H$_2$O (50 mL) and extracted with EtOAc (3×50 mL). The organic layer was separated, dried over anhydrous Na$_2$SO$_4$ and concentrated under vacuum to afford 6,7-dichloro-1H-indole-3-sulfonyl chloride XII-1 (0.80 g) as a brown solid.

This compound was used as such for the next reaction without further purification.

Yield: 39%.

Basic LCMS Method 2 (ES$^-$): 282 (M−H)$^-$, 50% purity.

The following intermediates in Table 4 may be synthesized according a method analogous to Method A.

TABLE 4

| No | Indoles XI | Conditions, Time | Yield (%) |
|---|---|---|---|
| XII-2 | XI-2 | rt, 2 h | 25 |
| XII-3 | XI-3 | rt, 2 h | crude |
| XII-4 | XI-3a | rt, 2 h | crude |
| XII-5 | XI-5 | rt, 2 h | 43 |
| XII-6 | XI-6 | rt, 2 h | crude |

6-chloro-7-cyclopropoxy-1H-indole-3-sulfonyl Chloride XII-2

Basic LCMS Method 2 (ES$^-$): 304 (M−H)$^-$, 16% purity.

6-chloro-7-(difluoromethyl)-1H-indole-3-sulfonyl chloride XII-3

$^1$H NMR (400 MHz, CDCl$_3$) δ 7.33 (t, J=54 Hz, 1H), 7.44-7.50 (m, 1H), 8.08 (d, J=2.93 Hz, 1H), 8.11 (d, J=8.31 Hz, 1H), 9.51 (brs, 1H).

7-bromo-6-chloro-1H-indole-3-sulfonyle Chloride XII-4

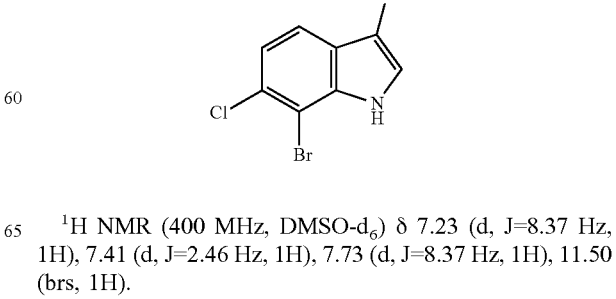

$^1$H NMR (400 MHz, DMSO-d$_6$) δ 7.23 (d, J=8.37 Hz, 1H), 7.41 (d, J=2.46 Hz, 1H), 7.73 (d, J=8.37 Hz, 1H), 11.50 (brs, 1H).

6-(difluoromethyl)-7-fluoro-1H-indole-3-sulfonyl chloride XII-5

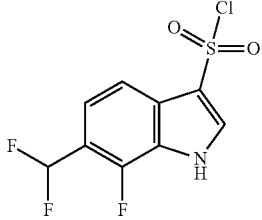

$^1$H NMR (400 MHz, DMSO-d$_6$) δ 7.17-7.21 (m, 1H), 7.29 (t, J=54 Hz 1H), 7.52 (d, J=2.45 Hz, 1H), 7.66 (d, J=8.31 Hz, 1H), 11.92 (br s, 1H).

7-chloro-6-(difluoromethyl)-1H-indole-3-sulfonyl Chloride XII-6

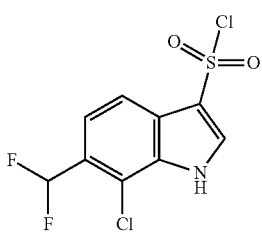 [SMILES: O=S(=O)(Cl)c1c[nH]c2c(Cl)c(C(F)F)ccc12]

crude

C.2. Synthesis of 1-(benzenesulfonyl)-6-chloro-7-fluoro-indole-3-sulfonyl Chloride XII-7

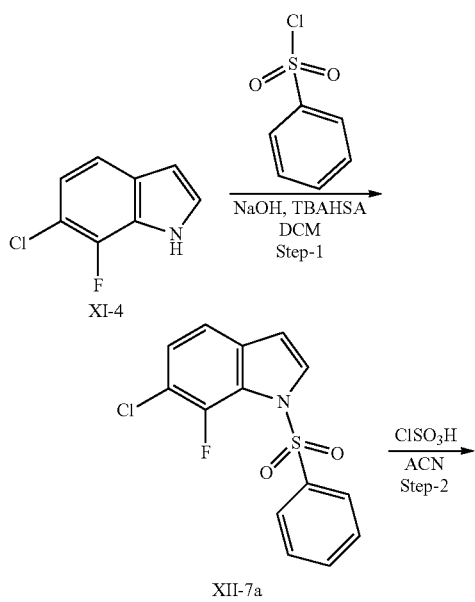

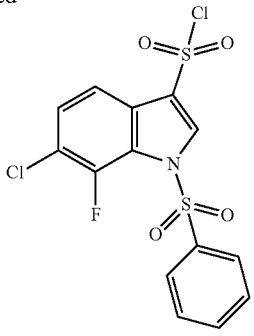

XII-7

Step-1: Synthesis of 1-(benzenesulfonyl)-6-chloro-7-fluoro-indole XII-7a

To a stirred suspension of finely powdered sodium hydroxide (3.54 g, 0.088 mol) in dichloromethane (60 mL) previously cooled on top of an ice bath was added 6-chloro-7-fluoro-1H-indole XI-4 (5 g, 0.029 mol) as a single portion followed by tetrabutylammonium hydrogen sulfate (0.501 g, 0.001 mol). Stirring was continued for a further 10 minutes then a solution of benzenesulfonyl chloride (4.2 mL, 0.033 mol) in dichloromethane (15 mL) was added dropwise over 20 minutes and the reaction mixture was stirred at 0° C. for 1 hour. The ice bath was removed and the mixture was stirred for a further 1 hour at ambient temperature. The reaction mixture was filtered over a pad of Kieselguhr, rinsing the filter cake with dichloromethane (2×50 mL). The filtrate was washed with water (4×50 mL), and brine (50 mL), dried over anhydrous sodium sulfate, filtered and the solvent concentrated under vacuum to afford 1-(benzenesulfonyl)-6-chloro-7-fluoro-indole XII-7a (8.57 g) as a dark beige solid.

Yield: 90%.

$^1$H NMR (400 MHz, DMSO-d$_6$) δ 6.95 (dd, J=3.7, 2.3 Hz, 1H), 7.37 (dd, J=8.4, 6.2 Hz, 1H), 7.48 (d, J=8.6 Hz, 1H), 7.66 (tt, J=6.9, 1.9 Hz, 2H), 7.80-7.71 (m, 1H), 7.98-7.91 (m, 2H), 7.99 (d, J=3.7 Hz, 1H).

Step-2: Synthesis of 1-(benzenesulfonyl)-6-chloro-7-fluoro-indole-3-sulfonyl Chloride XII-7

To a stirred solution of 1-(benzenesulfonyl)-6-chloro-7-fluoro-indole XII-7a (8.50 g, 0.027 mol) in acetonitrile (85 mL) previously cooled on top of an ice batch, was added chlorosulfonic acid (9.12 mL, 0.137 mol) dropwise over 20 min and the reaction mixture was stirred for 16 hours at ambient temperature. The reaction mixture was slowly poured with stirring into ice-water (340 mL) over 20 minutes. The precipitated solid was collected by filtration, rinsing the filter cake with icy water (3×50 mL) and cyclohexane (50 mL). The filter cake was then dried under a flow of nitrogen for 2 hours and then in a vacuum oven at 40° C. for 16 hours to afford 1-(benzenesulfonyl)-6-chloro-7-fluoro-indole-3-sulfonyl chloride XII-7 (7.82 g) as a light pink solid.

Yield: 66%.

Acidic LCMS Method 4 (ES$^+$): 388 (M+H)$^+$, 95% purity.

$^1$H NMR (400 MHz, DMSO-d$_6$) δ 7.44 (dd, J=8.5, 6.3 Hz, 1H), 7.72-7.61 (m, 3H), 7.80-7.72 (m, 1H), 7.81 (s, 1H), 8.05-7.98 (m, 2H).

C.3. Synthesis of 6-chloro-7-(trifluoromethoxy)-1H-indole-3-sulfonyl chloride XII-8

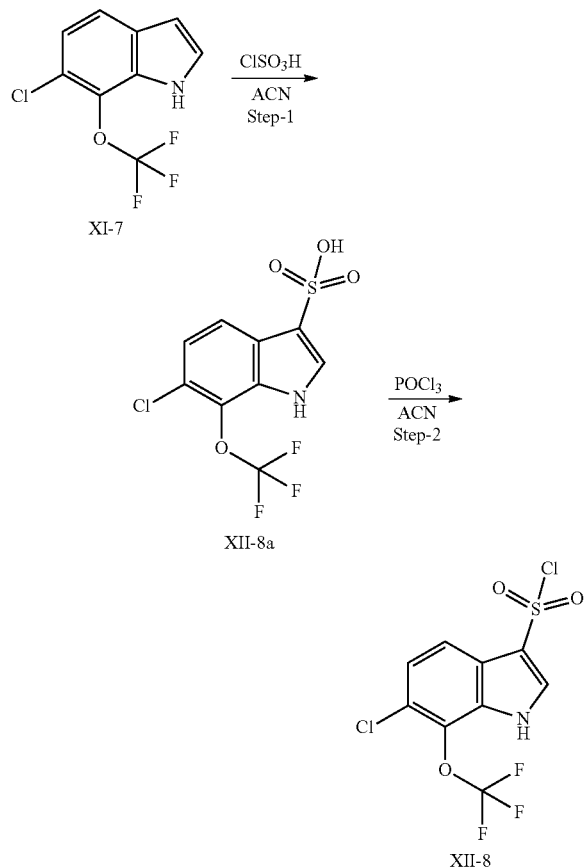

Step-1: Synthesis of 6-chloro-7-(trifluoromethoxy)-1H-indole-3-sulfonic acid XII-8a To a solution of 6-chloro-7-(trifluoromethoxy)-1H-indole XI-7 (0.10 g, 0.39 mmol) in CH₃CN (3 mL) was added ClSO₃H (0.10 mL) drop wise at 0° C. and the reaction mixture was stirred at room temperature for 3 h. Progress of the reaction was monitored by TLC and LCMS. After completion, the reaction mixture was poured into ice cold H₂O (25 mL) and extracted with EtOAc (2×20 mL). The organic layer was separated, dried over anhydrous Na₂SO₄ and concentrated under vacuum to afford 6-chloro-7-(trifluoromethoxy)-1H-indole-3-sulfonic acid XII-8a (0.11 g crude) as a pale brown liquid.

This compound was used as such for the next reaction without further purification.

Basic LCMS Method 2 (ES⁻): 314 (M–H)⁻, 91% purity.

Step-2: Synthesis of 6-chloro-7-(trifluoromethoxy)-1H-indole-3-sulfonyl chloride XII-8

To a solution of 6-chloro-7-(trifluoromethoxy)-1H-indole-3-sulfonic acid XII-8a (0.11 g, 0.28 mmol) in CH₃CN (3 mL) was added POCl₃ (0.1 mL, 1.12 mmol) at 0° C. and the reaction mixture was heated at 60° C. for 16 h. Progress of the reaction was monitored by TLC and LCMS. After completion, the reaction mixture was concentrated under vacuum. The residue was diluted with ice cold H₂O (50 mL) and extracted with EtOAc (3×40 mL). The organic layer was separated, dried over anhydrous Na₂SO₄ and concentrated under vacuum. The crude obtained (0.1 g, 0.3 mmol) was dissolved in CH₃CN (6 mL) and POCl₃ (0.11 mL, 1.22 mmol) was added drop wise at 0° C. and the reaction mixture was heated at 60° C. for 16 h. After completion, the reaction mixture was concentrated under vacuum. The residue was diluted with ice cold H₂O (60 mL) and extracted with EtOAc (3×50 mL). The organic layer was separated, dried over anhydrous Na₂SO₄ and concentrated under vacuum to afford 6-chloro-7-(trifluoromethoxy)-1H-indole-3-sulfonyl chloride XII-8 (0.13 g crude) as a brown liquid.

This compound was used as such for the next reaction without further purification Basic LCMS Method 2 (ES⁻): 332 (M–H)⁻

Example Compounds

D. Synthesis of Compounds of General Formula I

All compounds of the present invention specifically disclosed herein are designated "1-x" wherein any "x" refers to a number identifying the individual compounds. Accordingly, the Example compounds are designated 1-1, 1-2, 1-3 etc. This is irrespective of whether any compound could also be described by any subgeneric Formula herein, e.g. by Formula II, III or IV, and the like.

D.1. Method B. Synthesis of 6,7-dichloro-N-[3,6-difluoro-5-(2-fluoroethoxy)pyridin-2-yl]-1H-indole-3-sulfonamide I-1

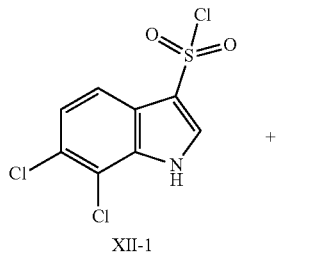

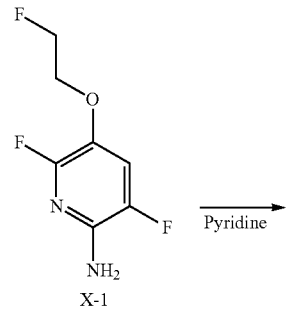

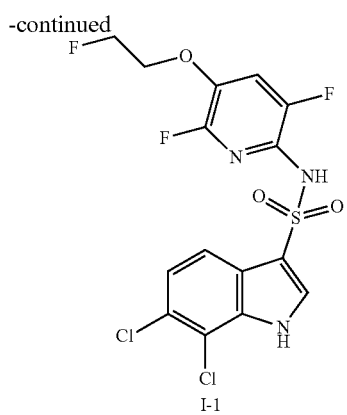

I-1

To a solution of 3,6-difluoro-5-(2-fluoroethoxy)pyridin-2-amine X-1 (0.10 g, 0.44 mmol) in pyridine (5 mL) was added 6,7-dichloro-1H-indole-3-sulfonyl chloride XII-1 (0.33 g, 1.10 mmol) portion wise at 0° C. over a period of 20 min followed by addition of DMAP (0.01 g, mmol) at same temperature. The reaction mixture was heated at 100° C. for 30 h. Progress of the reaction was monitored by TLC and LCMS. After completion, the reaction mixture was concentrated under vacuum. The residue was triturated with 2 N HCl (10 mL), diluted with $H_2O$ (20 mL) and extracted with EtOAc (3×25 mL). The organic layer was separated, washed with brine (2×30 mL), dried over anhydrous $Na_2SO_4$ and concentrated under vacuum. The crude obtained was purified by column chromatography (silica, 100-200 mesh, 30% EtOAc in hexanes) to afford 6,7-dichloro-N-[3,6-difluoro-5-(2-fluoroethoxy)pyridin-2-yl]-1H-indole-3-sulfonamide I-1 (0.065 g) as a white solid.

Yield: 34%.

Basic LCMS Method 2 (ES$^+$): 440 (M+H)$^+$, 99% purity.

$^1$H NMR (400 MHz, DMSO-d$_6$) δ 4.22-4.25 (m, 1H), 4.31-4.34 (m, 1H), 4.62-4.65 (m, 1H), 4.75-4.79 (m, 1H), 7.39 (d, J=8.80 Hz, 1H), 7.70-7.76 (m, 2H), 7.97 (s, 1H), 10.64 (brs, 1H), 12.52 (brs, 1H).

The following compounds in Table 5 may be synthesized according to a method analogous to Method B.

TABLE 5

| No | Sulfonyl chlorides XII | Amines X | Conditions, Time | Purification conditions | Yield (%) |
|---|---|---|---|---|---|
| I-2 | XII-2 | X-1 | 90° C., 16 h | 40% EtOAc/Hexane | 12 |
| I-3 | XII-3 | X-1 | DMAP cat., 90° C., 24 h | 40% EtOAc/Hexane | 17 |
| I-4 | XII-4 | X-1 | DMAP cat., 80° C., 16 h | 20% EtOAc/Hexane | 69 |
| I-5 | XII-1 | X-2 | DMAP cat., 90° C., 12 h | 60% EtOAc/Hexane | 11 |
| I-6 | XII-1 | X-3 | DMAP cat., 90° C., 12 h | 60% EtOAc/Hexane | 10 |
| I-7 | XII-3 | X-2 | DMAP cat., 90° C., 16 h | 60% EtOAc/Hexane | 20 |
| I-8 | XII-5 | X-2 | DMAP cat., 90° C., 16 h | 60% EtOAc/Hexane | 5 |
| I-9 | XII-6 | X-3 | DMAP cat., 90° C., 16 h | 60% EtOAc/Hexane | 47 |
| I-13 | XII-1 | X-5 | DMAP cat., 90° C., 2 h | 60% EtOAc/Hexane | 53 |
| I-14 | XII-3 | X-3 | DMAP cat., 90° C., 16 h | 30% EtOAc/Hexane | 34 |
| I-15 | XII-3 | X-5 | DMAP cat., 90° C., 16 h | 30% EtOAc/Hexane | 38 |
| I-16 | XII-1 | X-6 | DMAP cat., 90° C., 2 h | 60% EtOAc/Hexane | 33 |
| I-17 | XII-3 | X-6 | DMAP cat., 90° C., 16 h | 40% EtOAc/Hexane | 28 |
| I-18 | XII-8 | X-1 | 80° C., 16 h | 50-70% EtOAc/Hexane | 7 |
| I-19 | XII-5 | X-3 | DMAP cat., 80° C., 16 h | 30% EtOAc/Hexane | 2 |
| I-20 | XII-6 | X-5 | DMAP cat., 80° C., 5 h | 30% EtOAc/Hexane | 23 |
| I-21 | XII-1 | X-7 | DMAP cat., 90° C., 2 h | 60% EtOAc/Hexane | 79 |

6-chloro-7-cyclopropyloxy-N-[3,6-difluoro-5-(2-fluoroethoxy)pyridin-2-yl]-1H-indole-3-sulfonamide I-2

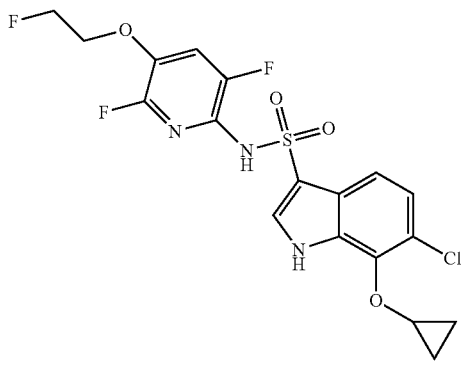 [SMILES: O=S(=O)(Nc1nc(F)c(OCCF)cc1F)c1c[nH]c2c(OC3CC3)c(Cl)ccc12]

Basic LCMS Method 2 (ES$^+$): 462 (M+H)$^+$, 99% purity.

$^1$H NMR (400 MHz, DMSO-d$_6$) δ 0.54-0.56 (m, 2H), 0.86-0.88 (m, 2H), 4.25-4.27 (m, 1H), 4.32-4.37 (m, 1H), 4.40-4.43 (m, 1H), 4.63-4.65 (m, 1H), 4.75-4.78 (m, 1H), 7.20 (d, J=8.31 Hz, 1H), 7.48 (d, J=8.80 Hz, 1H), 7.79 (s, 1H), 7.92 (s, 1H), 10.56 (brs, 1H), 12.31 (brs, 1H).

6-chloro-N-[3,6-difluoro-5-(2-fluoroethoxy)pyridin-2-yl]-7-(difluoromethyl)-1H-indole-3-sulfonamide I-3

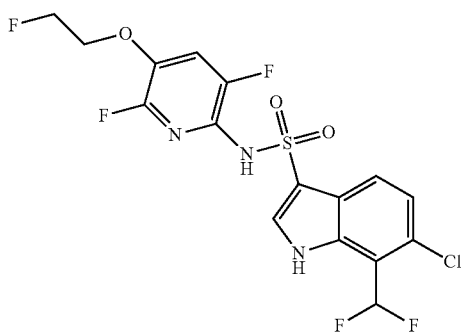 [SMILES: O=S(=O)(Nc1nc(F)c(OCCF)cc1F)c1c[nH]c2c(C(F)F)c(Cl)ccc12]

Basic LCMS Method 2 (ES$^+$): 456 (M+H)$^+$, 99% purity.

$^1$H NMR (400 MHz, DMSO-d$_6$) δ 4.27-4.32 (m, 1H), 4.35-4.41 (m, 1H), 4.64-4.69 (m, 1H), 4.74-4.80 (m, 1H), 7.38 (d, J=8.86 Hz, 1H), 7.53 (t, J=56 Hz, 1H), 7.83 (t, J=9.11 Hz, 1H), 7.90-7.96 (m, 2H), 10.65 (s, 1H), 12.28 (brs, 1H).

7-bromo-6-chloro-N-[3,6-difluoro-5-(2-fluoroethoxy)-2-pyridyl]-1H-indole-3-sulfonamide I-4

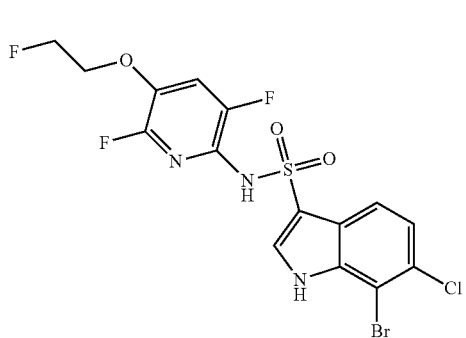 [SMILES: O=S(=O)(Nc1nc(F)c(OCCF)cc1F)c1c[nH]c2c(Br)c(Cl)ccc12]

¹H NMR (400 MHz, DMSO-d₆) δ 4.27-4.30 (m, 1H), 4.34-4.39 (m, 1H), 4.64-4.67 (m, 1H), 4.76-4.80 (m, 1H), 7.41 (d, J=8.31 Hz, 1H), 7.75 (d, J=8.80 Hz, 1H), 7.80-7.86 (m, 1H), 7.97 (d, J=2.93 Hz, 1H), 10.64 (s, 1H), 12.47 (brs, 1H).

6,7-dichloro-N-[3-fluoro-5-(2-fluoroethoxy)pyridin-2-yl]-1H-indole-3-sulfonamide I-5

Basic LCMS Method 2 (ES⁺): 422 (M+H)⁺, 99% purity.

¹H NMR (400 MHz, DMSO-d₆) δ 4.21-4.26 (m, 1H), 4.30-4.34 (m, 1H), 4.62-4.67 (m, 1H), 4.74-4.79 (m, 1H), 7.40 (d, J=8.67 Hz, 1H), 7.52 (dd, J=11.27, 2.60 Hz, 1H), 7.71 (d, J=8.67 Hz, 1H), 7.83 (d, J=2.60 Hz, 1H), 7.97 (s, 1H), 10.43 (s, 1H), 12.60 (brs, 1H).

6,7-dichloro-N-[5-(2,2-difluoroethoxy)-3-fluoropyridin-2-yl]-1H-indole-3-sulfonamide I-6

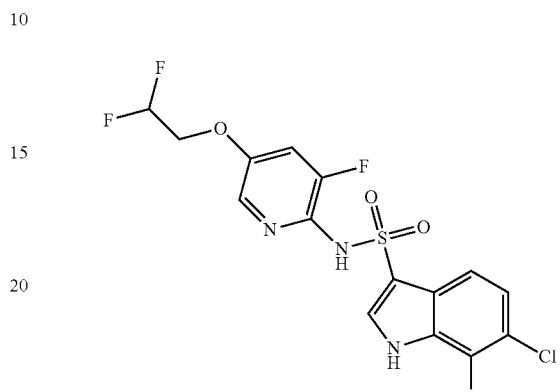

Basic LCMS Method 2 (ES⁺): 440 (M+H)⁺, 99% purity.

¹H NMR (400 MHz, DMSO-d₆) δ 4.37 (td, J=14.74, 3.47 Hz, 2H), 6.22-6.52 (m, 1H), 7.40 (d, J=8.24 Hz, 1H), 7.58 (dd, J=11.27, 2.60 Hz, 1H), 7.73 (d, J=8.67 Hz, 1H), 7.86 (d, J=2.17 Hz, 1H), 7.98 (s, 1H), 10.52 (br s, 1H), 12.61 (br s, 1H).

6-chloro-7-(difluoromethyl)-N-[3-fluoro-5-(2-fluoroethoxy)pyridin-2-yl]-1H-indole-3-sulfonamide I-7

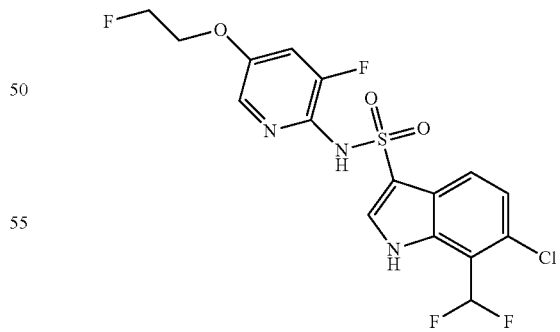

Basic LCMS Method 2 (ES⁺): 438 (M+H)⁺, 98% purity.

¹H NMR (400 MHz, DMSO-d₆) δ 4.20-4.26 (m, 1H), 4.28-4.35 (m, 1H), 4.60-4.66 (m, 1H), 4.71-4.79 (m, 1H), 7.35 (d, J=8.80 Hz, 1H), 7.48-7.50 (m, 1H), 7.52 (t, J=52 Hz, 1H), 7.82 (d, J=1.96 Hz, 1H), 7.87-7.93 (m, 2H), 10.43 (s, 1H), 12.21 (br s, 1H).

6-(difluoromethyl)-7-fluoro-N-[3-fluoro-5-(2-fluoro-ethoxy)pyridin-2-yl]-1H-indole-3-sulfonamide I-8

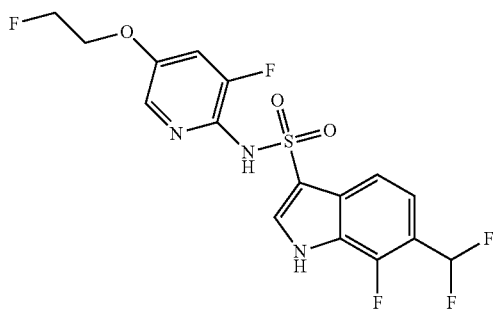 [SMILES: O=S(=O)(Nc1ncc(OCCF)cc1F)c1c[nH]c2c(F)c(C(F)F)ccc12]

Basic LCMS Method 2 (ES+): 422 (M+H)+, 98% purity.

7-chloro-N-[3-fluoro-5-(2-fluoroethoxy)pyridin-2-yl]-6-(difluoromethyl)-1H-indole-3-sulfonamide I-9

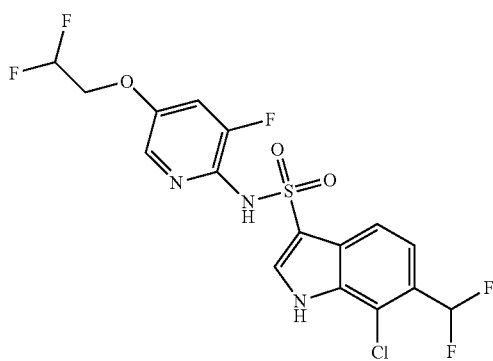 [SMILES: O=S(=O)(Nc1ncc(OCC(F)F)cc1F)c1c[nH]c2c(Cl)c(C(F)F)ccc12]

Basic LCMS Method 2 (ES+): 456 (M+H)+, 98% purity.

6,7-dichloro-N-[5-(2,2-difluoroethoxy)-3-fluoro-6-methoxypyridin-2-yl]-1H-indole-3-sulfonamide I-13

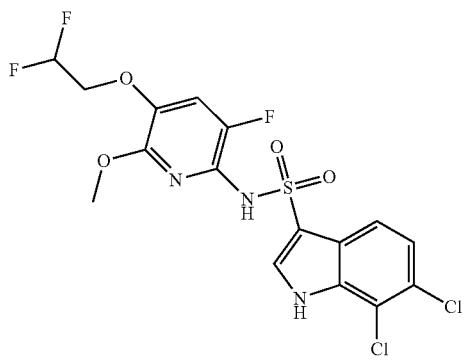 [SMILES: COc1nc(NS(=O)(=O)c2c[nH]c3c(Cl)c(Cl)ccc23)c(F)cc1OCC(F)F]

Basic LCMS Method 2 (ES+): 470 (M+H)+, 99% purity.
¹H NMR (400 MHz, DMSO-d₆) δ 3.43 (s, 3H) 4.28 (td, J=14.43, 3.42 Hz, 2H) 6.19-6.50 (m, 1H) 7.39 (d, J=8.80 Hz, 1H) 7.53 (d, J=10.27 Hz, 1H) 7.71 (d, J=8.31 Hz, 1H) 8.00 (d, J=1.96 Hz, 1H) 10.36 (brs, 1H) 12.58 (brs, 1H).

6-chloro-N-[5-(2,2-difluoroethoxy)-3-fluoropyridin-2-yl]-7-(difluoromethyl)-1H-indole-3-sulfonamide I-14

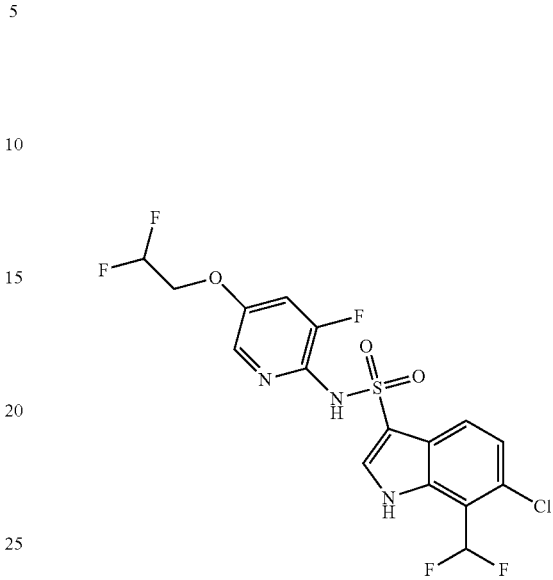

Basic LCMS Method 2 (ES+): 456 (M+H)+, 99% purity.
¹H NMR (400 MHz, DMSO-d₆) δ 4.37 (td, J=14.67, 3.42 Hz, 2H) 6.22-6.52 (m, 1H) 7.37 (d, J=8.80 Hz, 1H) 7.53 (t, J=54 Hz, 1H) 7.56-7.62 (m, 1H) 7.87 (d, J=1.96 Hz, 1H) 7.89-7.96 (m, 2H) 10.54 (s, 1H) 12.24 (brs, 1H).

6-chloro-N-[5-(2,2-difluoroethoxy)-3-fluoro-6-methoxypyridin-2-yl]-7-(difluoromethyl)-1H-indole-3-sulfonamide I-15

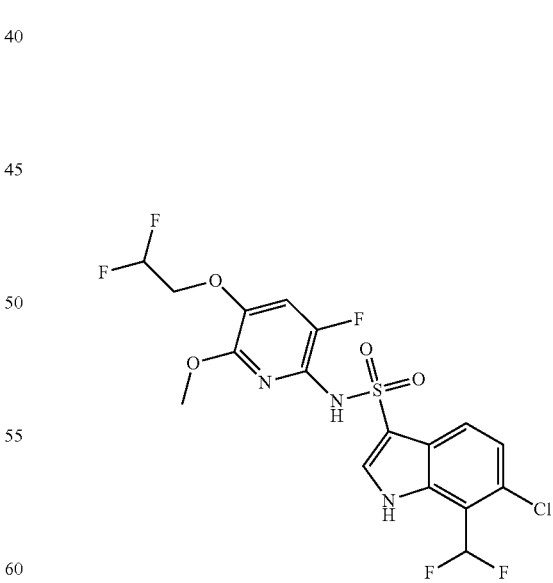

Basic LCMS Method 2 (ES+): 486 (M+H)+, 97% purity.
¹H NMR (400 MHz, DMSO-d₆) δ 3.41 (s, 3H) 4.29 (td, J=14.43, 3.42 Hz, 2H) 6.19-6.50 (m, 1H) 7.37 (d, J=8.31 Hz, 1H) 7.52-7.57 (m, 1H) 7.53 (t, J=54 Hz, 1H) 7.90-7.95 (m, 2H) 10.35 (s, 1H) 12.21 (brs, 1H).

6,7-dichloro-N-[5-(difluoromethoxy)-3-methoxy-pyridin-2-yl]-1H-indole-3-sulfonamide I-16

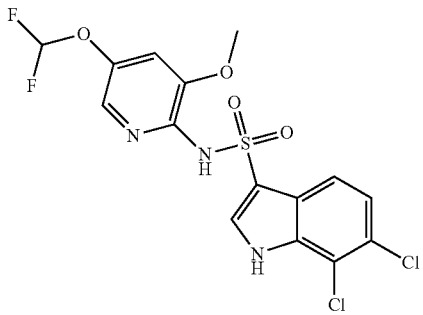 [SMILES: COc1cc(OC(F)F)cnc1NS(=O)(=O)c1c[nH]c2c(Cl)c(Cl)ccc12]

Basic LCMS Method 2 (ES⁺): 438 (M+H)⁺, 99% purity.
¹H NMR (400 MHz, DMSO-$d_6$) δ 3.78 (s, 3H) 7.16 (t, J=74 Hz, 1H) 7.25 (d, J=2.45 Hz, 1H) 7.41 (d, J=8.80 Hz, 1H) 7.62 (d, J=1.96 Hz, 1H) 7.92 (d, J=8.80 Hz, 1H) 8.09 (s, 1H) 10.28 (brs, 1H) 12.59 (brs, 1H).

6-chloro-N-[5-(difluoromethoxy)-3-methoxypyridin-2-yl]-7-(difluoromethyl)-1H-indole-3-sulfonamide I-17

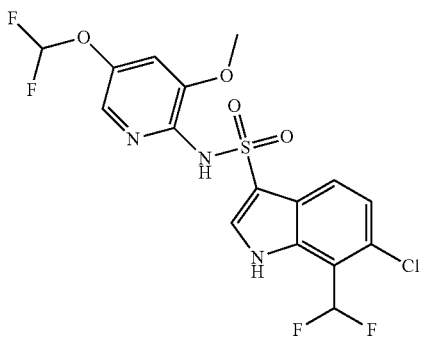 [SMILES: COc1cc(OC(F)F)cnc1NS(=O)(=O)c1c[nH]c2c(C(F)F)c(Cl)ccc12]

Basic LCMS Method 2 (ES⁺): 454 (M+H)⁺, 99% purity.
¹H NMR (400 MHz, DMSO-$d_6$) δ 3.78 (s, 3H) 7.16 (t, J=74 Hz, 1H) 7.25 (d, J=1.47 Hz, 1H) 7.39 (s, 1H) 7.52 (t, J=54 Hz, 1H) 7.62 (d, J=1.47 Hz, 1H) 8.02 (s, 1H) 8.13 (d, J=8.31 Hz, 1H) 10.30 (brs, 1H) 12.21 (brs, 1H).

6-chloro-N-[3,6-difluoro-5-(2-fluoroethoxy)pyridin-2-yl]-7-(trifluoromethoxy)-1H-indole-3-sulfonamide I-18

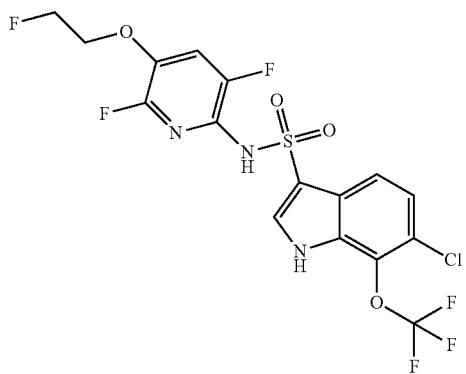 [SMILES: O=S(=O)(Nc1nc(F)c(OCCF)cc1F)c1c[nH]c2c(OC(F)(F)F)c(Cl)ccc12]

Basic LCMS Method 2 (ES⁺): 490 (M+H)⁺, 99% purity.
¹H NMR (400 MHz, DMSO-$d_6$) δ 4.23-4.25 (m, 1H) 4.31-4.33 (m, 1H) 4.61-4.67 (m, 1H) 4.73-4.79 (m, 1H) 7.36 (d, J=8.31 Hz, 1H) 7.71-7.79 (m, 1H) 7.83 (d, J=8.80 Hz, 1H) 8.05 (brs, 1H) 10.69 (s, 1H) 12.70 (brs, 1H).

N-[5-(2,2-difluoroethoxy)-3-fluoropyridin-2-yl]-6-(difluoromethyl)-7-fluoro-1H-indole-3-sulfonamide I-19

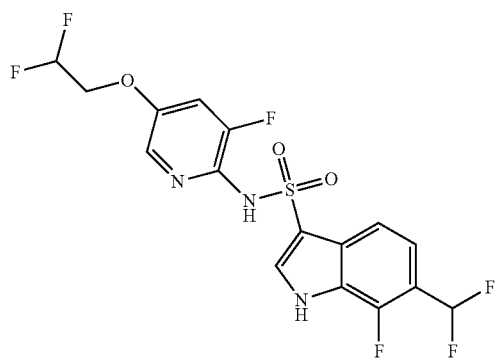 [SMILES: O=S(=O)(Nc1ncc(OCC(F)F)cc1F)c1c[nH]c2c(F)c(C(F)F)ccc12]

Basic LCMS Method 2 (ES⁺): 440 (M+H)⁺, 82% purity.
¹H NMR (400 MHz, DMSO-$d_6$) δ 4.36 (td, J=14.68, 3.47 Hz, 2H) 6.22-6.51 (m, 1H) 7.33 (t, J=54 Hz, 1H) 7.33-7.38 (m, 1H) 7.58 (dd, J=11.10, 2.31 Hz, 1H) 7.69 (d, J=8.32 Hz, 1H) 7.86 (d, J=2.31 Hz, 1H) 8.11 (s, 1H) 10.54 (brs, 1H) 12.92 (brs, 1H).

7-chloro-N-[5-(2,2-difluoroethoxy)-3-fluoro-6-methoxypyridin-2-yl]-6-(difluoromethyl)-1H-indole-3-sulfonamide I-20

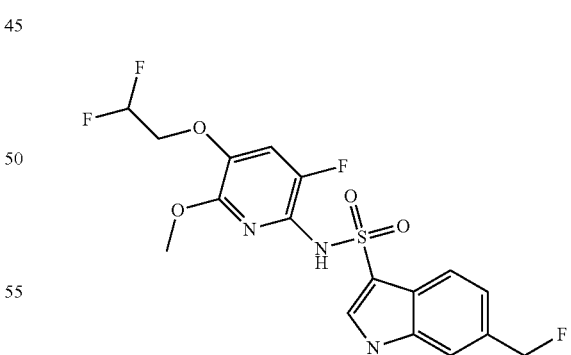

Basic LCMS Method 2 (ES⁺): 486 (M+H)⁺, 98% purity.
¹H NMR (400 MHz, DMSO-$d_6$) δ 3.41 (s, 3H) 4.28 (td, J=14.55, 3.18 Hz, 2H) 6.19-6.49 (m, 1H) 7.33 (t, J=56 Hz, 1H) 7.48 (d, J=8.80 Hz, 1H) 7.54 (d, J=10.27 Hz, 1H) 7.86 (d, J=8.31 Hz, 1H) 8.12 (s, 1H) 10.40 (brs, 1H) 12.73 (brs, 1H).

6,7-dichloro-N-[5-(2,2-difluoroethoxy)-3-methoxy-pyridin-2-yl]-1H-indole-3-sulfonamide I-21

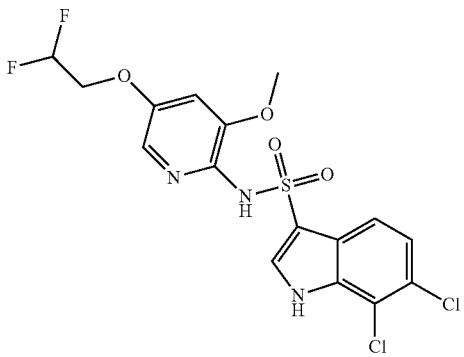 [SMILES: COc1cc(OCC(F)F)cnc1NS(=O)(=O)c1c[nH]c2c(Cl)c(Cl)ccc12]

Basic LCMS Method 2 (ES⁺): 452 (M+H)⁺, 98% purity.
$^1$H NMR (400 MHz, DMSO-d$_6$) δ 3.67 (s, 3H) 4.29 (td, J=14.67, 2.93 Hz, 2H) 6.15-6.46 (m, 1H) 7.04 (d, J=1.47 Hz, 1H) 7.36 (d, J=8.80 Hz, 1H) 7.48 (s, 1H) 7.83 (d, J=8.31 Hz, 1H) 7.96 (s, 1H) 9.89 (br s, 1H) 12.48 (brs, 1H)

D.2. Synthesis of 6-chloro-N-[3,6-difluoro-5-(2-fluoroethoxy)pyridin-2-yl]-7-fluoro-1H-indole-3-sulfonamide I-10

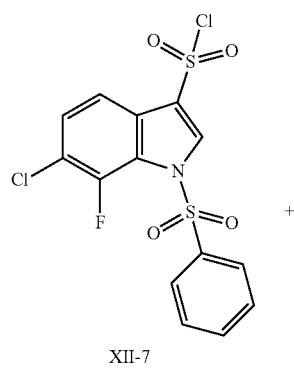
XII-7

+

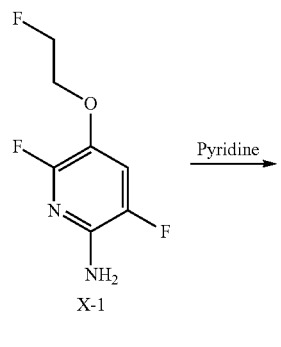
X-1

Pyridine →

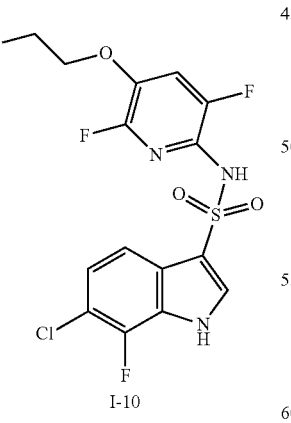
I-10

To a solution of 3,6-difluoro-5-(2-fluoroethoxy)pyridin-2-amine X-1 (50 mg, 0.26 mmol) in pyridine (1 mL), 1-(benzenesulfonyl)-6-chloro-7-fluoro-indole-3-sulfonyl chloride XII-7 (106 mg, 0.26 mmol) was added then stirred at room temperature for 3 h. The reaction mixture was evaporated to dryness and then poured into water and extracted with ethyl acetate (twice). The organic phases were dried over MgSO$_4$ and evaporated. The residue was purified by column chromatography (silica, 100-200 mesh, 0 to 10% MeOH in DCM) followed by a basic prep LCMS Method 1 to provide 6 mg of 6-chloro-N-[3,6-difluoro-5-(2-fluoroethoxy)pyridin-2-yl]-7-fluoro-1H-indole-3-sulfonamide I-10 as a pale yellow solid.

Yield: 5%.
Basic LCMS Method 1 (ES⁻): 422 (M−H)⁻, 97% purity.

D.3. Synthesis of 6-chloro-N-[5-(2,2-difluoroethoxy)-3,6-difluoropyridin-2-yl]-7-fluoro-1H-indole-3-sulfonamide I-11

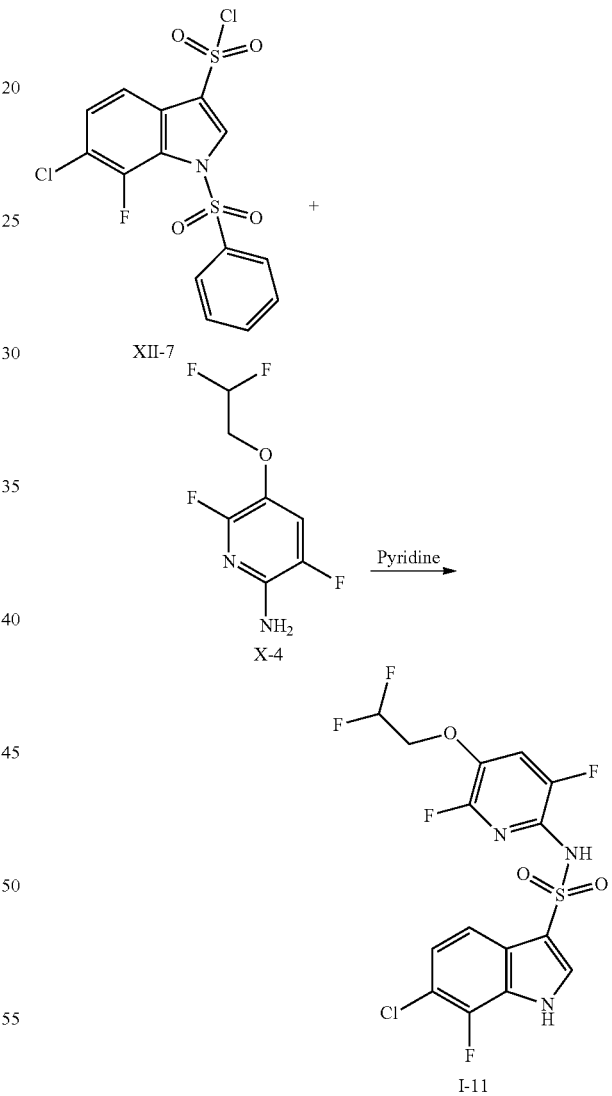

To a solution of 5-(2,2-difluoroethoxy)-3,6-difluoro pyridin-2-amine X-4 (154 mg, 0.37 mmol) in pyridine (1 mL), 1-(benzenesulfonyl)-6-chloro-7-fluoro-indole-3-sulfonyl chloride XII-7 (150 mg, 0.37 mmol) was added then stirred at 70° C. for 2 h. The reaction mixture was evaporated to dryness and then poured into water and extracted with ethyl acetate (twice). The organic phases were dried over MgSO$_4$ and evaporated. The residue was purified by column chromatography (silica, 100-200 mesh, 0 to 5% MeOH in DCM) followed by a basic prep LCMS Method 1 to provide 32 mg of 6-chloro-N-[5-(2,2-difluoroethoxy)-3,6-difluoropyridin-2-yl]-7-fluoro-1H-indole-3-sulfonamide I-11 as a pale yellow solid.

Yield: 20%.

Basic LCMS Method 1 (ES⁻): 440 (M−H)⁻, 97% purity.

¹H NMR (400 MHz, DMSO-d₆) δ 4.41 (td, J=14.6, 3.5 Hz, 2H), 6.38 (t, J=3.5 Hz, 1H), 7.31 (dd, J=8.6, 6.5 Hz, 1H), 7.58 (d, J=8.6 Hz, 1H), 7.89 (t, J=9.1 Hz, 1H), 8.06 (d, J=2.4 Hz, 1H), 10.72 (s, 1H), 12.84 (s, 1H).

D.4. Synthesis of 6-chloro-7-cyclopropyl-N-[3,6-difluoro-5-(2-fluoroethoxy)pyridin-2-yl]-1H-indole-3-sulfonamide I-12

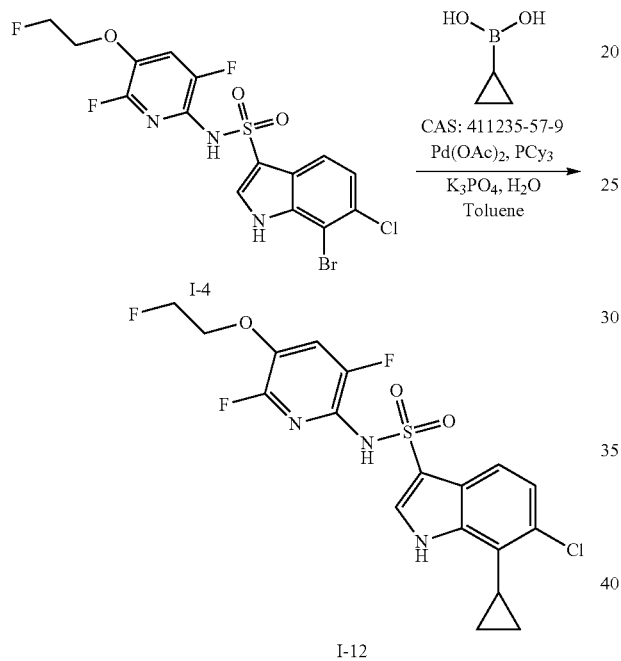

To a solution of 7-bromo-6-chloro-N-[3,6-difluoro-5-(2-fluoroethoxy)-2-pyridyl]-1H-indole-3-sulfonamide I-4 (0.25 g, 0.51 mmol) in toluene (8 mL) and H₂O (0.8 mL) was added K₃PO₄ (0.22 g, 1.01 mmol), cyclopropylboronic acid (0.07 g, 0.76 mmol) and tricyclohexyl phosphine (0.03 g, 0.10 mmol). The reaction mixture was purged with argon for 15 min followed by addition of Pd(OAc)₂ (0.01 g, 0.05 mmol). The reaction mixture was purged with argon for 5 min and heated at 100° C. for 16 h. Progress of the reaction was monitored by TLC and LCMS. After completion, the reaction mixture was filtered through a pad of celite, washed with EtOAc (100 mL). The filtrate was washed with H₂O (50 mL). The organic layer was separated, dried over anhydrous Na₂SO₄ and concentrated under vacuum. The crude obtained was purified by column chromatography (silica, 100-200 mesh, 20% EtOAc in hexanes) to afford 6-chloro-7-cyclopropyl-N-[3,6-difluoro-5-(2-fluoroethoxy)pyridin-2-yl]-1H-indole-3-sulfonamide I-12 (0.04 g) as an off-white solid.

Yield: 17%.

Basic LCMS Method 2 (ES⁺): 446 (M+H)⁺, 95% purity.

¹H NMR (400 MHz, DMSO-d₆) δ 0.68-0.70 (m, 2H), 1.09-1.17 (m, 2H), 1.93-2.00 (m, 1H), 4.25-4.29 (m, 1H), 4.32-4.37 (m, 1H), 4.62-4.67 (m, 1H), 4.74-4.79 (m, 1H), 7.19 (d, J=8.80 Hz, 1H), 7.60 (d, J=8.31 Hz, 1H), 7.77-7.84 (m, 1H), 7.87 (d, J=2.93 Hz, 1H), (s, 1H), 11.90 (brs, 1H).

D.5. Synthesis of 6-chloro-N-[5-(2,2-difluoroethoxy)-3-fluoro-6-methoxypyridin-2-yl]-7-fluoro-1H-indole-3-sulfonamide I-22

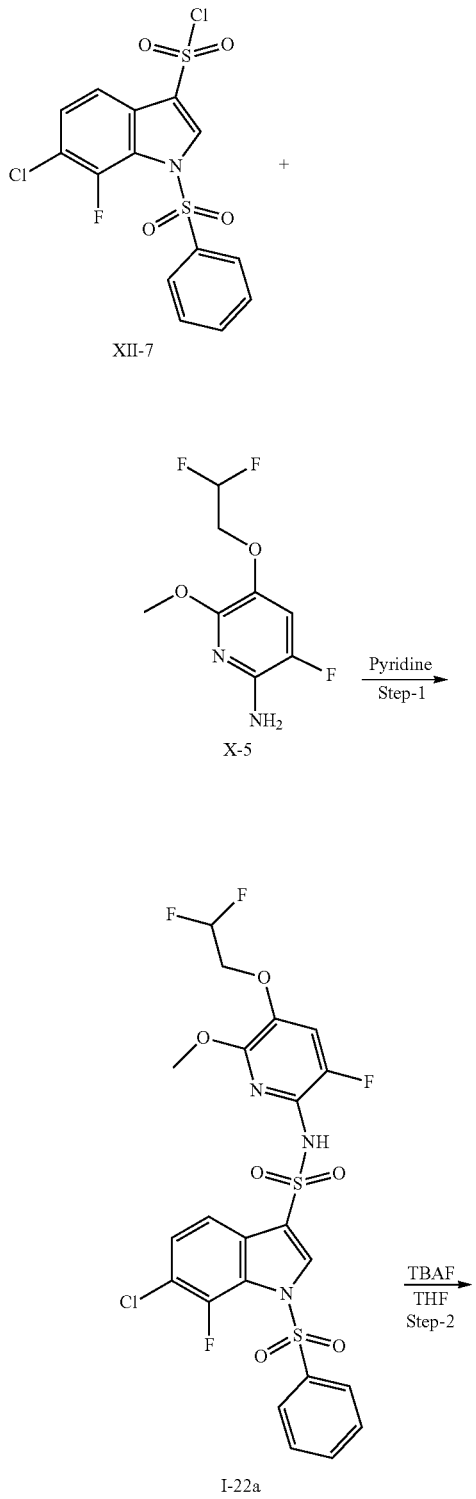

81

-continued

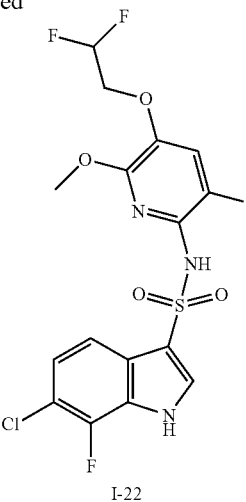

I-22

Step-1: Synthesis of 1-(benzenesulfonyl)-6-chloro-N-[5-(2,2-difluoroethoxy)-3-fluoro-6-methoxy-2-pyridyl]-7-fluoro-indole-3-sulfonamide I-22a In a sealed vial, 5-(2,2-difluoroethoxy)-3-fluoro-6-methoxypyridin-2-amine X-5 (54 mg, 0.24 mmol) was dissolved in pyridine (2 mL) under argon. 1-(benzenesulfonyl)-6-chloro-7-fluoro-indole-3-sulfonyl chloride XII-7 (100 mg, 0.24 mmol) was added at 0° C. then stirred at 70° C. overnight. The reaction mixture was evaporated to dryness. The residue was purified by flash chromatography on silica (eluting with a gradient of DCM and methanol from 100/0 to 98/2) to provide 96 mg of 1-(benzenesulfonyl)-6-chloro-N-[5-(2,2-difluoroethoxy)-3-fluoro-6-methoxy-2-pyridyl]-7-fluoro-indole-3-sulfonamide I-22a as a brown oil.

Yield: 66%.

Basic LCMS Method 1 (ES⁻): 592 (M−H)⁻

Step-2: Synthesis of N-[6-(difluoromethoxy)-5-fluoro-2-methoxypyridin-3-yl]-6-(difluoromethyl)-1H-indole-3-sulfonamide I-16

In a sealed tube, 1-(benzenesulfonyl)-6-chloro-N-[5-(2,2-difluoroethoxy)-3-fluoro-6-methoxy-2-pyridyl]-7-fluoro-indole-3-sulfonamide I-22a (96 mg, 0.16 mmol) was dissolved in THF (1 mL). Tetrabutylammonium fluoride (430 mg, 0.48 mmol) was added and the reaction mixture was stirred at 70° C. for 3 days. The reaction mixture was evaporated to dryness. The residue was dissolved in AcOEt, and washed with water. The organic phase was dried over MgSO₄ and evaporated. The residue was purified by basic preparative HPLC (Method 1) to provide 27 mg of 6-chloro-N-[5-(2,2-difluoroethoxy)-3-fluoro-6-methoxypyridin-2-yl]-7-fluoro-1H-indole-3-sulfonamide I-22 as a white solid.

Yield: 37%.

Basic LCMS Method 1 (ES⁻): 452 (M−H)⁻, 96% purity.

¹H NMR (400 MHz, DMSO-d₆) δ 3.45 (s, 3H), 4.30 (t, J=14.8 Hz, 2H), 6.36 (s, 1H), 7.30 (t, J=7.6 Hz, 1H), 7.56 (t, J=11.5 Hz, 2H), 8.06 (s, 1H), 10.36 (s, 1H), 12.78 (s, 1H).

82

D.6. Synthesis of 6-chloro-N-[5-[2-(difluoromethoxy)ethoxy]-3-fluoro-6-methoxypyridin-2-yl]-7-fluoro-1H-indole-3-sulfonamide I-23

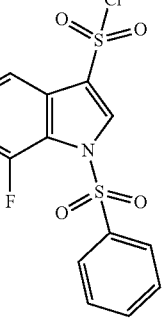

XII-7

+

X-8

→ Pyridine

I-23

To a solution of 5-(2-(difluoromethoxy)ethoxy)-3-fluoro-6-methoxypyridin-2-amine X-8 (74 mg, 0.29 mmol) in pyridine (2 mL), 1-(benzenesulfonyl)-6-chloro-7-fluoro-indole-3-sulfonyl chloride XII-7 (100 mg, 0.24 mmol) was added then stirred at 70° C. for 2 h. The reaction mixture was evaporated to dryness and then residue was purified by a basic prep LCMS Method 1 to provide 54 mg of 6-chloro-N-[5-[2-(difluoromethoxy)ethoxy]-3-fluoro-6-methoxypyridin-2-yl]-7-fluoro-1H-indole-3-sulfonamide I-23 as a pale pink solid.

Yield: 45%.

Basic LCMS Method 1 (ES⁻) 482 (M−H)⁻, 99% purity.

¹H NMR (400 MHz, DMSO-d₆) δ 3.40 (s, 3H), 4.21-4.03 (m, 4H), 6.71 (s, 1H), 7.29 (dd, J=8.6, 6.5 Hz, 1H), 7.56 (d, J=8.6 Hz, 1H), 7.45 (d, J=10.3 Hz, 1H), 8.03 (s, 1H), NH protons not visible.

Synthesis of Comparative Example 1

Comparative Example 1: 6-chloro-N-[3,6-difluoro-5-(2-fluoroethoxy)pyridin-2-yl]-1H-indole-3-sulfonamide

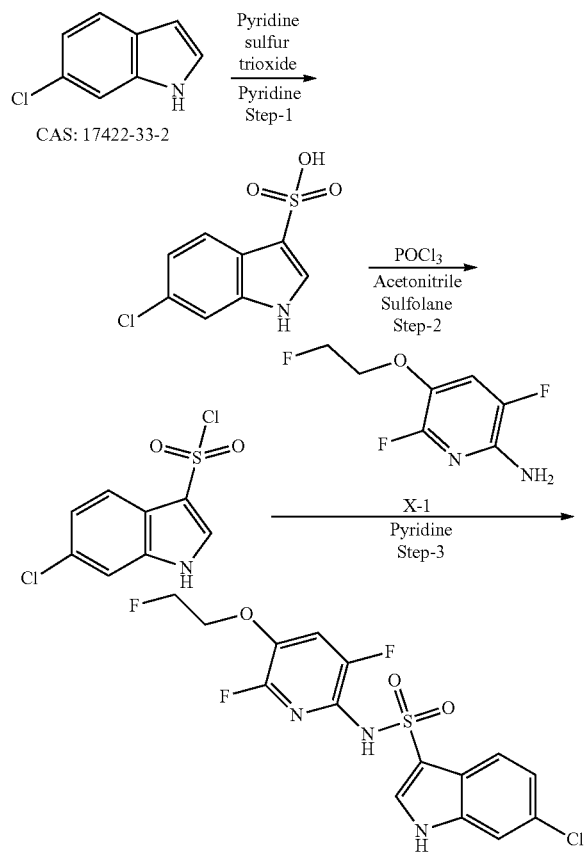

Comparative Example 1

Step-1: Synthesis of 6-chloro-1H-indole-3-sulfonic acid

To a solution of 6-chloroindole (1.00 g, 6.62 mmol) in pyridine (10 mL) was added pyridine sulfur trioxide complex (1.57 g, 9.93 mmol) and the reaction mixture was heated to reflux for 16 h. Progress of the reaction was monitored by TLC and LCMS. After completion, the reaction mixture was diluted with $H_2O$ (100 mL) and extracted with $Et_2O$ (250 mL). The aqueous layer was separated and concentrated under vacuum. The crude obtained was co-evaporated with toluene to afford 6-chloro-1H-indole-3-sulfonic acid (2.30 g crude) as a brown semi solid.

This compound was used as such for the next reaction without further purification.

Basic LCMS Method 2 (ES−): 230 (M−H)−, 98% purity.
$^1$H NMR (400 MHz, DMSO-$d_6$) δ 6.98-7.04 (m, 1H), 7.12-7.26 (m, 1H), 7.44 (s, 1H), 7.69-7.75 (m, 1H), 11.13 (brs, 1H).

Step-2: Synthesis of 6-chloro-1H-indole-3-sulfonyl Chloride

To a solution of 6-chloro-1H-indole-3-sulfonic acid (2.00 g, 6.45 mmol) in sulfolane (5 mL) and $CH_3CN$ (5 mL) was added $POCl_3$ (1.30 mL, 14.2 mmol) drop wise at 0° C. and the reaction mixture was heated at 70° C. for 3 h. Progress of the reaction was monitored by TLC and LCMS. After completion, the reaction mixture was quenched with ice cold $H_2O$ (100 mL) and extracted with EtOAc (2×50 mL). The organic layer was separated, washed with brine (50 mL), dried over anhydrous $Na_2SO_4$ and concentrated under vacuum. The crude obtained was purified by column chromatography (silica, 100-200 mesh, 30% EtOAc in hexanes) to afford 6-chloro-1H-indole-3-sulfonyl chloride (1.00 g) as a light pink solid.

Yield: 62%.
$^1$H NMR (400 MHz, DMSO-$d_6$) δ 7.32 (dd, J=8.56, 1.22 Hz, 1H), 7.71 (s, 1H), 8.03 (d, J=8.80 Hz, 1H), 8.45 (d, J=2.93 Hz, 1H), 12.38 (brs, 1H).

Step-3: Synthesis of 6-chloro-N-[3,6-difluoro-5-(2-fluoroethoxy)pyridin-2-yl]-1H-indole-3-sulfonamide To a stirred solution of 3,6-difluoro-5-(2-fluoroethoxy)pyridin-2-amine X-1 (250 mg, 0.893 mmol) in Pyridine (10.00 ml) was added 6-chloro-1H-indole-3-sulfonyl chloride (558 mg, 2.23 mmol) portion wise at 0° C. then DMAP (5 mg, 0.04 mmol) was added at same temperature. The reaction mixture was heated at 100° C. for 16 h. Progress of the reaction was monitored by TLC. After completion, the reaction mixture was concentrated under vacuum, the residue was triturated with 2N HCl (10 mL), diluted with water (20 mL) and the aqueous layer was extracted with EtOAc (3×25 mL). Combined organic layers were washed by brine (2×30 mL), dried over anhydrous sodium sulphate, filtered and concentrated under vacuum. The crude obtained was purified by column chromatography (silica, 100-200 mesh, 35% EtOAc in hexanes) to afford Comparative Example 1, 6-chloro-N-[3,6-difluoro-5-(2-fluoroethoxy)pyridin-2-yl]-1H-indole-3-sulfonamide (57 mg) as an off-white solid.

Yield: 11%.
Basic LC-MS Method 2 (ES+): 406 (M+H)+, 97% purity.
$^1$H NMR (400 MHz, DMSO-$d_6$) δ 4.24-4.29 (m, 1H) 4.31-4.36 (m, 1H) 4.60-4.65 (m, 1H) 4.72-4.77 (m, 1H) 7.18 (dd, J=8.61, 1.72 Hz, 1H) 7.51 (d, J=1.48 Hz, 1H) 7.70 (d, J=8.86 Hz, 1H) 7.78 (dd, J=9.84, 8.37 Hz, 1H) 7.95 (d, J=2.95 Hz, 1H) 10.49 (s, 1H) 12.06 (brs, 1H).

B. Biology/Pharmacology

B-I. Cell Cultures

GPR17 Recombinant Cell Line:
Flp-In T-REx CHO cells stably expressing human GPR17 receptor (CHO hGPR17) from Evi Kostenis' lab (Bonn University, Germany) were cultured at 37° C. in a humidified atmosphere of 5% $CO_2$. Cells were grown in DMEM with Nutrient Mixture F-12 supplemented with hygromycin B (500 µg/ml) and blasticidin (30 µg/ml). Expression from the Flp-In locus was induced by treatment with doxycycline (1 µg/ml) for 16-20 h prior assays.

Primary Oligodendrocytes:
Primary oligodendrocyte progenitor cells (OPCs) were isolated from the forebrains of Wistar rat pups at postnatal day 0 to 2. Cerebra were mechanically dissociated with a syringe and two different hollow needles (first 1.2×40 and then 0.60×30). Clump-free cell suspension was filtered through a 70-µm cell strainer and plated into poly-D-lysine-coated 75-cm² culture flasks in DMEM supplemented with 10% (v/v) heat-inactivated fetal calf serum, penicillin (100 units/ml), and streptomycin (0.1 mg/ml) with medium exchanged every second day. After 8 to 11 days at 37° C. in a humidified atmosphere of 5% $CO_2$, mixed cultures were shaken at 240 rpm for 14-24 h to detach OPCs from astrocytes and microglia. To further enrich for OPCs, the suspension was plated onto uncoated Petri dishes for 45 min. Then, OPCs were seeded into poly-L-ornithine-coated plates and maintained at 37° C. in a humidified atmosphere of 5% $CO_2$ in proliferating Neurobasal medium supplemented with 2% (v/v) B27, 2 mM GlutaMAX, 100 units/ml penicillin, 0.1 mg/ml streptomycin, 10 ng/ml PDGF-AA, and 10 ng/ml basic FGF changing the medium every second day.

B-II: Functional In Vitro GPR17 Assays

B-II-A: Calcium Mobilization Functional Assay

GPR17 is a G-protein coupled receptor. GPR17 activation triggers Gq-type G-protein signaling resulting in endoplasmic reticulum calcium ($Ca_{2+}$) stores release in cytosol which can be measured using Calcium 5 dye, a fluorescent indicator dye of cytosolic $Ca^{2+}$ levels. The compounds of the present invention were assessed either in the $Ca^{2+}$ assay or in the GPR17 cAMP assay, described further below. Some representative examples were measured in both activity tests as indicated in Table 5, below.

Description of $Ca^{2+}$ assay:

CHO hGPR17 were defrosted and seeded at a density of 20,000 cells per well into black 384-well plates with clear bottom. Cells were incubated overnight at 37° C. in a humidified atmosphere of 5% $CO_2$. Sixteen to twenty hours after seeding, CHO hGPR17 were loaded for 60 min with Calcium 5 dye, a cytosolic $Ca^{2+}$ indicator fluorescent dye, according to manufacturer's instructions. Fluorescent signal relative to cytosolic $Ca^{2+}$ concentration was recorded over time at room temperature in FLIPR Tetra reader. Cells were first incubated for 30 minutes at room temperature in HBSS Hepes buffer pH 7.4 containing increasing concentrations of test compounds (typically $10^{-11}$ M to $10^{-6}$ M). Then, 50 nM MDL29,951, a GPR17 agonist, was added to the cells. Inhibitory effects of varying concentrations test compounds were measured and resulting $pIC_{50}$s were determined. All incubations were performed in duplicate and results were compared to a concentration response curve of GPR17 agonist and antagonist reference compounds. Analysis and curve fitting were performed in ActivityBase XE using XLfit 4-parameter logistic equation $y=A+((B-A)/(1+((C/x)^D)))$ where A, B, C and D stand for minimum y, maximum y, $IC_{50}$ and slope, respectively.

Results of $Ca^{2+}$ Assay:

When tested in $Ca^{2+}$ mobilization assay, compounds of the Examples typically exhibit values of $pIC_{50}$ greater than or equal to 6.5; more preferably greater than or equal to 7.5, and even more preferably greater than or equal to 8.5. The activities of the Example compounds tested are depicted in the table in Section B2B below. The activity ranges A, B and C refer to $pIC_{50}$ values in the $Ca^{2+}$ assay as follows: "A": $pIC_{50}<7.5$, "B": $pIC_{50}$ $7.5 \leq x < 8.5$, "C": $8.5 \leq pIC_{50}$ B-IIB. cAMP Accumulation Functional Assay GPR17 activation can also recruit Gi-type G-protein signaling, resulting in a decrease of intracellular cyclic adenosine monophosphate (cAMP). Intracellular cAMP changes can be measured using the HTRF cAMP dynamic assay kit from CisBio (Codolet, France). Using homogenous time-resolved fluorescence technology (HTRF), the assay is based on competition between native cAMP produced by cells and cAMP labelled with the dye d2. The tracer binding was determined by an anti-cAMP antibody labeled with cryptate.

Description of cAMP Assay

CHO hGPR17 were detached with PBS containing EDTA and dispatched in black 384-well plates with 5,000 cells per well. Cells were first incubated for 30 minutes at room temperature in HBSS Hepes (pH 7.4) containing vehicle or varying concentrations of test GPR17 antagonist/inverse agonist compounds. Then, a dose response curve of MDL29, 951 GPR17 agonist (typically from $10^{-5}$ M to $10^{-10}$ m) was added on vehicle and on each test GPR17 antagonist/inverse agonist compound concentration in a final volume of 20 µL HBSS Hepes buffer (pH 7.4) containing 1% DMSO, 5 µM forskolin and 0.1 mM IBMX. After 60 minutes incubation at room temperature, the reaction is terminated and the cells lysed by adding the d2 detection reagent and the cryptate reagent in 10 µL lysis buffer each according to manufacturer's instructions. After 60 minutes incubation, changes in cAMP concentrations are measured according to manufacturer's instructions using an Envision plate reader with laser excitation. All incubations were performed in duplicate. Data was analyzed using GraphPad Prism software using the 4-parameter logistic equation to measure MDL29,951 $pEC_{50}$s in absence and presence of GPR17 antagonist/inverse agonist test compounds. Dose ratio (DR) were plotted against antagonist concentrations and Schild analysis provided estimated affinity $pA_2$ of GPR17 antagonist/inverse agonist test compounds.

Results of cAMP Assay:

When tested in cAMP assay, compounds of the Examples typically exhibit values of $pA_2$ greater than or equal to 6.5; preferably greater than or equal to 7.5; more preferably greater than or equal to 8.5. The activities of the Example compounds tested are depicted in the table below. The activity ranges A, B and C refer to $pA_2$ values in the cAMP assay as follows: "A": $pA_2<7.5$, "B": $pA_2$ $7.5 \leq x < 8.5$, "C": $8.5 \leq pA_2$.

The following Table 6 shows the $pIC_{50}$ and $pA_2$ values of the Example compounds tested in the $Ca_2$, and the cAMP assay. Blanks in the $pA_2$ column indicate that the respective compounds was not yet tested, or that the result was not yet available.

TABLE 6

| Ex N° | $Ca^{2+}$ assay $pIC_{50}$ | cAMP assay $pA_2$ | Ex N° | $Ca^{2+}$ assay $pIC_{50}$ | cAMP assay $pA_2$ | Ex N° | $Ca^{2+}$ assay $pIC_{50}$ | cAMP assay $pA_2$ |
|---|---|---|---|---|---|---|---|---|
| I-1 | | C | I-2 | | C | I-3 | | C |
| I-5 | | B | I-6 | | B | I-7 | | B |
| I-8 | | A | I-9 | | B | I-10 | | C |
| I-11 | | C | I-12 | | B | I-13 | | C |
| I-14 | | B | I-15 | | C | I-16 | | C |
| I-17 | | B | I-18 | | B | I-19 | | A |
| I-20 | | C | I-21 | | B | I-22 | | C |
| I-23 | | C | | | | | | |

B-IIC: Oligodendrocyte Maturation/Myelination Assays

The effects of negative modulators of GPR17 on primary oligodendrocytes maturation/myelination can be assessed in vitro by immunoassays using antibodies directed against Myelin Basic Protein (MBP), as marker for mature oligodendrocytes.

Description of MBP Western Blot/Oligodendrocyte/Myelination Assay

After 3-4 days in proliferation medium, rat primary OPCs were seeded at 25,000 cells per cm² in 12-well tissue culture plates and switched to growth factor-free Neurobasal medium to induce spontaneous in vitro differentiation and GPR17 protein expression. For terminal differentiation and quantification analyses of protein expression, after 24-48 h the growth factor-free medium was supplemented with 0.20 ng/mL triiodothyronine (T3) and 10 ng/mL ciliary neurotrophic factor together with 1 µM GPR17 antagonist/inverse agonists test compounds or vehicle for additional 3 days. Following compound treatment, cells were washed twice with ice-cold PBS and lysed in ice-cold lysis buffer (25 mM Tris, pH 7.4, 150 mM NaCl, 1 mM EDTA, 1% Triton X-100, 1% IGEPAL) supplemented with protease inhibitor mixture. Lysates were rotated 20 min at 4° C. and centrifuged at 15,000×g at 4° C. for 10 min. Protein concentration was determined using the Pierce BCA Protein Assay according to manufacturer's instructions. 7.5-15 µg of protein were separated by 10% SDS-polyacrylamide gel electrophoresis and transferred to nitrocellulose membrane by electroblotting. After washing, membranes were blocked with Roti-Block for 1 h at room temperature and incubated overnight at 4° C. in Roti-Block with MBP antibody (1:5000, LifeSpan Bio-Sciences). Membranes were washed 3 times with PBS containing 0.1% Tween and then incubated for 1 h at room temperature with a horseradish peroxidase-conjugated goat anti-mouse IgG antibody in Roti-Block. The immunoreactive proteins were visualized by chemiluminescence using Amersham Biosciences ECL Prime Western blotting detection reagent and quantified by densitometry using Gelscan software. To normalize for equal loading and protein transfer, membranes were reprobed with an antibody against r3-actin (1:2500, BioLegend; secondary antibody goat anti-rabbit IgG antibody HRP (ABIN)). Changes in MBP expression level in the presence of test compounds were compared to MBP expression in control conditions.

Description of MBP Fiber Plates/Oligodendrocyte Maturation/Myelination Assay

OPCs were seeded at 16,000-22,000 cells per cm² in Mimetix Aligned 96-well fiber plates (Electrospining company). After 2 days in proliferation medium and 2 days in growth factor-free Neurobasal medium to induce spontaneous in vitro differentiation and GPR17 protein expression, vehicle or 1 µM antagonist/inverse agonist test compounds were added in terminal differentiation medium supplemented with 0.20 ng/mL triiodothyronine and 10 ng/mL ciliary neurotrophic factor for 6 days, changing the medium after 3 days. Then cells were fixed in 4% paraformaldehyde, followed by PBS washes, permeabilization in 0.1% TritonX-100 in PBS and blocking with 10% goat serum and 1% bovine serum albumin in phosphate-buffered saline. MBP antibody was diluted in blocking buffer (1:2000) and incubated for 1 h at 37° C. Cells were washed in PBS again and incubated 1 h with Cy2-conjugated secondary antibodies against mouse IgG (Millipore, 1:500). After PBS washes, cells were stained with 0.2 µg/mL DAPI, washed again and mounted with Mowiol. Fluorescent images were taken by using a Zeiss AxioObserver.Z1 microscope with ApoTome Imaging System and a Plan-Apochromat 20x/0.8 objective, with an eGFP filter (excitation 470/40 nm; emission 525/50 nm) and DAPI filter (excitation 365 nm; emission 445/50 nm). At least 15 random areas for control (terminal differentiation medium with 0.1% DMSO) and for test compounds were imaged using the same settings processed with Zeiss ZEN2.3 software. Changes in number myelinated fibers was reported by group of fiber lengths (0 to 40 µm, 41 to 60 µm, 61 to 80, 81 to 100, 101 to 120 and >120 µm)) in the absence or presence of GPR17 negative modulator.

CYP 450-1A2 Induction Assay

Cryopreserved human hepatocytes from a single donor are seeded on a 96 well collagen coated plate so that the final seeding density is 0.1×106 cells/well (final volume per well 0.1 mL). The cells are then incubated in seeding medium at 37° C., 95% humidity, 5% $CO_2$ to allow the cells to attach. After 4 h, the seeding medium is replaced with 0.1 mL of pre warmed serum free Williams E medium containing 100 IU/mL penicillin, 100 µg/mL streptomycin, 10 µg/mL insulin, 2 mM L glutamine and 0.1 µM hydrocortisone.

The next day, cells are dosed with test compound in assay medium (final test compound concentration 10 µM; final DMSO concentration 0.1%). Positive control inducers, omeprazole (50 µM) for CYP1A2, phenobarbital (500 µM) for CYP2B6 and rifampicin (10 µM) for CYP3A4, are incubated alongside the test compound. Negative control wells are included where the test compound is replaced by vehicle solvent (0.1% DMSO in assay medium). Each test compound is dosed in triplicate. The cells are exposed to the solutions for 72 h with fresh solution added every 24 h.

For catalytic activity determination, a solution of the probe substrates, phenacetin (final concentration 25 µM), bupropion (final concentration 100 µM) and midazolam (final concentration 2.5 µM) is prepared in pre warmed assay medium. At the end of the 72 h exposure period, the media is replaced with the cocktail of probe substrates. The hepatocytes are incubated for 30 min. An aliquot is removed at the end of the incubation period and placed into methanol containing internal standard in a 1:2 ratio. The samples are centrifuged at 2500 rpm at 4° C. for 20 min. An aliquot of supernatant is diluted with deionised water and levels of acetaminophen, hydroxybupropion and 1 hydroxymidazolam are quantified using Cyprotex generic LC MS/MS methods.

The hepatocytes are solubilised in 0.1M sodium hydroxide at room temperature and protein content in each well determined using Pierce™ BCA Protein Assay Kit (Thermo Scientific) using bovine serum albumin as a standard.

For catalytic activity determination, the concentration of metabolite formed at each test compound replicate is converted to CYP activity and normalised to protein. The fold change is determined by comparing to the vehicle control wells. The fold change observed at each test compound concentration is expressed as a percentage of the positive control compounds for each P450 isoform.

The compounds of the present invention typically show no or at least significantly less CYP 1A2 induction than comparative compounds with an hydrogen in the R7 position.

As an illustration, example compounds 1-1, 1-2, 1-3 and 1-12, wherein R7 is chlorine, cyclopropyloxy, difluoromethyl and cyclopropyl, respectively, showed no CYP1A2 induction compared to vehicle control, whereas the corresponding Comparative Example 1 (6-chloro-N-[3,6-difluoro-5-(2-fluoroethoxy)pyridin-2-yl]-1H-indole-3-sulfonamide), wherein R7 is hydrogen, displayed 16-fold induction of CYP1A2.

The invention claimed is:

1. A compound having Formula I

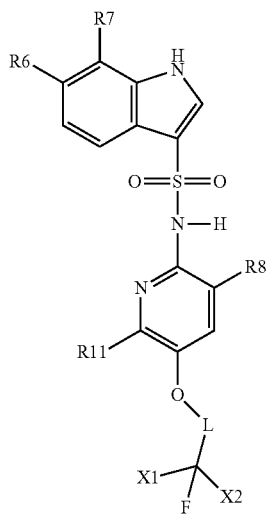

Formula I wherein

R6 is selected from chloro, fluoro, fluoromethyl and fluoromethoxy,

R7 is selected from fluoro, chloro, cyclopropyl, cyclopropyloxy, fluoromethyl, and fluoromethoxy, R8 is fluoro or methoxy, R11 is hydrogen, fluoro or methoxy, L is a bond, or a linker selected from —CH2- and —CH2-CH2-O—, X1 and X2 are independently selected from hydrogen and fluoro, or a pharmaceutically acceptable salt, solvate, isotope or cocrystal thereof.

2. A compound according to claim 1, wherein R6 is chloro.

3. A compound according to claim 1, wherein R6 is fluoromethyl.

4. A compound according to claim 1, wherein R7 is selected from fluoromethyl, cyclopropyloxy, fluoro and chloro.

5. A compound according to claim 1, wherein X1 is hydrogen.

6. A compound according to claim 1, wherein R8 is fluoro and wherein L is selected from (a) a bond (b) —CH2- and (c) —CH2-CH2-O—, such compound thus having a structure according to Formulae IIa, IIb or IIc,

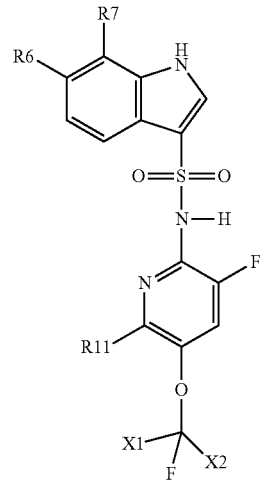

Formula IIa

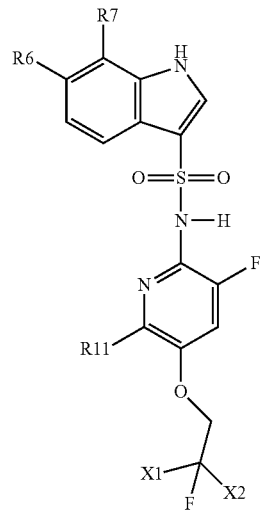

Formula IIb

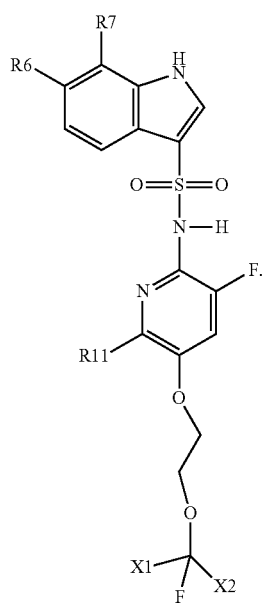

Formula IIc

7. A compound according to claim 6, wherein

R6 is selected from chloro and fluoromethyl;

R7 is selected from fluoro, chloro, cyclopropyl, cyclopropyloxy, fluoromethyl and fluoromethoxy;

R11 is selected from hydrogen, methoxy and fluoro;

X1 and X2 are independently selected from hydrogen and fluoro.

8. A compound according to claim 1, wherein R8 and R11 are both fluoro and wherein L is selected from (a) a bond (b) —CH2- and (c) —CH2-CH2-O—, such compound thus having a structure according to Formula IIIa, IIIb, or IIIc, Formula IIIa

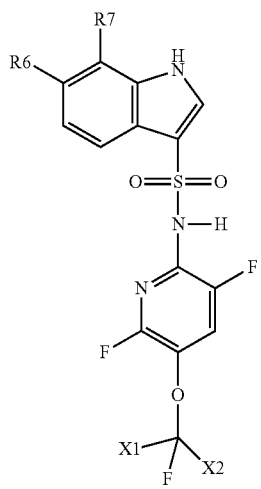

Formula IIIb

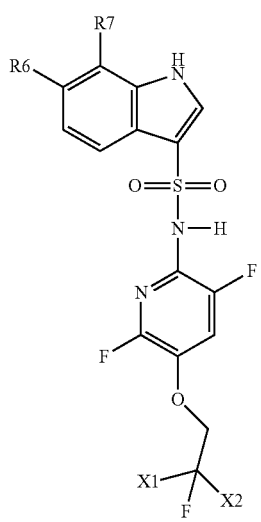

Formula IIIc

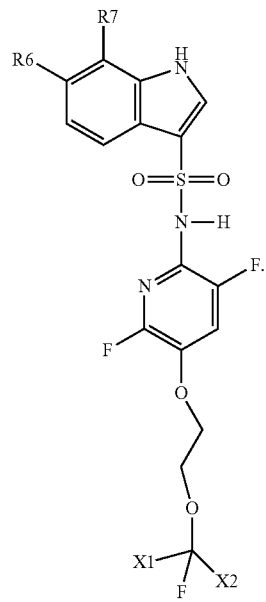

9. A compound according to claim 1, wherein, R11 is methoxy and wherein L is selected from (a) a bond (b) —CH2- and (c) —CH2-CH2-O—, such compound thus having a structure according to Formula Va, Vb or Vc:

Formula Va

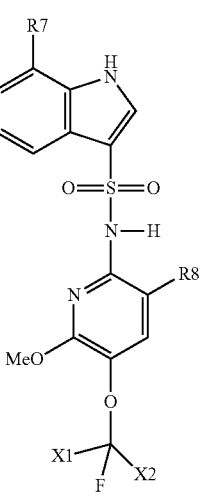

Formula Vb

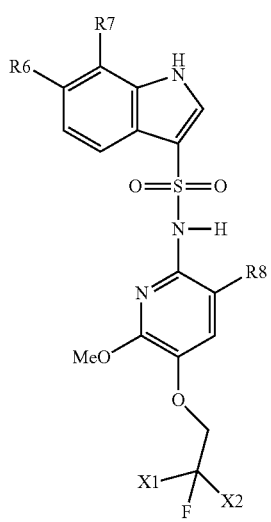

Formula Vc

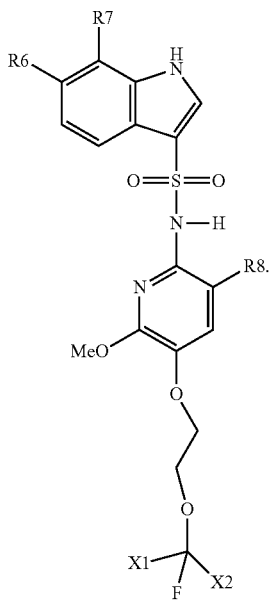

10. A compound according to claim 9, wherein
R6 is selected from fluoro, chloro, fluoromethyl and fluoromethoxy,
R7 is selected from fluoro, chloro, cyclopropyl, cyclopropyloxy, fluoromethyl, and fluoromethoxy,
R8 is fluoro, and
X1 and X2 are independently selected from hydrogen and fluoro.

11. A compound according to claim 1, wherein R6 and R7 are independently selected from chloro and difluoromethyl and wherein X1 is hydrogen, and X2 is hydrogen or fluoro.

12. A compound according to claim 1, wherein X1 is hydrogen and X2 is fluoro.

13. A compound selected from
6,7-dichloro-N-[5-(2,2-difluoroethoxy)-3-methoxypyridin-2-yl]-1H-indole-3-sulfonamide;
7-chloro-N-[5-(2,2-difluoroethoxy)-3-fluoro-6-methoxypyridin-2-yl]-6-(difluoromethyl)-1H-indole-3-sulfonamide;
6-chloro-N-[5-[2-(difluoromethoxy)ethoxy]-3-fluoro-6-methoxypyridin-2-yl]-7-fluoro-1H-indole-3-sulfonamide;
6-chloro-N-[5-(2,2-difluoroethoxy)-3-fluoro-6-methoxypyridin-2-yl]-7-fluoro-1H-indole-3-sulfonamide;
N-[5-(2,2-difluoroethoxy)-3-fluoropyridin-2-yl]-6-(difluoromethyl)-7-fluoro-1H-indole-3-sulfonamide;
6-chloro-N-[3,6-difluoro-5-(2-fluoroethoxy)pyridin-2-yl]-7-(trifluoromethoxy)-1H-indole-3-sulfonamide;
6-chloro-N-[5-(difluoromethoxy)-3-methoxypyridin-2-yl]-7-(difluoromethyl)-1H-indole-3-sulfonamide;
6,7-dichloro-N-[5-(difluoromethoxy)-3-methoxypyridin-2-yl]-1H-indole-3-sulfonamide;
6-chloro-N-[5-(2,2-difluoroethoxy)-3-fluoro-6-methoxypyridin-2-yl]-7-(difluoromethyl)-1H-indole-3-sulfonamide;
6-chloro-N-[5-(2,2-difluoroethoxy)-3-fluoropyridin-2-yl]-7-(difluoromethyl)-1H-indole-3-sulfonamide;
7-chloro-N-[3-fluoro-5-(2-fluoroethoxy)pyridin-2-yl]-6-(difluoromethyl)-1H-indole-3-sulfonamide;
6-(difluoromethyl)-7-fluoro-N-[3-fluoro-5-(2-fluoroethoxy)pyridin-2-yl]-1H-indole-3-sulfonamide;
6-chloro-7-(difluoromethyl)-N-[3-fluoro-5-(2-fluoroethoxy)pyridin-2-yl]-1H-indole-3-sulfonamide;
6,7-dichloro-N-[5-(2,2-difluoroethoxy)-3-fluoropyridin-2-yl]-1H-indole-3-sulfonamide;
6,7-dichloro-N-[3-fluoro-5-(2-fluoroethoxy)pyridin-2-yl]-1H-indole-3-sulfonamide;
6-chloro-N-[3,6-difluoro-5-(2-fluoroethoxy)pyridin-2-yl]-7-fluoro-1H-indole-3-sulfonamide;
6-chloro-N-[5-(2,2-difluoroethoxy)-3,6-difluoropyridin-2-yl]-7-fluoro-1H-indole-3-sulfonamide;
6-chloro-7-cyclopropyl-N-[3,6-difluoro-5-(2-fluoroethoxy)pyridin-2-yl]-1H-indole-3-sulfonamide;
6-chloro-N-[3,6-difluoro-5-(2-fluoroethoxy)pyridin-2-yl]-7-(difluoromethyl)-1H-indole-3-sulfonamide;
6-chloro-7-cyclopropyloxy-N-[3,6-difluoro-5-(2-fluoroethoxy)pyridin-2-yl]-1H-indole-3-sulfonamide;
and pharmaceutically acceptable salts, solvates, isotopes and cocrystals thereof.

14. A pharmaceutical composition comprising a compound according to claim 1 and a pharmaceutically acceptable carrier.

15. A method of treating a demyelination disorder, the method comprising administering to a subject in need thereof a compound according to claim 1.

16. A method according to claim 15, wherein the a demyelination disorder is multiple sclerosis.

17. A compound according to claim 2, wherein R7 is selected from fluoromethyl, cyclopropyloxy, fluoro and chloro.

18. A compound according to claim 3, wherein R7 is selected from fluoromethyl, cyclopropyloxy, fluoro and chloro.

19. A compound according to claim 2, wherein X1 is hydrogen.

20. A compound according to claim 3, wherein X1 is hydrogen.

* * * * *